United States Patent [19]

Yokura et al.

[11] Patent Number: 5,661,166

[45] Date of Patent: Aug. 26, 1997

[54] SAISHIN N COMPOUNDS, PROCESS FOR PREPARING SAME AND ANTIULCER AGENTS CONTAINING SAME

[75] Inventors: Susumu Yokura, Kawagoe; Kiyokazu Murakami, Yokohama; Nobuo Takoi, Musashino; Hiroyuki Iizuka, Tokyo; Eiji Ohtubo, Yono, all of Japan

[73] Assignee: Tokyo Tanabe Co. Ltd., Tokyo, Japan

[21] Appl. No.: 402,900

[22] Filed: Mar. 13, 1995

Related U.S. Application Data

[63] Continuation-in-part of Ser. No. 932,628, Aug. 20, 1992, abandoned.

[30] Foreign Application Priority Data

Aug. 21, 1991 [JP] Japan ............... 3-291834

[51] Int. Cl.⁶ .................. A61K 31/415; C07D 207/02
[52] U.S. Cl. .................. 514/365; 548/535; 548/201; 548/307.4; 549/397; 549/416; 560/43; 560/106; 514/535; 514/544; 514/395; 514/423; 514/456; 514/460
[58] Field of Search .................. 548/535, 201, 548/307.4; 549/397, 416; 560/43, 106; 514/535, 544, 365, 395, 423, 456, 460

[56] References Cited

U.S. PATENT DOCUMENTS 5,151,450  9/1992  Murakami et al. .

OTHER PUBLICATIONS

Eichenberger et al., Helv. Chim. Acta, 63(6), 1499–1519 (1980) (German).

*Primary Examiner*—Johann Richter
*Assistant Examiner*—John Peabody
*Attorney, Agent, or Firm*—McGlew and Tuttle

[57] ABSTRACT

A Saishin N derivative represented by the following general formula:

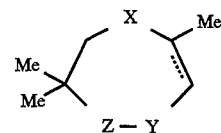

wherein X represents a carbonyl group or a >CH—ORx group, or X bonds to a carbon atom in Y or Z to represent a >C(ORx)—O— group; Y and Z may be the same or different and each represents a carbonyl group or a >CH—ORy group, or each bonds to an oxygen atom in X to represent a >CH— group; the broken line represents an optional bond; and Rx and Ry may be the same or different and each represents a hydrogen atom or an alkyl, alkenyl, aralkenyl, aralkyl, heterocyclic-alkyl or acyl group, is provided which is therapeutically usable as an antiulcer agent.

28 Claims, No Drawings

1

SAISHIN N COMPOUNDS, PROCESS FOR PREPARING SAME AND ANTIULCER AGENTS CONTAINING SAME

CROSS REFERENCE TO RELATED APPLICATIONS

This application is a continuation in part of U.S. application Ser. No. 07/932,628 filed Aug. 20, 1992, now abandoned.

BACKGROUND OF THE INVENTION

1. Field of the Invention

The present invention relates to terpenoid compounds constituting derivatives of Saishin N described below, a process for preparing the derivatives and antiulcer agents containing the derivatives as an effective component. The present invention relates more particularly to a Saishin N derivative useful as a medicament for a peptic ulcer, a process for preparing the derivative and an antiulcer agent containing the derivative as an effective component.

The inventors of this invention had isolated and identified Saishin N of the below formula, i.e. 4,5-dihydroxy-2,6,6-trimethyl-2-cyclohepten-1-one, from a crude drug "Saishin" as an antiulcer material and developed a chemical method for preparing Saishin N and filed a Patent Application thereon (Japanese Unexamined Patent Publication No. 275640/1991), i.e. U.S. Ser. No. 659,754 filed Feb. 21, 1991, now U.S. Pat. No. 5,151,450, issued Sep. 29, 1992:

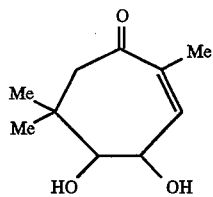

Saishin N has two hydroxy groups in the molecule and up to now it had been thought that there were no significant differences between the groups, because it was found to be difficult to react one of the hydroxy groups selectively, which has been an obstacle to the study of Saishin N derivatives.

2. Description of the Prior Art

Eichenberger et al, Helv. Chim. Acta, 63 (6), 1499–1519 (Ger.) 1980, discloses (per its English abstract) the photochemical isomerization of certain keto-enones, methanol addition thereto and photodecarbonylation thereof, no pertinent utility being indicated for these remote type compounds.

SUMMARY OF THE INVENTION

The inventors have conducted studies and have found that
(1) when eucarvone-4,5-oxide (chemical name: 4,5-epoxy-2,6,6-trimethyl-2-cyclohepten-1-one), which is an intermediate in the production of Saishin N, is subjected to an alcoholysis reaction in the presence of an acid catalyst, only a Saishin N derivative having an alkoxy group in the 4-position and a hydroxy group in the 5-position may be obtained selectively; and
(2) when Saishin N and a carboxylic acid are subjected to an acylation reaction using a condensation agent such as carbodiimide, only a Saishin N derivative having an acyloxy group in the 4-position and a hydroxy group in the 5-position may be obtained selectively.

2

The inventors further have studied the modification of the hydroxy groups in the 4- and 5-positions, the reduction of a double bond, the reduction of an oxo group to a hydroxy group and the modification of the hydroxy group and have found compounds having more excellent antiulcer effect than Saishin N and thus have completed the present invention.

The various features of novelty which characterize the invention are pointed out with particularity in the claims annexed to and forming a part of this disclosure. For a better understanding of the invention, its operating advantages and specific objects attained by its uses, reference is made to the accompanying descriptive matter and examples in which preferred embodiments of the invention are illustrated.

DESCRIPTION OF THE PREFERRED EMBODIMENTS

According to the invention, there is provided an antiulcer agent containing as an effective component a Saishin N derivative (hereinafter referred to as "Compound A") represented by the following general formula:

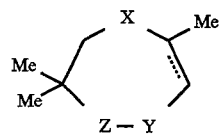

wherein:
X represents a carbonyl group or a

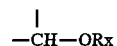

(hereinafter >CH—ORx) group, i.e. a diyl (ylidene) group, or X bonds to a carbon atom in Y or Z to represent a

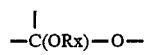

(hereinafter >C(ORx)—O—) group, i.e. a triyl (ylidyne) group;
Y and Z may be the same or different and each represents a carbonyl group or a

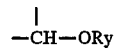

(hereinafter >CH—ORy) group, i.e. a diyl (ylidene) group, or each bonds to an oxygen atom in X to represent a

(hereinafter >CH—) group, i.e. a triyl (ylidene) or specifically methylidyne group;
the broken line represents an optional bond; and
Rx and Ry may be the same or different and each represents a hydrogen atom or an alkyl, alkenyl, aralkenyl (i.e. arylalkenyl, especially in which the aryl moiety has 6 to 10 ring carbon atoms, such as styryl and cinnamyl), aralkyl (i.e. arylalkyl, especially in which the aryl moiety has 6 to 10 ring carbon atoms, such as benzyl and phenethyl), heterocyclic-alkyl (i.e. heterocyclic substituted alkyl, especially in which the heterocyclic moiety is a 5 to 10, more especially 5 to 9, or 5 to 6, membered ring system having at least one S, N or O heteroatom therein, such as thenyl, picolyl and furfuryl) or acyl group;

provided that when X is a carbonyl group and the broken line is a bond and Y is a >CH—ORy group and Z is also a >CH—ORy group, then only one Ry thereof may be a hydrogen atom, thereby excluding Saishin N.

Examples of the alkyl group include a lower alkyl group, especially having 1 to 4 carbon atoms, which may have substituents on the chain. Examples of the substituents include a hydroxy group which may be protected by a lower acyl group having 1 to 4 carbon atoms, by an acetal such as a tetrahydropyranyl, tetrahydrothiopyranyl, 4-methoxytetrahydropyranyl, tetrahydrofuranyl, 1-ethoxyethyl, 1-methyl-1-methoxyethyl and 1-isopropyloxyethyl group or by a silyl ether such as trimethylsilyl ether and tert-butyldimethylsylyl ether (hereinafter the same definition is applied to the protective group of the hydroxy group); a carboxyl group; and a lower alkoxycarbonyl group having 1 to 4 carbon atoms.

Examples of the alkenyl group include a lower alkenyl group, especially having 2 to 5 carbon atoms, such as an allyl group and a 3-methyl-2-butenyl group.

Examples of the aralkenyl group include a phenyl alkenyl group and a naphthyl alkenyl group, especially in which the alkenyl moiety is a lower alkenyl group, in particular having 2 to 5, more particularly 2 to 4, carbon atoms, such as a styryl group and a cinnamyl group, which may have one or more substituents on the ring.

Examples of the aralkyl group include a phenyl alkyl group and a naphthyl alkyl group, especially in which the alkyl moiety is a lower alkyl group having 1 to 4 carbon atoms, such as a benzyl group and a phenethyl group, which may have one or more substituents on the ring.

Examples of the heterocyclic-alkyl group include a thenyl (i.e. thienyl methyl or thiacyclopenta-2,4-diene-methyl) group, a picolyl group and a furfuryl group, which groups may have one or more substituents on the ring.

Examples of the substituents on the ring of the aralkenyl, e.g. cinnamyl, aralkyl or heterocyclic-alkyl group include a lower alkyl group having 1 to 4 carbon atoms; a lower alkoxycarbonyl group having 1 to 4 carbon atoms; an acyl group such as an acetyl, benzoyl or cinnamoyl group; a hydroxy group which may be protected by a said protective group; a lower alkoxy group having 1 to 4 carbon atoms; a fluorine, chlorine, bromine or iodine (i.e. halogen) atom; and a nitro group.

Examples of the acyl group include:
an aliphatic acyl group, especially an alkanoyl or alkenoyl group, such as an acetyl, propionyl, butyryl, isobutyryl, valeryl, acryloyl, methacryloyl or 2-butenoyl group which may have substituents on the chain;
an aromatic-aliphatic acyl group, especially an aralkenoyl, i.e. arylalkenoyl, group, in particular in which the aryl moiety has 6 to 10 ring carbon atoms, and the alkenyl moiety is a lower alkenyl group, especially having 2 to 5, more especially 2 to 4, carbon atoms, such as a cinnamoyl group, which may have one or more substituents on the ring;
an aromatic acyl group, especially an aroyl group, in particular having 6 to 10 ring carbon atoms in the aryl moiety, such as a benzoyl or naphthoyl group, which may have one or more substituents on the ring; or
a heterocyclic acyl group, especially in which the heterocyclic moiety is a 5 to 10, more especially 5 to 9, membered ring system having at least one S, N or O heteroatom therein, including a heterocyclic alkanoyl group, especially a heterocyclic lower alkanoyl group, in particular having 2 to 4 carbon atoms in the alkanoyl moiety, such as a thiazolyl-acetyl group, and further including a heterocyclic carbonyl group, such as a furoyl, pyrrolyl carbonyl, thenoyl (i.e. thiacyclopenta-2,4-dienyl-carbonyl), imidazolyl carbonyl and benzlmadazolyl carbonyl group, which heterocyclic alkanoyl and heterocyclic carbonyl groups may have one or more substituents on the ring.

Examples of the substituents on the chain of the aliphatic acyl group include a hydroxy group which may be protected by a said protective group; a carboxyl group; and a lower alkoxycarbonyl group having 1 to 4 carbon atoms (and also a thiazolyl group in the sense of a heterocyclic substituted alkyl carbonyl group, or simply a heterocyclic alkanoyl group as earlier defined).

Examples of the substituents on the aromatic or heterocyclic ring of the acyl group include a lower alkyl group having 1 to 4 carbon atoms; a carboxyl group; a lower alkoxycarbonyl group having 1 to 4 carbon atoms; an acyl group such an acetyl, benzoyl and cinnamoyl group, which may have one or more substituents on the chain or ring; a hydroxy group which may be protected by a said protective group; a lower alkoxy group having 1 to 4 carbon atoms; a lower acyloxy, especially lower alkanoyloxy, group such as an acetoxy, propionyloxy or butyryloxy group; a fluorine, chlorine, bromine or iodine (i.e. halogen) atom; a nitro group; and an amino group which may be substituted by an acyl group such as an acetyl, benzoyl or cinnamoyl group or by a lower alkyl group having 1 to 4 carbon atoms.

Compound A of the invention also includes each or the mixture of the stereoisomers which exist due to a plurality of asymmetric carbon atoms present.

The method for preparing Compound A will be explained hereinafter. Eucarvone-4,5-oxide, i.e. 4,5-epoxy-2,6,6-trimethyl-2-cyclopenten-1-one (hereinafter referred to as "Compound B") is prepared by the method described in Japanese Unexamined Patent Publication No. 275640/1991, and U.S. Pat. No. 5,151,450, noted above.

Process [a]

Process [a] comprises alcoholizing Compound B in the presence of an acid catalyst to obtain Compound C and Compound K:

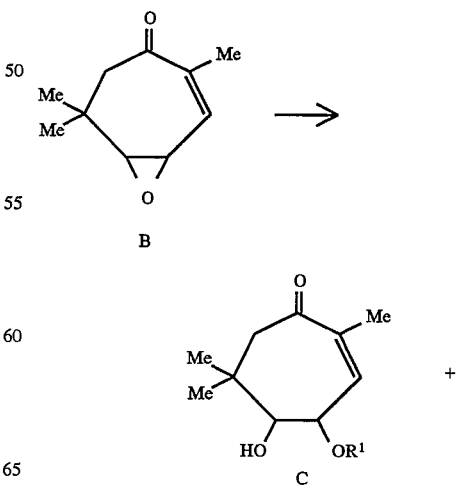

-continued

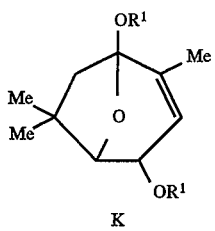

K wherein per process [a] $R^1$ represents an alkyl, alkenyl, arakenyl, aralkyl or heterocyclic-alkyl group, as more fully defined above.

Examples of the alkyl group include a lower alkyl group having 1 to 4 carbon atoms which may have substituents on the chain. Examples of the substituents on the chain include a hydroxy group which may be protected by a said protective group; a carboxyl group; or a lower alkoxycarbonyl group having 1 to 4 carbon atoms.

Examples of the alkenyl group include an allyl or 3-methyl-2-butenyl group.

Examples of the aralkenyl group include a styryl or cinnamyl group, which may have one or more substituents on the ring.

Examples of the aralkyl group include a benzyl or phenethyl group, which may have one or more substituents on the ring.

Examples of the heterocyclic-alkyl group include a furfuryl, thenyl or picolyl group, which may have one or more substituents on the ring.

Examples of the substituents on the ring of the aralkenyl, e.g. cinnamyl, arakyl or heterocyclic-alkyl group include a lower alkyl group having 1 to 4 carbon atoms; a lower alkoxycarbonyl group having 1 to 4 carbon atoms; an acyl group such as an acetyl, benzoyl or cinnamoyl group; a hydroxy group which may be protected by a said protective group; a lower alkoxy group having 1 to 4 carbon atoms; a fluorine, chlorine, bromine or iodine (i.e. halogen) atom; and a nitro group.

The solvent used in the reaction may not be limited if the mixture of Compound B and the alcohol used in the reaction can dissolve in the solvent, but an inert solvent such as aromatic hydrocarbons such as benzene, toluene and xylene; halogenated hydrocarbons such as dichloromethane, chloroform and carbon tetrachloride; and ethers such as diethylether, tetrahydrofuran and dioxane are preferable. The alcohol itself used in the alcoholysis may be used as a solvent.

Examples of the acid used as acid catalyst include inorganic acids such as hydrochloric acid, sulfuric acid, nitric acid, hydrobromic acid and phosphoric acid; Lewis acids such as boron trifluoride etherate, titanium tetrachloride, zinc chloride and tin tetrachloride; or sulfonic acids such as methane sulfonic acid, camphor sulfonic acid, benzene sulfonic acid and toluene sulfonic acid.

Examples of the alcohol (e.g. $R^1$—OH) include a saturated aliphatic alcohol, e.g. an alkanol, an unsaturated aliphatic alcohol, e.g. an alkenol, an aromatic-unsaturated aliphatic alcohol, e.g. an aralkenol, i.e. an arylalkenyl alcohol, an aromatic-saturated aliphatic alcohol, e.g. an aralkanol, i.e. an aralkyl alcohol, and a heterocyclic-aliphatic alcohol, e.g. a heterocyclic-alkanol.

Examples of the saturated aliphatic alcohol include a saturated aliphatic alcohol having 1 to 4 carbon atoms which may have substituents on the chain. Examples of the substituents on the chain include a hydroxy group which may be protected by a said protective group; a carboxyl group; or an alkoxycarbonyl group having 1 to 4 carbon atoms.

Examples of the unsaturated aliphatic alcohol include an allyl alcohol and a 3-methyl-2-buten-1-ol.

Examples of the aromatic-unsaturated aliphatic alcohol include a styryl alcohol and a cinnamyl alcohol, which may have one or more substituents on the ring.

Examples of the aromatic-saturated aliphatic alcohol, e.g. aralkyl alcohol, include a benzyl alcohol and a phenethyl alcohol, which may have one or more substituents on the ring.

Examples of the heterocyclic-aliphatic alcohol, e.g. heterocyclic-alkanol, include a furfuryl alcohol, a thenyl alcohol (i.e. thiacyclopenta-2,4-dien-methanol), and a picolyl alcohol, which may have one or more substituents on the ring.

Examples of the substituents on the ring of the aromatic-unsaturated aliphatic alcohol, e.g. cinnamyl alcohol, aromatic-saturated aliphatic alcohol, e.g. aralkyl alcohol, or heterocyclic-aliphatic alcohol, e.g. heterocyclic-alkanol, include a lower alkyl group having 1 to 4 carbon atoms; a lower alkoxycarbonyl group having 1 to 4 carbon atoms; an acyl group such as an acetyl, benzoyl or cinnamoyl group; a hydroxy group which may be protected by a said protective group; a lower alkoxy group having 1 to 4 carbon atoms; a fluorine, chlorine, bromine or iodine (i.e. halogen) atom; or a nitro group.

The reaction may be carried out at −70° to 200° C., preferably at 0° to 100° C., with or without stirring, until the reaction is completed.

After completion of the reaction, the reaction mixture is subjected to column chromatography to separate Compound C and the bicyclic type compound, Compound K.

Compound K may be converted into Compound C by acid hydrolysis in a good yield.

The acid hydrolysis is preferably carried out in water but a polar solvent such as alcohol, tetrahydrofuran, dioxane, acetone or dimethylformamide, may be added in order to dissolve Compound K.

Examples of the acid used for the acid hydrolysis include an inorganic acid such as hydrochloric acid, sulfuric acid, nitric acid, hydrobromic acid or phosphoric acid; an organic acid such as formic acid, acetic acid, propionic acid or butyric acid; or a sulfonic acid such as methane sulfonic acid, camphor sulfonic acid, benzene sulfonic acid or toluene sulfonic acid.

The reaction may be carried out at −70° to 200° C., preferably at 0° to 100° C., with or without stirring, until the reaction is completed.

Process [b]

Process [b] comprises acylating Compound C to obtain Compound D and Compound L:

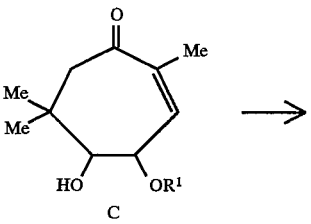

C

-continued

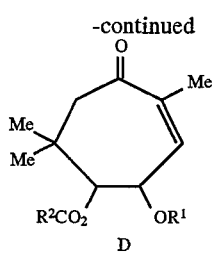
D

+

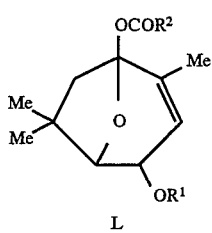
L wherein per process [b] R¹ has the same meaning as defined above and R² represents an alkyl, alkenyl, aralkenyl (especially in which the aryl moiety has 6 to 10 ring carbon atoms and the alkenyl moiety is a lower alkenyl group, in particular having 2 to 5, more particularly 2 to 4, carbon atoms, such as styryl and cinnamyl), aromatic hydrocarbon (including aryl having 6 to 10 ring carbon atoms such as phenyl and naphthyl), heterocyclic-alkyl, or heterocyclic, group (the heterocyclic moiety of the heterocyclic-alkyl and heterocyclic groups being especially a 5 to 10, more especially 5 to 9, membered ring system having at least one S, N or O heteroatom therein, the alkyl moiety of the heterocyclic-alkyl group being especially a lower alkyl group, in particular having 1 to 4 carbon atoms, such as a thiazolyl-methyl group, and the heterocyclic group being a group such as a thienyl (i.e. thiacyclopenta-2,4-dienyl), pyrrolyl, furyl, imidazolyl and benzimidazolyl group).

Examples of the alkyl group as R² include a lower alkyl group which may have 1 to 4 carbon atoms and which may have substituents on the chain. Examples of the substituents on the chain include a hydroxy group which may be protected by a said protective group; a carboxyl group; and a lower alkoxycarbonyl group having 1 to 4 carbon atoms (and also a thiazolyl group in the sense earlier defined).

Examples of the alkenyl group as R² include a lower alkenyl group having 2 to 5 carbon atoms.

Examples of the aralkenyl group as R² include a styryl group and a cinnamyl group, which may have one or more substituents on the ring.

Examples of the aromatic hydrocarbon group as R² include an aryl group such as a phenyl or naphthyl group, which may have one or more substituents on the ring.

Examples of the heterocyclic-alkyl group as R² include a thiazolyl-methyl group, which may have one or more substituents on the ring.

Examples of the heterocyclic group as R² include a furyl, pyrrolyl, thienyl, imidazolyl or benzimidazolyl group, which may have one or more substituents on the ring.

Examples of the substituents on the ring of the aralkenyl, e.g. styryl, aromatic hydrocarbon, e.g. aryl, heterocyclic-alkyl or heterocyclic group include a lower alkyl group having 1 to 4 carbon atoms; a carboxyl group; a lower alkoxycarbonyl group having 1 to 4 carbon atoms; an acyl group such as an acetyl, benzoyl or cinnamoyl group having one or more substituents on the chain or ring; a hydroxy group which may be protected by a said protective group; a lower alkoxy group having 1 to 4 carbon atoms; a lower acyloxy, especially lower alkanoyloxy, group such as an acetoxy, propionyloxy, butyryloxy, isobutyryloxy or valeryloxy group; a fluorine, chlorine, bromine or iodine (i.e. halogen) atom; a nitro group; and an amino group which may be substituted by an acyl group such as an acetyl, benzoyl or cinnamoyl group, which may have one or more substituents on the chain or the ring, or by a lower alkyl group having 1 to 4 carbon atoms.

The acylation reaction may include a method in which a reaction between a hydroxy group of Compound C and a carboxylic acid (e.g. R²COOH) is carried out in the presence of a condensation agent, and a method in which a reaction between a hydroxy group of Compound C and a carboxylic acid anhydride (e.g. (R²CO)₂O or intramolecular R²: (CO)₂O) or a carboxylic acid halide (e.g. R²CO—Hal; Hal=a halogen atom) is carried out in the presence of a base.

Examples of carboxylic acids include an aliphatic carboxylic acid, e.g. a saturated or unsaturated aliphatic carboxylic acid, especially an alkanoic or alkenoic, more especially a lower alkanoic or lower alkenoic, acid, such as acetic acid, propionic acid, butyric acid, isobutyric acid, valeric acid, isovaleric acid, acrylic acid, methacrylic acid or crotonic acid, which may have substituents on the chain; an aromatic-unsaturated aliphatic carboxylic acid, especially having 6 to 10 ring carbon atoms in the aromatic moiety, e.g. an aralkenoic acid such as a cinnamic acid, which may have one or more substituents on the ring; an aromatic carboxylic acid, especially having 6 to 10 ring carbon atoms in the aromatic moiety, e.g. an aryl carboxylic acid, such as a benzoic acid or naphthoic acid, which may have one or more substituents on the ring; a heterocyclic-alkanoic acid, especially in which the heterocyclic moiety is a 5 to 10, more especially 5 to 9, membered ring system having at least one S, N or O heteroatom therein, such as a thiazolyl acetic acid, which may have one or more substituents on the ring; or a heterocyclic carboxylic acid, especially in which the heterocyclic moiety is a 5 to 10, more especially 5 to 9, membered ring system having at least one S, N or O heteroatom therein, such as a furan carboxylic acid, thiophene carboxylic acid, pyrrole carboxylic acid, imidazole carboxylic acid or benzimidazole carboxylic acid, which may have one or more substituents on the ring.

Examples of the substituents on the chain of the carboxylic acid include a hydroxy group which may be protected by a said protective group; and a lower alkoxycarbonyl group having 1 to 4 carbon atoms (and also a thiazolyl group in the sense earlier defined).

Examples of the substituents on the ring of the carboxylic acid include a lower alkyl group having 1 to 4 carbon atoms; a lower alkoxycarbonyl group having 1 to 4 carbon atoms; an acyl group such as an acetyl, benzoyl or cinnamoyl group, which may have one or more substituents on the chain or ring; a hydroxy group which may be protected by a said protective group; a lower alkoxy group having 1 to 4 carbon atoms; a lower acyloxy, especially lower alkanoyloxy, group such as an acetoxy, propionyloxy, butyryloxy, isobutyryloxy or valeryloxy group; a fluorine, chlorine, bromine or iodine (i.e. halogen) atom; a nitro group; or an amino group which may be substituted with an acyl group such as an acetyl, benzoyl or cinnamoyl group, which may have one or more substituents on the chain or ring, by a lower alkyl group having 1 to 4 carbon atoms, or by a protective group such as a benzyl, trityl, or benzyloxycarbonyl group.

The activated hydrogen on the heterocyclic ring may be protected by a protective group such as a benzyl, trityl or benzyloxycarbonal group (hereinafter the same type activated hydrogen protective group is applicable to the heterocyclic ring).

Any condensation agent may be used so long as it is a reagent usually used in a condensation by dehydration reaction. A carbodiimide such as N,N'-dicyclohexyl carbodiimide (hereinafter referred to as "DCC") or 1-cyclohexyl-3-(2-morpholinoethyl) carbodiimide, a 2-halopyridinium salt such as 2-chloro-1-methylpyridinium iodide or 2-bromo-1-ethylpyridinium tetrafluoroborate or 2-chloro1,3-dimethylimidazolinium chloride, may be preferably used.

The carboxylic anhydride is one corresponding to the above carboxylic acid or an intramolecular acid anhydride such as phthalic anhydride. The carboxylic halide is one corresponding to the above carboxylic acid. The halogen is preferably a chlorine or bromine atom.

Examples of the base include an aromatic amine such as pyridine, picoline, lutidine, 4-dimethylamino pyridine, 4-pyrrolidino pyridine, quinoline, isoquinoline or N,N-dimethylaniline; an aliphatic amine such as trimethyl amine, triethyl amine, diisopropyl-ethyl amine, N-methyl-pyrrolidine, N-methyl-piperidine, or N-methyl-morpholine; or an inorganic base such as sodium hydroxide, potassium hydroxide, sodium carbonate, potassium carbonate, sodium bicarbonate and potassium bicarbonate.

The solvent used in the reaction is not limited but may include aromatic hydrocarbons such as benzene, toluene or xylene; alkyl halides such as dichloromethane, chloroform or carbon tetrachloride; ethers such as diethylether, tetrahydrofuran or dioxane; inert solvents such as acetonitrile or ethyl acetate, and heterocyclic amines such as pyridine, picoline, lutidine, quinoline or isoquinoline.

The reaction may be carried out at −70° to 200° C., preferably at 0° to 100° C., with or without stirring, until the reaction is completed.

After completion of the reaction, the product is subjected to column chromatography to separate it into Compound D and the bicyclic type compound, Compound L.

Process [c]

Process [c] comprises removing oxidatively the alkoxybenzyl group of Compound D wherein $R^1$ represents an alkoxybenzyl group to obtain Compound E:

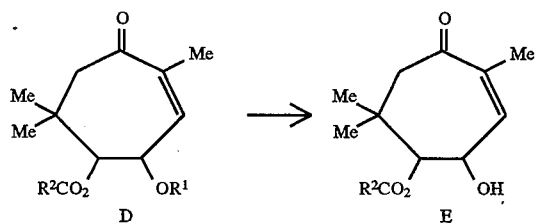

wherein per process [c] $R^1$ represents an alkoxybenzyl group and $R^2$ has the same meaning as defined above.

Examples of the alkoxybenzyl group include a p-methoxybenzyl (hereinafter referred to as "MPM") group and a 2,4-dimethoxybenzyl group.

The solvent used in the reaction includes methanol, hydrous dichloromethane and hydrous tetrahydrofuran.

Examples of the oxidizing agent include benzoquinones such as 2,3-dichloro-5,6-dicyano benzoquinone (hereinafter referred to as "DDQ").

The alkoxybenzyl group may also be removed by an acid hydrolysis reaction using hydrochloric acid, sulfuric acid, nitric acid, tritylfluoroborate, or a triarylamine cation or an electro-chemical oxidizing reaction.

The reaction may be carried out at −70° to 200° C., preferably at 0° C. to room temperature, with or without stirring, until the reaction is completed.

Process [d]

Process [d] comprises acylating Saishin N in the same manner as Process [b] (hereinafter referred to simply as "acylating") to obtain a mixture of Compound E, Compound F and Compound G. The mixture may be separated into each compound by usual separating methods such as silica gel column chromatography:

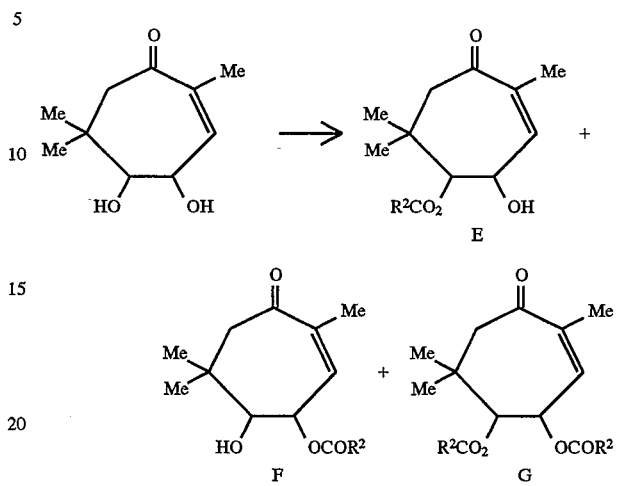

wherein per process [d] $R^2$ has the same meaning as defined above.

The reaction is carried out at −70° to 200° C., preferably at −10° to 10° C., with or without stirring, until the reaction is completed.

When the reaction is carried out by using carboxylic acid (e.g. $R^2COOH$) and carbodiimide, Compound F is obtained, i.e. in which the hydroxy group at the 4-position is selectively acylated.

Process [e]

Process [e] comprises protecting the 1-oxo group of Compound C in which in the 4-position $R^1$ is an alkoxybenzyl group, and alkylating, alkenylating, aralkenylating, aralkylating or heterocyclic-alkylating the hydroxy group in the 5-position, then deprotecting the 1-oxo group and removing the 4-position alkoxybenzyl group to obtain Compound H:

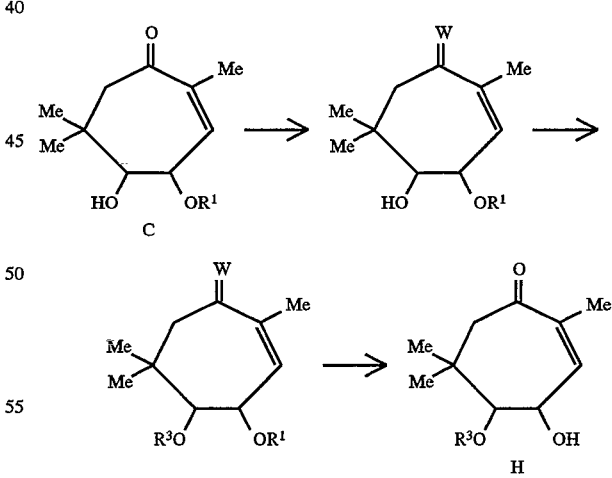

wherein per process [e] $R^1$ represents an alkoxybenzyl group, W represents an oxo protective group, and $R^3$ represents an alkyl, alkenyl, aralkenyl, aralkyl or heterocyclic-alkyl group, as more fully defined above.

Examples of the protective group of the 1-oxo group include a usual protective group of a carbonyl group, preferably a hydrazone group, and more preferably a dimethylhydrazone in a manner according to a method such as Newkome (Organic Syntheses Col. Vol. 6, p. 12).

The alkylation reaction can be carried out in the presence of an adequate base with the action of an alkyl halide. The alkenylation, aralkenylation, aralkylation and heterocyclic-alkylation reaction may be carried out in the same manner as the alkylation reaction (all per the corresponding halide, e.g. $R^3$—Hal; Hal=a halogen atom).

Examples of the base include metal alkoxides such as sodium methoxide, sodium ethoxide and potassium tert-butoxide; organic amines such as triethyl amine and diisopropyl-ethyl amine; and sodium hydride, potassium hydride, sodium amide, butyllithium and lithium diisopropylamide.

Examples of the alkyl halide include lower alkyl halides having 1 to 4 carbon atoms which may have substituents on the chain. Examples of the substituents on the chain include a protected hydroxy group, i.e. protected by a said protective group; and a lower alkoxycarbonyl group having 1 to 4 carbon atoms.

Examples of the alkenyl halide include lower alkenyl halides such as an allyl halide.

Examples of the aralkenyl halide include a cinnamyl halide which may have one or more substituents on the ring.

Examples of the aralkyl halide include benzyl halide and phenethyl halide, which may have one or more substituents on the ring.

Examples of the heterocyclic-alkyl halide include a furfuryl halide, thenyl halide or picolyl halide, which may have one or more substituents on the ring.

Examples of the substituents on the ring of the aralkenoyl, e.g. cinnamyl, aralkyl or heterocyclic-alkyl group include a lower alkyl group having 1 to 4 carbon atoms; a lower alkoxycarbonyl group having 1 to 4 carbon atoms; an acyl group such as an acetyl, benzoyl or cinnamoyl group; a hydroxy group which may be protected by a said protective group; a lower alkoxy group having 1 to 4 carbon atoms; a fluorine, chlorine, bromine or iodine (i.e. halogen) atom; or a nitro group.

The halogen in particular may be a chlorine, bromine or iodine atom.

Examples of the solvent used in the reaction include ethers such as diethyl ether, dimethoxy ethane, tetrahydrofuran and dioxane, and non-protonic polar solvents such as dimethyl formamide, dimethyl sulfoxide or hexamethyl phosphoric triamide.

The reaction may be carried out at −70° to 200° C., preferably at 0° to 100° C., with or without stirring, until the reaction is completed.

The deprotection of the oxo group and the removal of the alkoxybenzyl group may be carried out simultaneously under the conditions of the acid hydrolysis of a hydrazone compound.

Process [f]

Process [f] comprises reducing the 1-oxo group of Compound I which is obtained by substituting the 4,5-diol of Saishin N by appropriate substituents to obtain the 1-hydroxy Saishin N derivative, Compound J:

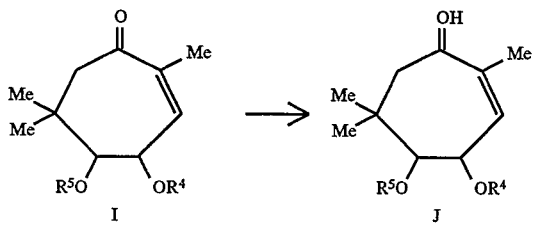

wherein per process [f] $R^4$ and $R^5$ may be the same or different or combined together, such that each represents an alkyl, alkenyl, aralkenyl, aralkyl, heterocyclic-alkyl or acyl group or a protective group, as more fully defined above, or when combined together represent a common protective group (such as a cyclic acetal).

Examples of the alkyl group include a lower alkyl group having 1 to 4 carbon atoms which may have substituents on the chain. Examples of the substituents on the chain include a hydroxy group which may be protected by a said protective group; a carboxyl group; and a lower alkoxycarbonyl group having 1 to 4 carbon atoms.

Examples of the alkenyl group include an allyl group and a 3-methyl-2-butenyl group.

Examples of the aralkenyl group include a styryl group and a cinnamyl group, which may have one or more substituents on the ring.

Examples of the aralkyl group include a benzyl group and a phenethyl group, which may have on or more substituents on the ring.

Examples of the heterocyclic-alkyl group include a furfuryl, thenyl or picolyl group, which may have one or more substituents on the ring.

Examples of the substituents on the ring of the aralkenyl, e.g. cinnamyl, aralkyl or heterocyclic-alkyl group include a lower alkyl group having 1 to 4 carbon atoms; a lower alkoxycarbonyl group having 1 to 4 carbon atoms; an acyl group such as an acetyl, benzoyl or cinnamoyl group; a hydroxy group which may be protected by a said protective group; a lower alkoxy group having 1 to 4 carbon atoms; a fluorine, chlorine, bromine or iodine (i.e. halogen) atom; or a nitro group.

Examples of the acyl group include an aliphatic acyl group, e.g. a saturated or unsaturated aliphatic acyl group, especially an alkanoyl or alkenoyl, more especially a lower alkanoyl or lower alkenoyl, group, such as an acetyl, propionyl, butyryl, isobutyryl, valeryl, acryloyl, methacryloyl or 2-butenoyl group, which may have substituents on the chain; an aromatic-unsaturated aliphatic acyl group, especially having 6 to 10 ring carbon atoms in the aromatic moiety, e.g. an aralkenoyl group such as a cinnamoyl group, which may have one or more substituents on the ring; an aromatic acyl group, especially having 6 to 10 ring carbon atoms in the aromatic moiety, e.g. an aroyl group, such as a benzoyl or naphthoyl group, which may have one or more substituents on the ring; a heterocyclic-alkanoyl group, especially in which the heterocyclic moiety is a 5 to 10, more especially 5 to 9, membered ring system having at least one S, N or O heteroatom therein, such as a thiazolyl acetyl group, which may have one or more substituents on the ring; or a heterocyclic carbonyl (acyl) group, especially in which the heterocyclic moiety is a 5 to 10, more especially 5 to 9, membered ring system having at least one S, N or O heteroatom therein, such as a furoyl, pyrrolyl carbonyl, thenoyl, imidazolyl carbonyl or benzimidazolyl carbonyl group, which may have one or more substituents on the ring.

Examples of the substituents of the chain of the acyl group include a hydroxy group which may be protected by a said protective group; a carboxyl group; and a lower alkoxycarbonyl group having 1 to 4 carbon atoms (and also a thiazolyl group in the sense earlier defined).

Examples of the substituents on the ring of the acyl group include an alkyl group having 1 to 4 carbon atoms; a carboxyl group; a lower alkoxycarbonyl group having 1 to 4 carbon atoms; an acyl group such as an acetyl, benzoyl or cinnamoyl group which may have one or more substituents on the chain or ring; a hydroxy group which may be protected by a said protective group; a lower alkoxy group having 1 to 4 carbon atoms; a lower acyloxy (especially lower alkanoyloxy) group such as an acetoxy, propionyloxy or butyryloxy group; a fluorine, chlorine, bromine or iodine (i.e. halogen) atom; a nitro group; or an amino group which may be substituted by an acyl group such as an acetyl, benzoyl or cinnamoyl group which may have one or more substituents on the chain or ring, by a lower alkyl group having 1 to 4 carbon atoms or by a benzyl, trityl or benzyloxycarbonyl group.

The common protective group is preferably a cyclic acetal and may include isopropylidene, benzylidene, or anisylidene when Saishin N is reacted directly.

Examples of the protective group of the hydroxy group in particular include a chain acetal such as a tetrahydropyranyl, tetrahydrothiopyranyl, 4-methoxy-tetrahydropyranyl, tetrahydrofuranyl, 1-ethoxyethyl, 1-methyl-1-methoxyethyl or 1-isopropyloxyethyl group, when Compound C, Compound E, Compound F or Compound H is reacted.

The cyclic acetalation reaction to provide the cyclic acetal protective group may be carried out by using a solvent which is insoluble (immiscible) with water, such as benzene, toluene, carbon tetrachloride, chloroform and dichloromethane, since the reaction is accompanied by the production of water, which is removed azeotropically in the presence of an acid catalyst.

The chain acetalation to provide the chain acetal protective group may be carried out by reacting a corresponding vinyl ether compound such as dihydropyran in the presence of an acid catalyst. The reaction may be carried out without any solvent or may be carried out by the addition of an inert solvent such as chloroform, dichloromethane, diethylether, tetrahydrofuran, dioxane, dimethylformamide, benzene or toluene.

Examples of the acid used as acid catalyst include an inorganic acid such as sulfuric acid, nitric acid, hydrobromic acid or phosphoric acid; an organic acid such as formic acid, acetic acid, propionic acid or butyric acid; a Lewis acid such as boron trifluoride etherate, titanium tetrachloride, zinc chloride or tin tetrachloride; and a sulfonic acid such as methane sulfonic acid, camphor sulfonic acid, benzene sulfonic acid and toluene sulfonic acid.

Examples of the reducing agent used for reducing the 1-oxo group include sodium borohydride, lithium borohydride or lithium aluminumhydride.

The solvent may be selected depending on the reducing agent used, i.e. when sodium borohydride is used, alcohols are preferable, and when lithium borohydride or lithium aluminumhydride is used, ethers such as diethyl ether and tetrahydrofuran are preferable.

Process [g]

Process [g] comprises treating (alcoholizing) a Saishin N derivative having a hydroxy group in the 4-position with an alcohol in the presence of an acid catalyst or alkylating, alkenylating, alkenylating, aralkylating, heterocyclic-alkylating or acylating the hydroxy group in the 4-position in the presence of a base to obtain the bicyclic type compound, Compound M:

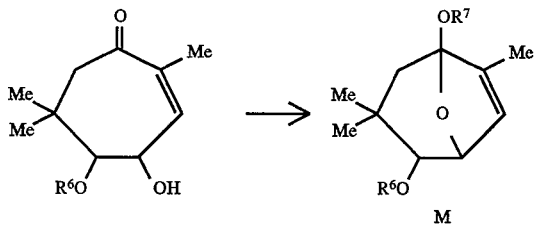

M wherein per process [g] $R^6$ and $R^7$ may be the same or different and each represents an alkyl, alkenyl, aralkenyl, aralkyl, heterocyclic-alkyl or acyl group, as more fully defined above.

Process [h]

Process [h] comprises treating a Saishin N derivative having a hydroxy group in the 5-position in the same manner as in Process [g] to obtain the bicyclic type compound, Compound N:

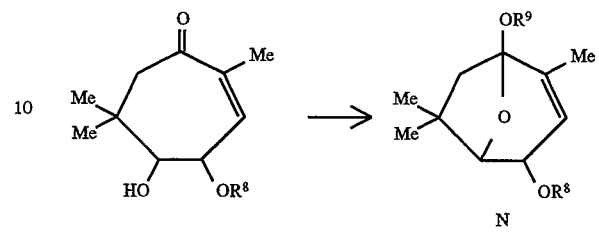

N wherein per process [h] $R^8$ and $R^9$ may be the same or different and each represents an alkyl, alkenyl, aralkenyl, aralkyl, heterocyclic-alkyl or acyl group, as more fully defined above.

The definitions of the alkyl, alkenyl, aralkenyl, aralkyl, heterocyclic-alkyl and acyl groups in Process [g] and Process [h] are more particularly as follows.

Examples of the alkyl group include a lower alkyl group having 1 to 4 carbon atoms which may have substituents on the chain. Examples of the substituents on the chain include a hydroxy group which may be protected by a said protective group; a carboxyl group; or a lower alkoxycarbonyl group having 1 to 4 carbon atoms.

Examples of the alkenyl group include an allyl group or a 3-methyl-2-butenyl group.

Examples of the aralkenyl group include a styryl group or a cinnamyl group, which may have one or more substituents on the ring.

Examples of the aralkyl group include a benzyl group or a phenethyl group, which may have one or more substituents on the ring.

Examples of the heterocyclic-alkyl group include a furfuryl, thenyl or picolyl group, which may have one or more substituents on the ring.

Examples of the substituents on the ring of the aralkenyl, e.g. cinnamyl, aralkyl or heterocyclic-alkyl group include a lower alkyl group having 1 to 4 carbon atoms; a lower alkoxycarbonyl group having 1 to 4 carbon atoms; an acyl group such as acetyl, benzoyl or cinnamoyl group; a hydroxy group which may be protected by a said protective group; a lower alkoxy group having 1 to 4 carbon atoms; a fluorine, chlorine, bromine or iodine (i.e. halogen) atom; or a nitro group.

Examples of the acyl group include an aliphatic acyl group, e.g. a saturated or unsaturated aliphatic acyl group, especially an alkanoyl or alkenoyl, more especially lower alkanoyl or lower alkenoyl, group, such as an acetyl, propionyl, butyryl, isobutyryl, valeryl, isovaleryl, acryloyl, methacryloyl or 2-butenoyl group, which may have substituents on the chain; an aromatic-unsaturated aliphatic acyl group, especially having 6 to 10 ring carbon atoms in the aromatic moiety, e.g. an aralkenoyl group such as a cinnamoyl group, which may have one or more substituents on the ring; an aromatic acyl group, especially having 6 to 10 ring carbon atoms in the aromatic moiety, e.g. an aroyl group, such as a benzoyl or naphthoyl group, which may have one or more substituents on the ring; a heterocyclic alkanoyl group, especially in which the heterocyclic moiety is a 5 to 10, more especially 5 to 9, membered ring system having at least one S, N or O heteroatom therein, such as a thiazolyl acetyl group, which may have one or more substituents on the ring; or a heterocyclic carbonyl (acyl) group, especially in which the heterocyclic moiety is a 5 to 10, more especially 5 to 9, membered ring system having at least one S, N or O heteroatom therein, such as a furoyl, pyrrolyl carbonyl, thenoyl, imidazolyl carbonyl or benzimidazolyl carbonyl group, which may have one or more substituents on the ring.

Examples of the substituents on the chain of the acyl group include a hydroxy group which may be protected by a said protective group; a carboxyl group; and a lower alkoxycarbonyl group having 1 to 4 carbon atoms (and also a thiazolyl group in the sense earlier defined).

Examples of the substituents on the ring of the acyl group include a lower alkyl group having 1 to 4 carbon atoms; a carboxyl group; a lower alkoxycarbonyl group having 1 to 4 carbon atoms; an acyl group such as an acetyl, benzoyl or cinnamoyl group which may have one or more substituents on the chain or ring; a hydroxy group which may be protected by a said protective group; a lower alkoxy group having 1 to 4 carbon atoms; a lower acyloxy (especially lower alkanoyloxy) group such as an acetoxy, propionyloxy or butyryloxy group; a fluorine, chlorine, bromine or iodine (i.e. halogen) atom; a nitro group; and an amino group which may be substituted by a protective group such as an acyl group such as an acetyl, benzoyl or cinnamoyl group which may have one or more substituents on the chain or ring, a lower alkyl group having 1 to 4 carbon atoms or a benzyl, trityl or benzyloxycarbonyl group.

The alcoholysis may be carried out as described in Process [a] (e.g. with an alcohol $R^7$—OH or $R^9$—OH), the acylation may be carried out as described in Process [b] (e.g. with an acid $R^7COOH$ or $R^9COOH$, or an acid anhydride $(R^7CO)_2O$ or $(R^9CO)_2O$ or intramolecular $R^7{:}(CO)_2O$ or $R^9{:}(CO)_2O$ or an acid halide $R^7CO$—Hal or $R^9CO$—Hal; Hal=a halogen atom), and the alkylation, alkenylation, aralkenylation, aralkylation or heterocyclic-alkylation may be carried out as described in Process [e] (e.g. with a corresponding halide $R^7$—Hal or $R^9$—Hal; Hal=a halogen atom).

When Saishin N is alcoholized, a mixture of the compounds corresponding to Compounds M and N (wherein $R^6$ or $R^8$ represents a hydrogen atom) is obtained (per Process [g] and/or [h]).

Process [i]

Process [i] comprises reducing catalytically Saishin N or the corresponding 2-cyclopentene unsaturated Saishin N derivative (Compound O) obtained in Processes [a] to [h] to obtain the 2,3-dihydro Saishin N derivative (Compound P):

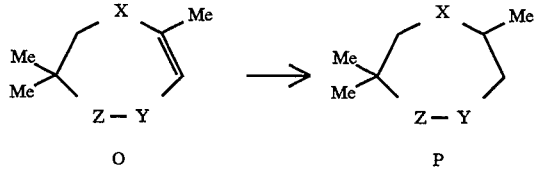

wherein per process [i] X represents a carbonyl group, a >CH—ORx group, or combines with a carbon atom in Y or Z to represent a >C(ORx)—O— group, and Y and Z may be the same or different and each represents a carbonyl group, a >CH—ORy group, or combines with an oxygen atom in X to represent a >CH— group, and the broken line represents an optional bond, while Rx and Ry have the same meanings as defined above.

Compound Q having a hydroxy group at the 5-position, and which is produced by Process [i], exists as an equilibrium mixture with the bicyclic type compound, Compound R, represented by the following formula:

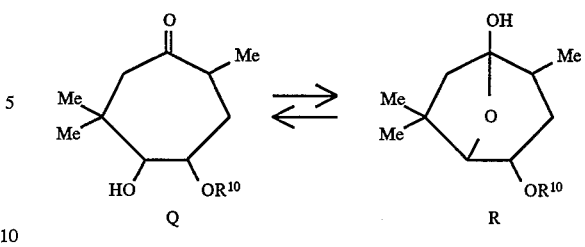

wherein per process [i] $R^{10}$ represents a hydrogen atom or an alkyl, alkenyl, aralkenyl, aralkyl, heterocyclic-alkyl or acyl group.

The definitions of the alkyl, alkenyl, aralkenyl, aralkyl, heterocyclic-alkyl and acyl groups are the same as defined above.

The solvent used in the reaction is not limited but may include an inert solvent such as aromatic hydrocarbons such as benzene, toluene or xylene, alkyl halides such as dichloromethane, chloroform or carbon tetrachloride, ethers such as diethyl ether, tetrahydrofuran or dioxane, alcohols such as methanol or ethanol, or esters such as ethyl acetate.

Any usual metal catalyst may be used as the catalyst in the catalytic hydrogenation. Platinum, palladium, Raney nickel or rhodium may be preferably used.

The reaction may be carried out with stirring at room temperature until the given amount of hydrogen is taken up.

Process [j]

Process [j] comprises treating (alcoholizing) Compound Q with an alcohol (e.g. $R^{11}$—OH) in the presence of an acid catalyst according to the procedures described in Process [h], or alkylating, alkenylating, aralkenylating, aralkylating, heterocyclic-alkylating or acylating Compound Q in the presence of a base as also described per Process [h] (e.g. with an acid $R^{11}COOH$, or with a corresponding halide $R^{11}$—Hal; Hal=a halogen atom, or with an acid anhydride $(R^{11}CO)_2O$ or intramolecular $R^{11}{:}(CO)_2O$, or an acid halide $R^{11}CO$—Hal; Hal=a halogen atom, as the case may be), to obtain the bicyclic type compound, Compound S:

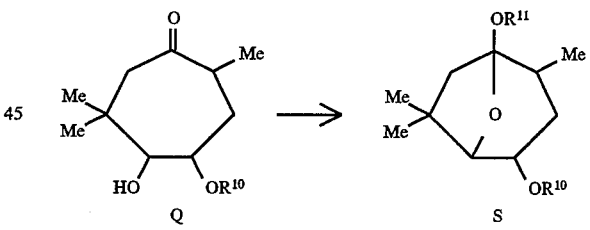

wherein per process [j] $R^{10}$ is the same as defined above and $R^{11}$ represents an alkyl, alkenyl, aralkenyl, aralkyl, heterocyclic-alkyl or acyl group.

The definitions of the alkyl, alkenyl, aralkenyl, aralkyl, heterocyclic-alkyl and acyl groups are the same as defined above for Process [h].

When the alkylation, alkenylation, aralkenylation, aralkylation, heterocyclic-alkylation or acylation of the hydroxy group, the oxidation of the hydroxy group to an oxo group, the hydrolysis of the ester group, the removal of the alkoxybenzyl group, the reduction of the oxo group to a hydroxy group, the hydrolysis of the substituents on the chain or ring, and the conversion of the substituents by a reduction and oxidizing reaction, are carried out on the Saishin N derivative obtained in Processes [a] to [j], a Saishin N derivative is obtained having desirable substituents at the 1-, 4- or 5-position.

The oxidation of a hydroxy group to an oxo group may be carried out by a usual oxidizing method of a hydroxy group.

Examples of the oxidizing agent include an activated manganese dioxide, chromic anhydride, pyridinium chlorochromate, dimethyl sulfoxide-trifluoroacetic anhydride and dimethyl sulfoxide-oxalyl chloride.

nally one hour or three hours before the administration of a mixed solution of hydrochloric acid-60% ethanol.

The results of before three hours are shown in Table 1, and those of before an hour are shown in Table 2.

TABLE 1

| Example No. | Compound | Inhibition Ratio (%) | Example No. | Compound | Inhibition Ratio (%) | Example No. | Compound | Inhibition Ratio (%) |
|---|---|---|---|---|---|---|---|---|
| 1 | AUM09 | 17 | 42 | AU208 | 39* | 77 | AU112 | 45* |
| 4 | AU154 | 21 | 43 | AU207 | 56** | 78 | AU113 | 39* |
| 7 | AU183 | 73** | 44 | AU211 | 38* | 79 | AU115 | 83* |
| 8 | AU189 | 63* | 44 | AU212 | 90** | 84 | AU144 | 51* |
| 10 | AU127 | 87** | 45 | AU215 | 56* | 95 | AU227 | 47* |
| 13 | AU128 | 53* | 45 | AU216 | 23 | 100 | AU245 | 58* |
| 16 | AU121 | 50* | 49 | AU197 | 44* | 104 | AU249 | 65** |
| 20 | AU243 | 29 | 50 | AU237 | 30 | 105 | AU508 | 82** |
| 21 | AU218 | 34 | 52 | AU219 | 60** | 106 | AU417 | 69** |
| 22 | AU407 | 82** | 53 | AU236 | 45* | 109 | AU168 | 46* |
| 23 | AU408 | 58* | 55 | AU401 | 49* | 110 | AU123A | 34 |
| 25 | AU410 | 75** | 56 | AU403 | 31 | 110 | AU123B | 25 |
| 26 | AU415 | 30 | 60 | AU241 | 37* | 116 | AU105A | 44* |
| 27 | AU507 | 63** | 60 | AU242 | 60* | 116 | AU105A | 44* |
| 29 | AU102 | 49* | 61 | AU414 | 89** | 118 | AU108A | 55* |
| 30 | AU190 | 66** | 61 | AU416 | 72** | 124 | AU194 | 23 |
| 31 | AU193 | 60** | 62 | AU501 | 56* | 125 | AU199 | 29 |
| 32 | AU133 | 38* | 63 | AU504 | 39* | 126 | AU117 | 62* |
| 33 | AU195 | 40* | 65 | AU506 | 81** | 129 | AU185 | 34 |
| 36 | AU200 | 50* | 66 | AU217 | 48* | 130 | AU187 | 35* |
| 38 | AU209 | 38 | 67 | AU225 | 36* | 131 | AU191 | 53* |
| 38 | AU210 | 26 | 70 | AU222 | 54* | 132 | AU192 | 49* |
| 40 | AU224 | 47* | 72 | AU238 | 40* | 133 | AU252 | 31 |
| 41 | AU205 | 83** | 73 | AU239 | 41* | 134 | AU250 | 36* |
| 41 | AU206 | 72** | 74 | AU223 | 49* | 135 | AU251 | 30 |
| Ref. | Saishin N | 83 (50 mg/kg)** | | | | 136 | AU163 | 32 |
| | Saishin N | 15 (20 mg/kg) | | | | | | |

*: p < 0.05, **: p < 0.01
Dose of test compound is 20 mg/kg each.

The configuration of the hydroxy group in the 1-, 4- or 5-position of Compound A may be inverted by a usual inversion method such as a Mitsunobu reaction.

The inhibitory effects of the Saishin N derivatives of the present invention on experimental ulcers will be detailed below.

Experiments on Hydrochloric acid-Ethanol-Induced Ulcers, Aspirin-Induced Ulcers, Water-Immersion stress-Induced Ulcers, Shay's Ulcers and Serotonin-Induced Ulcers were carried out by using male Wister rats weighing about 200 g in groups of six. Experiments on Ischemia-Reperfusion-Induced Gastric Lesions were carried out by using male SD rats weighing about 250 g in groups of six. The test compound was prepared by mixing polyethylene glycol and 0.5% sodium carboxymethyl cellulose solution adequately and emulsifying them sufficiently, except the Ischemia-Reperfusion-Induced Gastric Lesions Models. Activities against respective ulcer models were evaluated by an inhibiting ratio obtained by dividing the difference between the ulceration indexes of the non-administered group and the test compound group by the non-administered group.

<Hydrochloric acid-Ethanol-Induced Ulcers>

To each rat which had been fasted for 24 hours was orally administered 0.5 ml of a mixed solution of 150 mM hydrochloric acid-60% ethanol per 100 g of weight. Each rat was slaughtered after one hour, a length of ulcer which had formed at the fundus gland area of the stomach was measured and the ulceration index was calculated based on the length. The test compound was administered intraduode-

TABLE 2

| Example No. | Compound | Inhibition Ratio (%) |
|---|---|---|
| 2 | AU156 | 97 (10)** |
| 3 | AU155 | 96 (10)**; 93 (5)** |
| 4 | AU154 | 67 (10)** |
| 29 | AU102 | 75 (10)** |
| 96 | AU152 | 87 (20)** |
| 96 | AU153 | 55 (10)* |
| 97 | AU159 | 94 (5)**; 83 (10)** |
| 98 | AU157 | 64 (5)** |
| 108 | AU158 | 33 (5) |
| 116 | AU105B | 86 (10)** |
| 118 | AU108A | 75 (10)** |
| Ref. | Saishin N | 88 (20)**; 35 (10)* |

The numerals in the parentheses show the dosage (mg/kg).
*: p < 0.05, **: p < 0.01

As clearly shown in Table 1 and Table 2, the Saishin N derivatives of the present invention admittedly have a very excellent antiulcer activity.

<Aspirin-Induced Ulcers>

In each rat which had been fasted for 24 hours, the pyloric end of the stomach was ligated, and simultaneously the test compound was administered intraduodenally, and after 5 minutes, 150 mg/kg of aspirin were administered orally, respectively. After 9 hours from ligation, each rat was slaughtered, a length of ulcer which had formed at the fundus gland area of the stomach was measured and the ulceration index was calculated based on the length.

<Water-Immersion stress-Induced Ulcers>

Each rat which had been fasted for 15 hours was immobilized in a stress cage and immersed to a depth of the chest in a water bath at 21° C. Each rat was slaughtered after 10 hours, a length of ulcer which had formed at the fundus gland area of the stomach was measured and the ulceration index was calculated based on the length. The test compound was administered orally 10 minutes before the exposure to stress.

<Shay's Ulcers>

In each rat which had been fasted for 48 hours, the pyloric end of the stomach was ligated, and each was kept without being given any food or water for 14 hours. Each rat was then slaughtered, and the area of ulcer which had formed in the forestomach was measured and the ulceration index was calculated based on the area. The test compound was administered intraduodenally immediately after the ligation.

<Serotonin-Induced Ulcers>

To each rat which had been fasted for 24 hours, 30 mg/kg of a solution of serotonin creatinine sulfate in a saline solution were administered subcutaneously. Each rat was then slaughtered after four and one half hours and the area of gastric mucosal lesion which had formed facing the center line of greater curvature of the corpus ventriculi of the stomach was measured and the ulceration index was calculated based on the area. The test compound was administered intraduodenally 30 minutes before the administration of the Serotonin creatinine sulfate.

<Ischemia-Reperfusion-Induced Gastric Lesions>

Each rat which had been fasted for 24 hours was anesthetized intraperitoneally with Nembutal and immobilized on a constant temperature pad in a dorsal position. After tracheotomy was performed, a blood pressure was measured via a transducer for blood pressure from a cannula inserted in the right carotid. The abdomen was opened, and the gastroesophageal junction was ligated. A tube was then passed through the duodenostomy into the stomach and the gastric lumen was lavaged with warm saline. 1 ml of 0.1N hydrochloric acid per 100 g body weight was instilled into the stomach via the gastric tube and the pylorus was ligated. When the blood pressure became stable, 2% of the weight (w/w) of the blood was collected from a cannula inserted in the left carotid into a syringe containing a saline solution with heparin added. After 20 minutes, the collecting blood was retransfused and each rat was left to stand for 20 minutes, and slaughtered and the area of gastric mucosal lesions which had formed was measured and the ulceration index was calculated based on the area. The test compound was dissolved in dimethyl sulfoxide and administered at 40 mg/kg from the caudal artery 30 minutes before the beginning of the collection of the blood.

The results of Aspirin-Induced Ulcers, Water-immersion stress-Induced Ulcers, Shay's Ulcers, Serotonin-induced Ulcers and Ischemia-Reperfusion-Induced Gastric lesions are shown in Table 3.

TABLE 3

| Example No. | Compound | Water-immersion Stress | Shay | Aspirin | Serotonin | Ischemia-Reperfusion |
|---|---|---|---|---|---|---|
| 4 | AU154 | 17 (50) | 22 (50) | — | 46 (20)* | — |
| 22 | AU407 | 50 (50)* | — | 71 (50)** | 41 (20)* | — |
| 23 | AU408 | 56 (50)* | 43 (50)* | 73 (50)** | 44 (20)* | 75 (40)** |
| 30 | AU190 | 45 (50)* | 55 (50)* | 55 (50)* | 69 (20)** | — |
| 41 | AU205 | 42 (20)* | 50 (50)* | 53 (50)* | 80 (20)* | — |
| 44 | AU212 | 48 (20)* | 75 (50)** | 46 (20)* | 71 (20)** | 63 (40)** |
| 45 | AU215 | 45 (20)* | 73 (50)** | 66 (50)** | 81 (20)** | 90 (40)** |
| 55 | AU401 | — | — | — | 68 (20)** | — |
| 61 | AU414 | 41 (20)* | — | — | — | — |
| 62 | AU501 | 22 (50) | — | 30 (50) | 55 (50)* | 77 (40)** |
| 70 | AU222 | 34 (20)* | 58 (50)* | 28 (50) | 84 (20)** | — |
| 100 | AU245 | 38 (20)* | 35 (50) | 63 (50)** | 38 (20) | 93 (40)** |
| 104 | AU249 | 33 (20) | — | — | — | — |
| 116 | AU105B | 65 (20)** | 44 (50)* | — | 80 (20)* | 52 (40)* |
| 126 | AU117 | — | — | — | 60 (20)** | — |
| Ref. | Saishin N | 49 (50)* | 49 (100)* | 52 (50)* | 13 (20) | |
| | | 62 (100)** | 58 (300)* | 60 (100)** | 36 (50) | |
| | Cetraxate-hydrochloride | 45 (300)* | 11 (300) | 33 (300) | | |

The numerals in the parentheses show the dosage (mg/kg).
*: p < 0.05, **: p < 0.01

Considering the results from each above test, it can be clearly seen that the Saishin N derivatives of the invention have a very excellent antiulcer activity and a medicament containing such a Saishin N derivative as an effective component is an excellent antiulcer agent.

A dose of Saishin N derivative to a patient may vary depending on age, conditions, etc., but is generally 1 to 1000 mg, preferably 10 to 600 mg, per day for an adult in oral administration, and it is administered by dividing it into 1 to 6, more preferably 1 to 3, dosage portions.

According to the present invention, by admixing conventional pharmaceutical carriers with a pharmaceutically effective amount of the particular Saishin N derivative, it can be formed into solid preparations such as tablets, hard or soft capsules, granules, powder, fine particles of suppository; or into liquid preparations such as injection syrups, elixirs, suspensions or emulsions, etc. Solid preparations may be prepared in the form of enteric preparations or gradually releasing (controlled release) preparations. The pharmaceutical carriers for these preparations may be chosen suitably, depending on the desired type of preparations, from excipients, binders, disintegrants, lubricants, coating agents, dissolving adjuvants, emulsifiers, suspending agents, surfactants, absorption adjuvants, stabilizers or solvents, etc.

The present invention will hereinafter be explained in more detail with reference to the following non-limitative working Examples.

The stereochemistry of the oxygen functional group in the 1-, 4- or 5-position and the methyl group in the 2-position in a reductant of a double bond in the 2- or 3-position represents 1-cis, 2-cis, 5-trans based on the 4-position unless otherwise mentioned. When specifying a stereochemistry, the prefix is written conveniently such as 2,4-trans. The word in parentheses after a chemical name (e.g. AUM09) represents a temporary name in the specification.

EXAMPLE 1

To a solution of eucarvone-4,5-oxide, i.e. 4,5-epoxy-2,6,6-trimethyl-2-cyclohepten-1-one (50 g, 0.3M), in tetrahydrofuran (150 ml), 4-methoxybenzyl alcohol (55 g, 0.4M) and p-toluenesulfonic acid (2 g) were added, and it was heated under reflux for eight hours, concentrated, and then purified by silica gel column chromatography using hexane-ethyl acetate (10:1) as an eluent to obtain 46.7 g (50%) of 5-hydroxy-4-(4-methoxybenzyloxy)-2,6,6-trimethyl-2-cyclohepten-1-one (AUM09) as a light yellow oily product.

IR (KBr, cm$^{-1}$): 3528, 1672, 1612, 1514, 1249, 1099, 1034, 823.

1H-NMR (CDCl$_3$, ppm): 0.97 (3H, s), 1.12 (3H, s), 1.84 (3H, t, J=2 Hz), 2.33(1H, d, J=13 Hz), 2.44 (1H, d, J=13 Hz), 3.12 (1H, brs), 3.30 (1H, d, J=9 Hz), 3.82 (3H, s), 4.04 (1H, dm, J=9 Hz), 4.58 (1H, d, J=11 Hz), 4.76 (1H, d, J=11 Hz), 6.50 (1H, m), 6.91 (2H, d, J=8 Hz), 7.31 (2H, d, J=8 Hz).

EXAMPLE 2

To a solution of eucarvone-4,5-oxide (3.32 g, 20 mM) in tetrahydrofuran (10 ml), benzyl alcohol (4.12 ml, 40 mM) and concentrated sulfuric acid (0.2 ml) were added and it was stirred at 0° C. for an hour. The mixture was then treated as disclosed in Example 1 to obtain 1.09 g (20%) of 4-benzyloxy-5-hydroxy-2,6,6-trimethyl-2-cyclohepten-1-one (AU156) as a colorless oily product.

IR (KBr, cm$^{-1}$): 3534, 1672,. 1100, 1072, 738, 698.

1H-NMR (CDCl$_3$, ppm): 0.97 (3H, s), 1.12 (3H, s), 1.85 (3H, t, J=2 Hz), 2.34 (1H, d, J=12 Hz), 2.45 (1H, d, J=12 Hz), 3.09 (1H, brs), 3.34 (1H, d, J=9 Hz), 4.06 (1H, dm, J=9 Hz), 4.65 (1H, d, J=12 Hz), 4.83 (2H, d, J=12 Hz), 6.51 (1H, m), 7.36 (5H, m).

EXAMPLE 3

To a solution of eucarvone-4,5-oxide (1.66 g, 10 mM) in methanol (10 ml), concentrated sulfuric acid (0.2 ml) was added under ice-cooling and stirring was effected for 30 minutes, followed by stirring at room temperature for two hours. The reaction liquid was diluted by ethyl acetate, washed with an aqueous potassium carbonate solution and with brine, dried over magnesium sulfate, filtered and then concentrated. The residue was purified by silica gel column chromatography using hexane-ethyl acetate (20:1) as an eluent to obtain 0.99 g (46.6%) of 1,4-dimethoxy-2,6,6-trimethyl-8-oxabicyclo[3.2.1]oct-2-ene (AU155) as a colorless oily product. 1H-NMR (CDCl$_3$, ppm): 1.22 (3H, s), 1.25 (3H, s), 1.67 (3H, t, J=2 Hz), 1.80 (2H, s), 3.36 (6H, s), 3.05 (1H, dd, J=5, 2 Hz), 4.35 (1H, m), 5.48 (1H, m).

EXAMPLE 4

To a solution of eucarvone-4,5-oxide (4.98 g, 30 mM) in methanol (30 ml), p-toluenesulfonic acid (0.1 g) was added under ice-cooling and stirring was effected for three hours. The mixture was then concentrated. To the mixture was added acetone (20 ml) and 1N HCl (3 ml), and it was stirred for a day, diluted by ethyl acetate, washed with a saturated sodium bicarbonate solution and with brine, dried over magnesium sulfate, filtered and concentrated. The residue was purified by silica gel column chromatography using hexane-ethyl acetate (10:1) as an eluent to obtain 4.94 g (83%) of 5-hydroxy-4-methoxy-2,6,6-trimethyl-2-cyclohepten-1-one (AU154) as a yellow oily product.

IR (KBr, cm$^{-1}$): 3446, 1670, 1458, 1104.

1H-NMR (CDCl$_3$, ppm): 1.02 (3H, s), 1.13 (3H, s) 1.85 (3H, t, J=2 Hz), 2.35 (1H, d, J=12 Hz), 2.47 (1H, d, J=12 Hz), 3.11 (1H, brs), 3.28 (1H, d, J=9 Hz), 3.55 (3H, s), 3.79 (1H, dm, J=9 Hz), 6.43 (1H, m).

EXAMPLE 5

To a solution of 5-hydroxy-4-(4-methoxybenzyloxy)-2,6,6-trimethyl-2-cyclohepten-1-one (AUM09) (11.47 g, 37 mM) obtained in Example 1 in pyridine (30 ml), acetic anhydride (10 ml) was added and it was stirred overnight at room temperature. The reaction solution was then poured onto ice-water and extracted with ethyl acetate, washed with a saturated sodium bicarbonate and with brine, dried over magnesium sulfate, filtered and concentrated. The residue was purified by silica gel column chromatography using hexane-ethyl acetate (30:1) as an eluent to obtain 10.06 g (78%) of 5-acetoxy-4-(4-methoxybenzyloxy)-2,6,6-trimethyl-2-cyclohepten-1-one (AU181) as a colorless oily product.

IR (KBr, cm$^{-1}$): 1743, 1673, 1514, 1247, 1098, 1035, 824.

1H-NMR (CDCl$_3$, ppm): 1.02 (3H, s), 1.03 (3H, s), 1.85 (3H, t, J=2 Hz), 2.07 (3H, s), 2.45 (1H, d, J=13 Hz), 2.53 (1H, d, J=13 Hz), 3.82 (3H, s), 4.19 (1H, dm, J=9 Hz), 4.58 (1H, d, J=12 Hz), 4.65 (1H, d, J=12), 4.90 (1H, d, J=9 Hz), 6.50 (1H, m), 6.90 (2H, d, J=9 Hz), 7.25 (2H, d, J=9 Hz).

EXAMPLE 6

To a solution of 5-hydroxy-4-(4-methoxybenzyloxy)-2,6,6-trimethyl-2-cyclohepten-1-one (AUM09) (2.44 g, 8 mM) obtained in Example 1 in pyridine (10 ml), benzoic acid anhydride (3.04 g, 10 mM) and 4-dimethyl aminopyridine (0.1 g) were added and it was stirred overnight at room temperature. The mixture was then after treated according to the procedures described in Example 5 and purified by silica gel column chromatography using hexane-ethyl acetate (10:1) as an eluent to obtain 3.10 g (95%) of 5-benzoyloxy-4-(4-methoxybenzyloxy)-2,6,6-trimethyl-2-cyclohepten-1-one (AU182) as a colorless oily product.

IR (KBr, cm$^{-1}$): 1723, 1673, 1514, 1273, 1114, 712.

1H-NMR (CDCl$_3$, pm) 1.09 (3H, s), 1.13 (3H, s), 1.88 (3H, t, J=2 Hz), 2.53 (1H, d, J=13 Hz), 2.60 (1H, d, J=13 Hz), 3.75 (3H, s), 4.31 (1H, dm, J=9 Hz), 4.49 (1H, d, J=12 Hz), 4.58 (1H, d, J=12 Hz), 5.15 (1H, d, J=9 Hz), 6.54 (1H, m), 6.72 (2H, d, J=9 Hz), 7.05 (2H, d, J=9 Hz), 7.46 (2H, t, J=7 Hz), 7.59 (1H, m), 8.05 (2H, d, J=7 Hz).

EXAMPLE 7

To a solution of the product (AU182) of Example 6 (3.69 g, 9.0 mM) in methylene chloride (40 ml), water (0.8 ml) and DDQ (2.72 g, 12 mM) were added and it was stirred for two hours at room temperature, filtered and concentrated. The residue was purified by silica gel column chromatography using hexane-ethyl acetate (10:1) as an eluent and crystallized from a mixed solvent of ethyl acetate and hexane to obtain 1.82 g (70%) of 5-benzoyloxy-4-hydroxy-2,6,6-trimethyl-2-cyclohepten-1-one (AU183) as colorless needles.

Melting point: 99° to 100° C.

IR (KBr, cm$^{-1}$): 3446, 1720, 1677, 1279, 1118, 716.

1H-NMR (CDCl$_3$, ppm): 1.10 (3H, s), 1.23 (3H, s), 1.90 (3H, t, J=2 Hz), 2.49 (1H, d, J=13 Hz), 2.66 (1H, d, J=13

Hz), 4.66 (1H, m), 4.95 (1H, d, J=9 Hz), 6.55 (1H; m), 7.47 (2H, m), 7.62 (1H, m), 8.08 (2H, m).

EXAMPLE 8

The product (AU183) obtained in Example 7 (1.1 g, 3.5 mM) was acetylated by a conventional method and crystallized from a mixed solvent of ethyl acetate and hexane to obtain 0.83 g (72%) of 4-acetoxy-5-benzoyloxy-2,6,6-trimethyl-2-cyclohepten-1-one (AU189) as colorless needles. Melting point: 86° to 87° C.

IR (KBr, cm$^{-1}$): 1750, 1723,1668, 1269, 1224, 1113, 1027, 715.

1H-NMR (CDCl$_3$, ppm): 1.09 (3H, s), 1.24 (3H, s), 1.77 (3H, s), 1.90 (3H, t, J=2 Hz), 2.54 (1H, d, J=13 Hz), 2.74 (1H, d, J=13 Hz), 5.10 (1H, d, J=9 Hz), 5.97 (1H, dm, J=9 Hz), 6.36 (1H, m), 7.47 (2H, m), 7.58 (1H, m), 8.03 (2H, m).

EXAMPLE 9

5-Hydroxy-4-(4-methoxybenzyloxy)-2,6,6-trimethyl-2-cyclohepten-1-one (AUM09) (4.7 g, 15.4 mM) obtained in Example 1 was treated with 2-chlorobenzoic anhydride (16 g, 54.2 mM) according to the procedures described in Example 6 to obtain 4.33 g (63%) of 5-(2-chlorobenzoyloxy)-4-(4-methoxybenzyloxy)-2,6,6-trimethyl-2-cyclohepten-1-one (AU124) as a colorless oily product.

IR (KBr, cm$^{-1}$): 1736, 1673, 1514, 1249, 1049, 749.

1H-NMR (CDCl$_3$, ppm): 1.13 (3H, s), 1.15 (3H, s), 1.88 (3H, t, J=2 Hz), 2.52 (1H, d, J=13 Hz), 2.60 (1H, d, J=13 Hz), 3.78 (3H, s), 4.31 (1H, dm, J=8 Hz), 4.51 (1H, d, J=12 Hz), 4.61 (1H, d, J=12 Hz), 5.16 (1H, d, J=9 Hz), 6.54 (1H, m), 6.76 (2H, d, J=9 Hz), 7.12 (2H, d, J=9 Hz), 7.29 (1H, m), 7.43 (2H, m), 7.75 (1H, m).

EXAMPLE 10

The product (AU124) of Example 9 (1.5 g, 3.4 mM) was treated with DDQ as described in Example 7 and was crystallized from a mixed solvent of ethyl acetate and hexane to obtain 0.78 g (81%) of 5-(2-chlorobenzoyloxy)-4-hydroxy-2,6,6-trimethyl-2-cyclohepten-1-one (AU127) as colorless prisms. Melting point: 92.5° to 94° C.

IR (KBr, cm$^{-1}$): 3507, 1734, 1656, 1252, 1115, 1050, 748.

1H-NMR (CDCl$_3$, ppm): 1.13 (3H, s), 1.15 (3H, s), 1.89 (3H, t, J=2 Hz), 2.48 (1H, d, J=13 Hz), 2.64 (1H, d, J=13 Hz), 4.65 (1H, dm, J=9 Hz), 5.00 (1H, d, J=9 Hz), 6.54 (1H, m), 7.36 (1H, m), 7.47 (2H, m), 7.87 (1H, m).

EXAMPLE 11

5-Hydroxy-4-(4-methoxybenzyloxy)-2,6,6-trimethyl-2-cyclohepten-1-one (AUM09) (4.3 g, 14 mM) obtained in Example 1 was treated with 3-chlorobenzoic anhydride (14.4 g, 48.8 mM) according to the procedures described in Example 6 to obtain 3.56 g (57%) of 5-(3-chlorobenzoyloxy)-4-(4-methoxybenzyloxy)-2,6,6-trimethyl-2-cyclohepten-1-one (AU125) as a colorless oily product.

IR (KBr, cm$^{-1}$): 1725, 1674, 1271, 1117, 1104, 757.

1H-NMR (CDCl$_3$, ppm): 1.08 (3H, s), 1.11 (3H, s), 1.89 (3H, t, J=2 Hz), 2.51 (1H, d, J=13 Hz), 2.59 (1H, d, J=13 Hz), 3.77 (3H, s), 4.30 (1H, dm, J=9 Hz), 4.45 (1H, d, J=12 Hz), 4.60 (1H, d, J=12 Hz), 5.11 (1H, d, J=9 Hz), 6.54 (1H, m), 6.74 (2H, d, J=8 Hz), 7.05 (2H, d, J=8 Hz), 7.41 (1H, t, J=8 Hz), 7.56 (1H, m), 7.92 (1H, m), 7.97 (1H, m).

EXAMPLE 12

5-Hydroxy-4-(4-methoxybenzyloxy)-2,6,6-trimethyl-2-cyclohepten-1-one (AUM09) (5.0 g,16.4 mM) obtained in Example 1 was treated with 4-chlorobenzoic anhydride (17 g, 57.6 mM) according to the procedures described in Example 6 to obtain 3.45 g (48%) of 5-(4-chlorobenzoyloxy)-4-(4-methoxybenzyloxy)-2,6,6-trimethyl-2-cyclohepten-1-one (AU126) as a colorless oily product.

IR (KBr, cm$^{-1}$): 1725, 1674, 1271, 1117, 757.

1H-NMR (CDCl$_3$, ppm): 1.08 (3H, s), 1.11 (3H, s), 1.88 (3H, t, J=2 Hz), 2.52 (1H, d, J=13 Hz), 2.59 (1H, d, J=13 Hz), 3.77 (3H, s), 4.30 (1H, dm, J=9 Hz), 4.46 (1H, d, J=12 Hz), 4.58 (1H, d, J=12 Hz), 5.11 (1H, d, J=9 Hz), 6.53 (1H, m), 6.73 (2H, d, J=8 Hz), 7.04 (2H, d, J=8 Hz), 7.43 (2H, d, J=8 Hz), 7.95 (2H, d, J=8 Hz).

EXAMPLE 13

The product (AU126) of Example 12 (3.00 g, 6.78 mM) was treated with DDQ according to the procedures described in Example 7 and crystallized from a mixed solvent of ethyl acetate and hexane to obtain 1.09 g (48%) of 5-(4-chlorobenzoyloxy)-4-hydroxy-2,6,6-trimethyl-2-cyclohepten-1-one (AU128) as colorless plates. Melting point: 114.5° to 115.5° C.

IR (KBr, cm$^{-1}$): 3480, 1714, 1676, 1274, 1123, 1094, 848, 758.

1H-NMR (CDCl$_3$, ppm): 1.09 (3H, s), 1.21 (3H, s), 1.90 (3H, t, J=2 Hz), 2.23 (1H, d, J=8 Hz; disappeared by the addition of heavy water), 2.48 (1H, d, J=13 Hz), 2.65 (1H, d, J=13 Hz), 4.63 (1H, m; dm by the addition of heavy water, J=9 Hz), 4.92 (1H, d, J=9 Hz), 6.54 (1H, m), 7.46 (2H, d, J=9 Hz), 8.01 (2H, d, J=9 Hz).

EXAMPLE 14

The product (AU128) of Example 13 (0.79 g, 2.5 mM) was acetylated by a conventional method and crystallized from a mixed solvent of ethyl acetate and hexane to obtain 0.54 g (61%) of 4-acetoxy-5-(4-chlorobenzoyloxy)-2,6,6-trimethyl-2-cyclohepten-1-one (AU130) as colorless prisms. Melting point: 86° to 87° C.

IR (KBr, cm$^{-1}$): 1747, 1725, 1675, 1592, 1265, 760.

1H-NMR (CDCl$_3$, ppm): 1.08 (3H, s), 1.22 (3H, s), 1.79 (3H, s), 1.90 (3H, t, J=2 Hz), 2.53 (1H, d, J=13 Hz), 2.73 (1H, d, J=13 Hz), 5.09 (1H, d, J=9 Hz), 5.95 (1H, dm, J=9 Hz), 6.34 (1H, m), 7.44 (2H, d, J=9 Hz), 7.95 (2H, d, J=9 Hz).

EXAMPLE 15

5-Hydroxy-4-methoxy-2,6,6-trimethyl-2-cyclohepten-1-one (AU154) (5.18 g, 26 mM) obtained in Example 4 was acetylated by a conventional method and purified by silica gel column chromatography using benzene-ethyl acetate (20:1) as an eluent to obtain 4.16 g (65%) of 5-acetoxy-4-methoxy-2,6,6-trimethyl-2-cyclohepten-1-one (AU161) as a colorless oily product.

IR (KBr, cm$^{-1}$): 1744, 1674, 1238.

1H-NMR (CDCl$_3$, ppm): 1.02 (3H, s), 1.05 (3H, s), 1.86 (3H, t, J=2 Hz), 2.12 (3H, s), 2.46 (1H, d, J=13 Hz), 2.56 (1H, d, J=13 Hz), 3.45 (3H, s), 3.96 (1H, dm, J=9 Hz), 4.85 (1H, d, J=9 Hz), 6.45 (1H, m).

13C-NMR (CDCl$_3$, ppm): 19.0 (q), 20.9 (q), 23.6 (q), 27.3 (q), 53.9 (t), 58.6 (q), 78.6 (d), 79.3 (d), 138.4 (s), 141.8 (d), 170.2 (s), 200.3 (s).

EXAMPLE 16

5-Hydroxy-4-methoxy-2,6,6-trimethyl-2-cyclohepten-1-one (AU154) (1.0 g, 5.0 mM) obtained in Example 4 was benzoylated according to the procedures described in Example 6 and crystallized from hexane to obtain 0.95 g (63%) of 5-benzoyloxy-4-methoxy-2,6,6-trimethyl-2-cyclohepten-1-one (AU121) as colorless needles. melting point: 91.5° to 93.5° C.

IR (KBr, cm$^{-1}$): 1716, 1670, 1276, 1114, 714.

1H-NMR (CDCl$_3$, ppm): 1.10 (3H, s), 1.19 (3H, s), 1.89 (3H, t, J=2 Hz), 2.56 (1H, d, J=13 Hz), 2.64 (1H, d, J=13 Hz), 3.41 (3H, s), 4.11 (1H, dm, J=9 Hz), 5.12 (1H, d, J=9 Hz), 6.50 (1H, m), 7.47 (2H, m), 7.58 (1H, m), 8.07 (2H, m).

EXAMPLE 17

To a solution of 5-hydroxy-4-methoxy-2,6,6-trimethyl-2-cyclohepten-1-one (AU154) (1.0 g, 5.04 mM) obtained in Example 4 and triethylamine (1.06 ml, 7.06 mM) in methylene chloride (5 ml), 4-methoxybenzoyl chloride (1.3 g, 7.62 mM) was added at 0° C., and it was stirred for 30 minutes, and then stirred overnight at room temperature. The mixture was then treated according to the procedures described in Example 6 and purified by silica gel column chromatography using hexane-ethyl acetate (20:1) as an eluent and crystallized from a mixed solvent of ethyl acetate and hexane to obtain 0.53 g (32%) of 4-methoxy-5-(4-methoxybenzoyloxy)-2,6,6-trimethyl-2-cyclohepten-1-one (AU129) as colorless needles.

Melting point: 100° to 101° C.

IR (KBr, cm$^{-1}$): 1711, 1669, 1605, 1281, 1258, 1112, 852, 770.

1H-NMR (CDCl$_3$, ppm): 1.09 (3H, s), 1.17 (3H, s), 1.89 (3H, t, J=2 Hz), 2.56 (1H, d, J=13 Hz), 2.62 (1H, d, J=13 Hz), 3.40 (3H, s), 3.87 (3H, s), 4.08 (1H, dm, J=9 Hz), 5.09 (1H, d, J=9 Hz), 6.49 (1H, m), 6.94 (2H, d, J=9 Hz), 8.02 (2H, d, J=9 Hz).

EXAMPLE 18

5-Hydroxy-4-methoxy-2,6,6-trimethyl-2-cyclohepten-1-one (AU154) (9.9 g, 50 mM) obtained in Example 4 was treated with 4-nitrobenzoyl chloride according to the procedures described in Example 17 and fractionated by silica gel column chromatography using hexane-ethyl acetate (20:1 to 10:1) as an eluent. The first eluted portion was crystallized from ethyl acetate-hexane to obtain 5.75 g (33%) of 4-methoxy-1-(4-nitrobenzoyloxy)-2,6,6-trimethyl-8-oxabicyclo[3.2.1]oct-2-ene (AU231) as light yellow needles.

Melting point: 95.0° to 95.5° C.

IR (KBr, cm$^{-1}$): 1749, 1527, 1261, 1141, 715.

1H-NMR (CDCl$_3$, ppm): 1.30 (3H, s), 1.34 (3H, s), 1.67 (3H, t, J=2 Hz), 2.19 (2H, s), 3.40 (3H, s), 4.24 (1H, dd, J=5, 2 Hz), 4.54 (1H, m), 5.52 (1H, m), 8.22 (2H, d, J=9 Hz), 8.30 (2H, d, J=9 Hz).

Further, the successive eluted portion was crystallized from ethyl acetate-hexane to obtain 3.90 g (22%) of 4-methoxy-5-(4-nitrobenzoyloxy)-2,6,6-trimethyl-2-cyclohepten-1-one (AU230) as light yellow needles. Melting point: 122° to 123° C.

IR (KBr, cm$^{-1}$): 1728, 1670, 1522, 1269, 1114, 714.

1H-NMR (CDCl$_3$, ppm): 1.11 (3H, s), 1.20 (3H, s), 1.90 (3H, t, J=2 Hz), 2.57 (1H, d, J=13 Hz), 2.64 (1H, d, J=13 Hz), 3.40 (3H, s), 4.12 (1H, dm, J=9 Hz), 5.12 (1H, d, J=9 Hz), 6.50 (1H, m), 8.23 (2H, d, J=9 Hz), 8.33 (2H, d, J=9 Hz).

EXAMPLE 19

The mixture of 4-methoxy-5-(4-nitrobenzoyloxy)-2,6,6-trimethyl-2-cyclohepten-1-one (AU230) (2.78 g, 8 mM) obtained in Example 18, ammonium chloride (0.17 g), Fe (1.2 g), dimethylformamide (9 ml) and water (4 ml) was stirred for 20 minutes at 80° C., filtered and washed with ethyl acetate. The filtrate and the wash liquid were combined and washed with water, dried over magnesium sulfate, filtered and crystallized from a mixed solution of ethyl acetate and hexane to obtain 2.29 g (90%) of 5-(4-aminobenzoyloxy)-4-methoxy-2,6,6-trimethyl-2-cyclohepten-1-one (AU235) as colorless needles.

Melting point: 138.5° to 161° C.

IR (KBr, cm$^{-1}$): 3432, 3349, 3238, 1684, 1664, 1602, 1275, 1168, 1115.

1H-NMR (CDCl$_3$, ppm): 1.08 (3H, s), 1.16 (3H, s), 1.88 (3H, t, J=2 Hz), 2.56 (1H, d, J=13 Hz), 2.61 (1H, d, J=13 Hz), 3.41 (3H, s), 4.11 (3H, m), 5.08 (1H, d, J=9 Hz), 6.50 (1H, m), 6.66 (2H, d, J=9 Hz), 7.88 (2H, d, J=9 Hz).

EXAMPLE 20

To a mixed solution of 5-hydroxy-4-methoxy-2,6,6-trimethyl-2-cyclohepten-1-one (AU154) (0.99 g, 5 mM) obtained in Example 4 in acetonitrile (15 ml) and pyridine (4 ml), 2-tritylaminothiazole-4-acetic acid (2.6 g, 6.5 mM), DCC (1.34 g, 6.5 mM) and dimethyl aminopyridine (0.1 g) were added under ice-cooling and stirring, and stirred overnight. The reaction solution was filtered and the filtrate was concentrated. The residue was diluted with ethyl acetate and washed successively with water, a sodium bicarbonate solution and brine, dried over magnesium sulfate, filtered, and concentrated. The residue was purified by silica gel column chromatography using hexane-ethyl acetate (5:1) to obtain 1.31 g of the intermediate 4-methoxy-5-(2-tritylaminothiazol-4-yl)acetoxy-2,6,6-trimethyl-2-cyclohepten-1-one as a colorless oily product.

1H-NMR (CDCl$_3$, ppm): 0.97 (6H, s), 1.84 (3H, t, J=2 Hz), 2.45 (1H, d, J=13 Hz), 2.52 (1H, d, J=2 Hz), 3.35 (3H, s), 3.60 (2H, s), 3.93 (1H, dm, J=9 Hz), 4.85 (1H, d, J=9 Hz), 6.20 (1H, s), 6.43) (1H, m), 6.68 (1H, brs), 7.29 (15H, m).

To the intermediate product so obtained was added 80% acetic acid (5 ml), and the mixture was warmed to 70° C. for three hours and concentrated. The residue was purified by silica gel column chromatography using hexane-ethyl acetate (1:1) as an eluent and purified from a mixed solvent of ethyl acetate and hexane to obtain 0.40 g (23%) of 5-(2-aminothiazol-4-yl)acetoxy-4-methoxy-2,6,6-trimethyl-2-cyclohepten-1-one (AU243) as yellow plates. Melting point: 116° to 117° C.

IR (KBr, cm$^{-1}$): 3376, 3296, 3127, 1733, 1660, 1532, 1262.

1H-NMR (CDCl$_3$, ppm): 0.99 (6H, s), 1.85 (3H, t, J=2 Hz), 2.45 (1H, d, J=13 Hz), 2.53 (1H, d, J=13 Hz), 3.40 (3H, s), 3.61 (2H, s), 3.95 (1H, dm, J=9 Hz), 4.86 (1H, d, J=9 Hz), 5.49 (2H, brs), 6.35 (1H, s), 6.44 (1H, m).

EXAMPLE 21

To a solution of 5-hydroxy-4-methoxy-2,6,6-trimethyl-2-cyclohepten-1-one (AU154) obtained in Example 4 (1.98 g, 10 mM) in pyridine (10 ml), phthalic anhydride (1.78 g, 12 mM) and dimethyl aminopyridine (0.05 g) were added and warmed to 90° C. for three hours, left to cool, poured onto ice-water, alkalified with potassium carbonate and extracted with ethyl acetate. The aqueous layer was acidified with hydrochloric acid and extracted with ethyl acetate, washed with brine, dried over magnesium sulfate, filtered, and concentrated. The residue was crystallized from a mixed solvent of ethyl acetate and hexane to obtain 1.80 g (53%)

of 5-(2-carboxybenzoyloxy)-4-methoxy-2,6,6-trimethyl-2-cyclohepten-1-one (AU218) as colorless plates. Melting point: 158.0° to 158.5° C.

IR (KBr, cm$^{-1}$): 3600–2300, 1726, 1694, 1672, 1294, 748.

1H-NMR (CDCl$_3$, ppm): 1.11 (3H, s) 1.15 (3H, s), 1.88 (3H, t, J=2 Hz), 2.53 (1H, d, J=13 Hz), 2.61 (1H, d, J=13 Hz), 3.45 (3H, s), 4.09 (1H, dm, J=9 Hz), 5.12 (1H, d, J=9 Hz), 6.51 (1H, m), 7.61 (2H, m), 7.75 (1H, m), 7.90 (1H, m).

EXAMPLE 22

5-Hydroxy-4-methoxy-2,6,6-trimethyl-2-cyclohepten-1-one (AU154) obtained in Example 4 (5.95 g, 30 mM) was treated with 2,4-dinitrobenzoic acid according to the procedures described in Example 20. The mixture was re-crystallized twice from a mixed solution of ethyl acetate and hexane to obtain 7.24 g (61.5%) of 5-(2,4-dinitrobenzoyloxy)-4-methoxy-2,6,6-trimethyl-2-cyclohepten-1-one (AU407) as reddish needles. Melting point: 147.5° to 149° C.

IR (KBr, cm$^{-1}$): 1741, 1669, 1541, 1348, 1284, 1101, 735.

1H-NMR (CDCl$_3$, ppm): 1.06 (3H, s), 1.17 (3H, s), 1.90 (3H, t, J=2 Hz), 2.51 (1H, d, J=13 Hz), 2.59 (1H, d, J=13 Hz), 3.45 (3H, s), 4.06 (1H, dm, J=9 Hz), 5.10 (1H, d, J=9 Hz), 6.49 (1H, m), 7.99 (1H, d, J=8 Hz), 8.55 (1H, dd, J=8, 2 Hz), 8.78 (1H, d, J=8 Hz).

EXAMPLE 23

The product (AU407) of Example 22 (5.0 g, 12.7 mM) was reduced at the nitro groups according to the procedure described in Example 19 to obtain 2.27 g (55.4%) of 5-(2,4-diaminobenzoyloxy)-4-methoxy-2,6,6-trimethyl-2-cyclohepten-1-one (AU408) as yellow plates.

Melting point: 178° to 179° C.

IR (KBr, cm$^{-1}$): 3498, 3451, 3366, 1665, 1624, 1585, 1542, 1258, 1148, 770.

1H-NMR (CDCl$_3$, ppm): 1.07 (3H, s), 1.16 (3H, s), 1.87 (3H, t, J=2 Hz), 2.52 (1H, d, J=13 Hz), 2.61 (1H, d, J=13 Hz), 3.43 (3H, s), 3.92 (2H, brs; disappeared by the addition of heavy water), 4.06 (1H, dm, J=9 Hz), 5.02 (1H, d, J=9 Hz), 5.74 (2H, brs; disappeared by the addition of heavy water), 5.87 (1H, d, J=2 Hz), 5.99 (1H, dd, J=9, 2 Hz), 6.52 (1H, m), 7.69 (1H, d, J=9 Hz).

The above product (AU408) so obtained (1.3 g, 4.0 mM) was dissolved in ethyl acetate and treated with a solution of 4N hydrogen chloride in ethyl acetate. The resulting precipitate was collected by filtration to obtain 1.5 g (95%) of a hydrochloride thereof (AU408 hydrochloride) as a colorless powder. Melting point: 115° C. (decomposition).

IR (KBr, cm$^{-1}$): 3450, 3326, 3200–2400, 1673, 1634, 1247, 1109, 769.

1H-NMR (DMSO-d$_6$, ppm): 0.92 (3H, s), 1.09 (3H, s), 1.79 (3H, brt), 2.39 (1H, d, J=13 Hz), 2.73 (1H, d, J=13 Hz), 3.33 (3H, s), 4.29 (1H, brm), 4.79 (1H, d, J=9 Hz), 6.29 (1H, m), 6.40 (1H, m), 6.58 (1H, m), 7.71 (1H, m).

EXAMPLE 24

5-Hydroxy-4-methoxy-2,6,6-trimethyl-2-cyclohepten-1-one (AU154) obtained in Example 4 (25.0 g, 126 mM) was treated with 3,4-dinitrobenzoic acid according to the procedures described in Example 20, and crystallized from methanol to obtain 42.1 g (85%) of 5-(3,4-dinitrobenzoyloxy)-4-methoxy-2,6,6-trimethyl-2-cyclohepten-1-one (AU409) as light yellow needles. Melting point: 103° to 104° C.

IR (KBr, cm$^{-1}$): 1734, 1668, 1545, 1369, 1354, 1251, 847.

1H-NMR (CDCl$_3$, ppm): 1.10 (3H, s), 1.19 (3H, s), 1.91 (3H, t, J=2 Hz), 2.56 (1H, d, J=13 Hz), 2.65 (1H, d, J=9 Hz), 3.40 (3H, s), 4.13 (1H, dm, J=9 Hz), 5.11 (1H, d, J=9 Hz), 6.49 (1H, m), 8.01 (1H, d, J=9 Hz), 8.43 (1H, dd, J=9, 2 Hz), 8.57 (1H, d, J=2 Hz).

EXAMPLE 25

The product (AU409) of Example 24 (22 g, 56 mM) was reduced at the nitro groups according to the procedures described in Example 19 and crystallized from methanol to obtain 2.95 g (16%) of 5-(3,4-diaminobenzoyloxy)-4-methoxy-2,6,6-trimethyl-2-cyclohepten-1-one (AU410) as light red needles. Melting point: 136° C. (decomposition).

IR (KBr, cm$^{-1}$): 3472, 3362, 1684, 1662, 1310, 1288, 1224, 764.

1H-NMR (CDCl$_3$, ppm): 1.07 (3H, s), 1.16 (3H, s), 1.88 (3H, t, J=2 Hz), 2.55 (1H, d, J=13 Hz), 2.63 (1H, d, J=13 Hz), 3.41 (3H, s), 4.09 (1H, dm, J=9 Hz), 5.08 (1H, d, J=9 Hz), 5.50 (1H, m), 6.69 (1H, d, J=8 Hz), 7.43 (1H, d, J=2 Hz), 7.50 (1H, dd, J=8, 2 Hz).

EXAMPLE 26

To a solution of the product (AU410) of Example 25 (1.44 g, 4.77 mM) in tetrahydrofuran (10 ml), cyanogen bromide (0.47 g, 4.78 mM) was added at room temperature under stirring and after five hours, cyanogen bromide (0.26 g, 2.60 mM) was further added and stirred overnight. The reaction mixture was treated with a saturated sodium bicarbonate solution and extracted with ethyl acetate and reverse extracted with diluted hydrochloric acid. The extracted solution was treated with sodium bicarbonate to basify, extracted with ethyl acetate, dried over magnesium sulfate, filtered, and concentrated to obtain 1.21 g (76%) of 5-(2-aminobenzimidazolyl-5-carbonyloxy)-4-methoxy-2,6,6-trimethyl-2-cyclohepten-1-one (AU415) as a glassy material. Melting point: 131° to 132.5° C.

IR (KBr, cm$^{-1}$): 3400–3100, 1709, 1646, 1559, 1289, 1198.

1H-NMR (CDCl$_3$, ppm): 1.08 (3H, s), 1.19 (3H, s), 1.86 (3H, t, J=2 Hz), 2.54 (1H, d, J=13 Hz), 2.62 (1H, d, J=13 Hz), 3.41 (3H, s), 4.12 (1H, dm, J=9 Hz), 5.09 (1H, d, J=9 Hz), 5.51 (2H, br; disappeared by the addition of heavy water), 6.47 (1H, m), 7.29 (1H, d, J=8 Hz), 7.82 (1H, d, J=8 Hz), 7.98 (1H, brs).

EXAMPLE 27

The product (AU410) of Example 25 (1 g, 3 mM) was added to dimethylformamide dimethylacetal (1.5 ml) and was stirred at 50° C. for one hour. The reaction solution was concentrated, the residue was purified by silica gel column chromatography using ethyl acetate-hexane (3:1) as an eluent and crystallized from a mixed solution of ethyl acetate and hexane to obtain 0.1 g (10%) of 5-(5-benzimidazolylcarbonyloxy)-4-methoxy-2,6,6-trimethyl-2-cyclohepten-1-one (AU507) as a brown glassy product. Melting point: 155° to 157° C.

IR (KBr, cm$^{-1}$): 3600–3100, 1705, 1654, 1302, 1124, 750.

1H-NMR (CDCl$_3$, ppm): 1.11 (3H, s), 1.22 (3H, s), 1.89 (3H, t, J=2 Hz), 2.56 (1H, d, J=13 Hz), 2.66 (1H, d, J=13 Hz), 3.41 (3H, s), 4.13 (1H, dm, J=9 Hz), 5.14 (1H, d, J=9 Hz), 6.52 (1H, m), 7.69 (1H, d, J=8 Hz), 8.05 (1H, d, J=8 Hz), 8.23 (1H, s), 8.47 (1H, s).

EXAMPLE 28

4-Benzyloxy-5-hydroxy-2,6,6-trimethyl-2-cyclohepten-1-one (AU156) obtained in Example 2 (50 mg, 0.18 mM)

was acetylated by a conventional method to obtain 49 mg (91%) of 5-acetoxy-4-benzyloxy-2,6,6-trimethyl-2-cyclohepten-1-one (AU156 acetate) as a colorless oily product.

1H-NMR (CDCl$_3$, ppm): 1.01 (3H, s), 1.02 (3H, s), 1.84 (3H, t, J=2 Hz), 2.04 (3H, s), 2.43 (1H, d, J=13 Hz), 2.53 (2H, d, J=13 Hz), 4.20 (1H, dm, J=9 Hz), 4.63 (1H, d, J=12 Hz), 4.71 (2H, d, J=12 Hz), 4.91 (1H, d, J=9 Hz), 6.52 (1H, m), 7.31 (5H, m).

EXAMPLE 29

Saishin N (5.53 g, 30 mM) was acetylated by a conventional method and re-crystallized from a mixed solvent of ethyl acetate and hexane to obtain 6.58 g (81%) of 4,5-diacetoxy-2,6,6-trimethyl-2-cyclohepten-1-one (AU102) as colorless needles. Melting point: 68° to 69° C.

IR (KBr, cm$^{-1}$): 1741, 1681, 1252, 1041.

1H-NMR (CDCl$_3$, ppm): 1.02 (3H, s), 1.09 (3H, s), 1.86 (3H, t, J=2 Hz), 2.09 (3H, s), 2.10 (3H, s), 2.48 (1H, d, J=13 Hz), 2.66 (1H, d, J=13 Hz), 4.89 (1H, d, J=9 Hz), 5.75 (1H, dm, J=9 Hz), 6.26 (1H, m).

EXAMPLE 30

Saishin N (1.84 g, 10 mM) was benzoylated according to the procedures described in Example 6 and fractionated by silica gel column chromatography using hexane-ethyl acetate (10:1) as an eluent. The first eluted portion was crystallized from a mixed solvent of ethyl acetate and hexane to obtain 0.98 g (34.1%) of 4-benzoyloxy-5-hydroxy-2,6,6-trimethyl-2-cyclohepten-1-one (AU190) as colorless plates. Melting point: 127° to 128° C.

IR (KBr, cm$^{-1}$): 3551, 1718, 1674, 1333, 1272, 1111, 705.

1H-NMR (CDCl$_3$+D$_2$O, ppm): 1.12 (3H, s), 1.16 (3H, s), 1.87 (3H, t, J=2 Hz), 2.45 (1H, d, J=13 Hz), 2.67 (1H, d, J=13 Hz), 3.55 (1H, d, J=9 Hz), 5.85 (1H, dm, J=9 Hz), 6.42 (1H, m), 7.48 (2H, m), 7.61 (1H, m), 8.09 (2H, m).

0.7 g (26%) of 5-benzoyloxy-4-hydroxy-2,6,6-trimethyl-2-cyclohepten-1-one (AU183) as that in Example 7 was obtained (per acyl transfer reaction) from the successive eluted portion.

EXAMPLE 31

4-Benzoyloxy-5-hydroxy-2,6,6-trimethyl-2-cyclohepten-1-one (AU190) obtained in Example 30 (0.60 g, 2.08 mM) was acetylated by a conventional method and crystallized from water to obtain 0.47 g (67%) of 5-acetoxy-4-benzoyloxy-2,6,6-trimethyl-2-cyclohepten-1-one (AU193) as colorless crystals. Melting point: 94° to 95° C.

IR (KBr, cm$^{-1}$): 1735, 1722, 1672, 1273, 1232, 714.

1H-NMR (CDCl$_3$, ppm): 1.06 (3H, s), 1.15 (3H, s), 1.82 (3H, s), 1.90 (3H, t, J=2 Hz), 2.52 (1H, d, J=13 Hz), 2.73 (1H, d, J=13 Hz), 5.03 (1H, d, J=9 Hz), 6.04 (1H, dm, J=9 Hz), 6.41 (1H, m), 7.47 (2H, brt, J=7 Hz), 7.59 (1H, brt, J=7 Hz), 8.04 (2H, brd, J=7 Hz).

EXAMPLE 32

Saishin N (1.84 g, 10 mM) was treated with 3,4-dimethoxybenzoyl chloride (2.41 g, 12 mM) according to the procedures described in Example 17 and fractionated by silica gel column chromatography using benzene-ethyl acetate (5:1) as an eluent. The first eluted portion was crystallized from a mixed solution of ethyl acetate and hexane to obtain 1.01 g (32%) of 4-(3,4-dimethoxybenzoyloxy)-5-hydroxy-2,6,6-trimethyl-2-cyclohepten-1-one (AU133) as colorless plates. Melting point: 161° to 163.5° C.

IR (KBr, cm$^{-1}$): 3517, 1719, 1680, 1517, 1271, 1215, 758.

1H-NMR (CDCl$_3$+D$_2$O, ppm): 1.13 (3H, s), 1.17 (3H, s), 1.89 (3H, t, J=2 Hz), 2.46 (1H, d, J=13 Hz), 2.67 (1H, d, J=13 Hz), 3.54 (1H, d, J=9 Hz), 3.95 (3H, s), 3.96 (3H, s), 5.84 (1H, dm, J=9 Hz), 6.44 (1H, m), 6.92 (1H, d, J=8 Hz), 7.58 (1H, d, J=2 Hz), 7.74 (1H, dd, J=8, 2 Hz).

The successive eluted portion was crystallized from a mixed solvent of ethyl acetate and ethanol to obtain (per acyl transfer reaction) 0.87 g (28%) of 5-(3,4-dimethoxybenzoyloxy)-4-hydroxy-2,6,6-trimethyl-2-cyclohepten-1-one (AU134) as colorless plates.

Melting point: 150° to 151.5° C.

IR (KBr, cm$^{-1}$): 3485, 1707, 1669, 1598, 1518, 1279, 1224, 762.

1H-NMR (CDCl$_3$+D$_2$O, ppm): 1.09 (3H, s), 1.21 (3H, s), 1.90 (3H, t, J=2 Hz), 2.48 (1H, d, J=13 Hz), 2.65 (1H, d, J=13 Hz), 3.94 (3H, s), 3.95 (3H, s), 4.63 (1H, dm, J=9 Hz), 4.91 (1H, d, J=9 Hz), 6.55 (1H, m), 6.92 (1H, d, J=8 Hz), 7.57 (1H, d, J=2 Hz), 7.72 (1H, dd, J=8, 2 Hz).

EXAMPLE 33

Saishin N (3.68 g, 20 mM) was treated with 4-methoxybenzoylchloride (4.27 g, 25 mM) as described in Example 17 and fractionated by silica gel column chromatography using hexane-ethyl acetate (10:1) as an eluent. The first eluted portion was crystallized from a mixed solvent of ethyl acetate and hexane to obtain 2.44 g (38%) of 5-hydroxy-4-(4-methoxybenzoyloxy)-2,6,6-trimethyl-2-cyclohepten-1-one (AU195) as colorless plates. Melting point: 108.5° to 110° C.

IR (KBr, cm$^{-1}$): 3517, 1682, 1608, 1342, 1290, 1182, 1106, 774.

1H-NMR (CDCl$_3$, ppm): 1.12 (3H, s), 1.17 (3H, s), 1.88 (3H, t, J=2 Hz), 2.45 (1H, d, J=13 Hz), 2.67 (1H, d, J=13 Hz), 3.55 (1H, dd, J=9, 6 Hz), 3.89 (3H, s), 5.83 (1H, dm, J=9 Hz), 6.43 (1H, m), 6.96 (2H, d, J=9 Hz), 8.06 (2H, d, J=9 Hz).

1.63 g (25%) of 4-hydroxy-5-(4-methoxybenzoyloxy)-2,6,6-trimethyl-2-cyclohepten-1-one (AU202) were obtained (per acyl transfer reaction) as a light yellow oily product from the successive eluted portion.

IR (KBr, cm$^{-1}$): 3474, 1716, 1671, 1605, 1258, 1169, 1102, 768.

1H-NMR (CDCl$_3$+D$_2$O, ppm): 1.07 (3H, s), 1.19 (3H, s), 1.88 (3H, t, J=2 Hz), 2.46 (1H, d, J=13 Hz), 2.63 (1H, d, J=13 Hz), 3.87 (3H, s), 4.61 (1H, dm, J=9 Hz), 4.89 (1H, d, J=9 Hz), 6.54 (1H, m), 6.94 (2H, d, J=9 Hz), 8.02 (2H, d, J=9 Hz).

EXAMPLE 34

5-Hydroxy-4-(4-methoxybenzoyloxy)-2,6,6-trimethyl-2-cyclohepten-1-one (AU195) (796 mg, 2.5 mM) obtained in Example 33 was acetylated by a conventional method and crystallized from water to obtain 867 mg (96%) of 5-acetoxy-4-(4-methoxybenzoyloxy)-2,6,6-trimethyl-2-cyclohepten-1-one (AU198) as colorless plates. Melting point: 93° to 94° C.

IR (KBr, cm$^{-1}$): 1749, 1719, 1673, 1605, 1256, 770.1H-NMR (CDCl$_3$, ppm) 1.04 (3H, s), 1.14 (3H, s), 1.81 (3H, s), 1.88 (3H, t, J=2 Hz), 2.51 (1H, d, J=13 Hz), 2.72 (1H, d, J=13 Hz), 3.87 (3H, s), 4.99 (1H, d, J=9 Hz), 6.01 (1H, dm, J=9 Hz), 6.41 (1H, m), 6.94 (2H, d, J=9 Hz), 7.98 (2H, d, J=9 Hz).

EXAMPLE 35

4-Hydroxy-5-(4-methoxybenzoyloxy)-2,6,6-trimethyl-2-cyclohepten-1-one (AU202) (1.46 g, 4.5 mM) obtained in Example 33 was acetylated by a conventional method and crystallized from a mixed solvent of ethyl acetate and hexane to obtain 0.91 g (56%) of 4-acetoxy-5-(4-methoxybenzoyloxy)-2,6,6-trimethyl-2-cyclohepten-1-one (AU203) as colorless prisms. Melting point: 78° to 80° C.

IR (KBr, cm$^{-1}$): 1762, 1715, 1672, 1604, 1259, 1214, 1176, 1101, 1031, 850, 768.

1H-NMR (CDCl$_3$, ppm): 1.08 (3H, s), 1.23 (3H, s), 1.78 (3H, s), 1.89 (3H, t, J=2 Hz), 2.52 (1H, d, J=13 Hz), 2.73 (1H, d, J=13 Hz), 3.87 (3H, s), 5.07 (1H, d, J=9 Hz), 5.97 (1H, dm, J=9 Hz), 6.36 (1H, m), 6.94 (2H, d, J=9 Hz), 7.98 (2H, d, J=9 Hz).

EXAMPLE 36

Saishin N (3.68 g, 20 mM) was treated with 3-nitrobenzoyl chloride (4.45 g, 24 mM) as described in Example 17 and purified by silica gel column chromatography using hexane-ethyl acetate (5:1) as an eluent and crystallized from a mixed solvent of ethyl acetate and hexane to obtain 1.79 g (24% of 5-hydroxy-4-(3-nitrobenzoyloxy-2,6,6-trimethyl-2-cyclohepten-1-one (AU200) as colorless prisms.

Melting point: 131° to 133° C.

IR (KBr, cm$^{-1}$): 3517, 1718, 1668, 1534, 1355, 1288, 1268, 1144, 719.

1H-NMR (CDCl$_3$+D$_2$O, ppm): 1.14 (3H, s), 1.17 (3H, s), 1.90 (3H, t, J=2 Hz), 2.48 (1H, d, J=13 Hz), 2.68 (1H, d, J=13 Hz), 3.57 (1H, d, J=9 Hz), 5.93 (1H, dm, J=9 Hz), 6.45 (1H, m), 7.71 (1H, t, J=8 Hz), 8.46 (2H, m), 8.91 (1H, t, J=2 Hz).

EXAMPLE 37

The product (AU200) of Example 36 (750 mg, 2.8 mM) was acetylated by a conventional method and crystallized from a mixed solvent of ethyl acetate and hexane to obtain 733 mg (83%) of 5-acetoxy-4-(3-nitrobenzoyloxy)-2,6,6-trimethyl-2-cyclohepten-1-one (AU204) as colorless needles. Melting point: 108.5° to 110° C.

IR (KBr, cm$^{-1}$): 1742, 1666, 1538, 1350, 1263, 1133, 714.

1H-NMR (CDCl$_3$, ppm): 1.07 (3H, s), 1.16 (3H, s), 1.87 (3H, s), 1.91 (3H, t, J=2 Hz), 2.56 (1H, d, J=13 Hz), 2.73 (1H, d, J=13 Hz), 5.07 (1H, d, J=9 Hz), 6.03 (1H, dm, J=9 Hz), 6.38 (1H, m), 7.70 (1H, t, J=8 Hz), 8.35 (1H, m), 8.47 (1H, m), 8.88 (1H, m).

EXAMPLE 38

To a solution of 5-hydroxy-4-(3-nitrobenzoyloxy)-2,6,6-trimethyl-2-cyclohepten-1-one (AU200) (3.03 g, 8 mM) obtained in Example 36 in benzene (200 ml), activated iron (13 g) was added and ethanol (2.2 ml) was added and it was heated under reflux. The mixture was further treated with water (0.5 ml) little by little and heated under reflux for four hours and filtered. The filtrate was then concentrated and the residue was fractionated by silica gel column chromatography using hexane-ethyl acetate (2:1) as an eluent. From the first eluted portion 1.27 g (52%) of 4-(3-aminobenzoyloxy)-5-hydroxy-2,6,6-trimethyl-2-cyclohepten-1-one (AU210) was obtained as a yellow oily product.

IR (KBr, cm$^{-1}$): 3450, 3375, 1718, 1670, 1291, 1234, 752.

1H-NMR (CDCl$_3$, ppm): 1.11 (3H, s), 1.15 (3H, s), 1.87 (3H, s), 2.35 (1H, br), 2.44 (1H, d, J=13 Hz), 2.66 (1H, d, J=13 Hz) 3.53 (1H, d, J=9 Hz), 3.85 (2H, br), 5.82 (1H, dm, J=9 Hz), 6.40 (1H, m), 6.90 (1H, m), 7.24 (1H, m), 7.38 (1H, m), 7.46 (1H, m).

The successive eluded portion was crystallized from a mixed solvent of ethyl acetate and hexane to obtain (per acyl transfer reaction) 0.89 g (37%) of 5-(3-aminobenzoyloxy)-4-hydroxy-2,6,6-trimethyl-2-cyclohepten-1-one (AU209) as light yellow prisms.

Melting point: 121° to 123 ° C.

IR (KBr, cm$^{-1}$): 3386, 3326, 1717, 1654, 1285, 1233, 752.

1H-NMR (CDCl$_3$, ppm): 1.07 (3H, s), 1.18 (3H, s), 1.87 (3H, t, J=2 Hz), 2.46 (1H, d, J=13 Hz), 2.52 (1H, br), 2.63 (1H, d, J=13 Hz), 3.84 (2H, br), 4.61 (1H, dm, J=9 Hz), 4.91 (1H, d, J=9 Hz), 6.51 (1H, m), 6.89 (1H, m), 7.23 (1H, t, J=8 Hz), 7.36 (1H, m), 7.45 (1H, m).

EXAMPLE 39

4-(3-Aminobenzoyloxy)-5-hydroxy-2,6,6-trimethyl-2-cyclohepten-1-one (AU210) (970 mg, 3.2 mM) obtained in Example 38 was dissolved in ethyl acetate and was treated with a solution of 4N hydrogen chloride in ethyl acetate. The mixture was left to stand overnight and the resulting precipitate was collected by filtration to obtain 990 mg (91%) of a hydrochloride of the above compound. Melting point: 204° to 204.5° C. (decomposition).

IR (KBr, cm$^{-1}$): 3282, 3000–2500, 1712, 1664, 1290, 1276, 755.

EXAMPLE 40

5-(3-Aminobenzoyloxy)-4-hydroxy-2,6,6-trimethyl-2-cyclohepten-1-one (AU209) (152 mg, 0.5 mM) obtained in Example 38 was acetylated by a conventional method to obtain 125 mg (65%) of 5-(3-acetamidobenzoyloxy)-4-acetoxy-2,6,6-trimethyl-2-cyclohepten-1-one (AU224) as a colorless oily product.

IR (KBr, cm$^{-1}$): 3362, 1734, 1675, 1558, 1285, 1229, 754.

1H-NMR (CDCl$_3$), ppm): 1.07 (3H, s), 1.23 (3H, s), 1.79 (3H, s), 1.89 (3H, t, J=2 Hz), 2.20 (3H, s), 2.53 (1H, d, J=13 Hz), 2.73 (1H, d, J=13 Hz), 5.08 (1H, d, J=9 Hz), 5.96 (1H, dm, J=9 Hz), 6.37 (1H, m), 7.42 (1H, brt, J=8 Hz), 7.74 (1H, brd, J=8 Hz), 7.95 (1H, brs), 8.06 (1H, brd, J=8 Hz).

EXAMPLE 41

Saishin N (1.84 g, 10 mM) was treated with cinnamoyl chloride (2.00 g, 12 mM) as described in Example 17 and fractionated by silica gel column chromatography using hexane-ethyl acetate (5:1) as an eluent. From the first eluted portion 1.28 g (41%) of 4-cinnamoyloxy-5-hydroxy-2,6,6-trimethyl-2-cyclohepten-1-one (AU206) was obtained as a colorless oily product.

IR (KBr, cm$^{-1}$): 3492, 1711, 1674, 1636, 1165, 768.

1H-NMR (CDCl$_3$D$_2$O, ppm): 1.10 (3H, s), 1.15 (3H, s), 1.87 (3H, t, J=2 Hz), 2.43 (1H, d, J=13 Hz), 2.64 (1H, d, J=13 Hz), 3.48 (1H, d, J=9 Hz), 5.72 (1H, dm, J=9 Hz), 6.38 (1H, m), 6.53 (1H, d, J=16 Hz), 7.41 (3H, m), 7.56 (2H, m), 7.80 (1H, d, J=16 Hz).

The successive eluted portion was crystallized from a mixed solvent of ethyl acetate and hexane to obtain (per acyl transfer reaction) 0.72 g (22%) of 5-cinnamoyloxy-4-hydroxy-2,6,6-trimethyl-2-cyclohepten-1-one (AU205) as colorless needles. Melting point: 85.5° to 87° C.

IR (KBr, cm$^{-1}$): 3482, 1711, 1674, 1279, 769.

1H-NMR (CDCl$_3$+D$_2$O, ppm): 1.08 (3H, s), 1.15 (3H, s), 1.89 (3H, t, J=2 Hz), 2.46 (1H, d, J=13 Hz), 2.62 (1H, d, J=13 Hz), 4.58 (1H, dm, J=9 Hz), 4.82 (1H, d, J=9 Hz), 6.51 (1H, d, J=16 Hz), 6.53 (1H, m), 7.42 (3H, m), 7.55 (2H, m), 7.77 (1H, d, J=16 Hz).

EXAMPLE 42

4-Cinnamoyloxy-5-hydroxy-2,6,6-trimethyl-2-cyclohepten-1-one (AU206) (0.98 g, 3.1 mM) obtained in Example 41 was acetylated by a conventional method and crystallized from a mixed solvent of ethyl acetate and hexane to obtain 0.98 g (86%) of 5-acetoxy-4-cinnamoyloxy-2,6,6-trimethyl-2-cyclohepten-1-one (AU208) as colorless plates. Melting point: 138° to 139° C.

IR (KBr, cm$^{-1}$): 1743, 1718, 1675, 1633, 1310, 1232, 1159, 773.

1H-NMR (CDCl$_3$+D$_2$O, ppm): 1.05 (3H, s), 1.14 (3H, s), 1.89 (3H, t, J=2 Hz ), 2.00 (3H, s), 2.51 (1H, d, J=13 Hz), 2.71 (1H, d, J=13 Hz), 4.95 (1H, d, J=9 Hz), 5.93 (1H, dm, J=9 Hz), 6.37 (1H, m), 6.44 (1H, d, J=16 Hz), 7.42 (3H, m), 7.55 (2H, m), 7.74 (1H, d, J=16 Hz).

EXAMPLE 43

5-Cinnamoyloxy-4-hydroxy-2,6,6-trimethyl-2-cyclohepten-1-one (AU205) (0.39 g, 1.2 mM) obtained in Example 41 was acetylated by a conventional method and crystallized from a mixed solvent of ethyl acetate and hexane to obtain 0.19 g (44%) of 4-acetoxy-5-cinnamoyloxy-2,6,6-trimethyl-2-cyclohepten-1-one (AU207) as colorless prisms. Melting point: 64° to 65° C.

IR (KBr, cm$^{-1}$): 1756, 1716, 1672, 1633, 1312, 1225, 1158, 769.

1H-NMR (CDCl$_3$, ppm): 1.07 (3H, s), 1.18 (3H, s), 1.89 (3H, t, J=2 Hz), 2.01 (3H, s), 2.52 (1H, d, J=13 Hz), 2.70 (1H, d, J=13 Hz), 5.01 (1H, d, J=9 Hz), 5.88 (1H, dm, J=9 Hz), 6.32 (1H, m), 6.45 (1H, d, J=16 Hz), 7.42 (3H, m), 7.56(2H, m), 7.72 (1H, d, J=16 Hz).

EXAMPLE 44

Saishin N (1.84 g, 10 mM) was treated with 4-nitrobenzoyl chloride (2.23 g, 12 mM) according to the procedures described in Example 17. Crystallization of the mixture from ethyl acetate was repeated twice to obtain 0.97 g (26%) of 5-hydroxy-4-(4-nitrobenzoyloxy)-2,6,6-trimethyl-2-cyclohepten-1-one (AU212) as light yellow prisms. Melting point: 151° to 152.5° C.

IR (KBr, cm$^{-1}$): 3556, 1731, 1660, 1524, 1354, 1273, 1105, 722.

1H-NMR (CDCl$_3$+D$_2$O, ppm): 1.14 (3H, s), 1.17 (3H, s), 1.90 (3H, t, J=2 Hz), 2.48 (1H, d, J=13 Hz), 2.68 (1H, d, J=13 Hz), 3.55 (1H, d, J=9 Hz), 5.91 (1H, dm, J=9 Hz), 6.43 (1H, m), 8.27 (2H, d, J=9 Hz), 8.34 (2H, d, J=9 Hz).

The mother liquor of the crystals was concentrated. Then crystallization of the residue was repeated twice from ethyl acetate to obtain (per acyl transfer reaction) 0.99 g (26%) of 4-hydroxy-5-(4-nitrobenzoyloxy)-2,6,6-trimethyl-2-cyclohepten-1-one (AU211) as light yellow needles. Melting point: 148° to 150° C.

IR (KBr, cm$^{-1}$): 3552, 1716, 1674, 1522, 1349, 1275, 719.

1H-NMR (CDCl$_3$+D$_2$O, ppm): 1.10 (3H, s), 1.23 (3H, s), 1.91 (3H, t, J=2 Hz), 2.50 (1H, d, J=13 Hz), 2.66 (1H, d, J=13 Hz), 4.65 (1H, dm, J=9 Hz), 4.97 (1H, d, J=9 Hz), 6.53 (1H, m), 8.25 (2H, d, J=9 Hz), 8.32 (2H, d, J=9 Hz).

EXAMPLE 45

5-Hydroxy-4-(4-nitrobenzoyloxy)-2,6,6-trimethyl-2-cyclohepten-1-one (AU212) (751 mg, 2 mM) obtained in Example 44 was reduced at the nitro group according to the procedures described in Example 38 and fractionated by silica gel column chromatography using hexane-ethyl acetate (2:1) as an eluent. The first eluted portion was crystallized from a mixed solvent of ethyl acetate and hexane to obtain 320 mg (53%) of 4-(4-aminobenzoyloxy)-5-hydroxy-2,6,6-trimethyl-2-cyclohepten-1-one (AU215) as colorless prisms. Melting point: 152° to 153° C.

IR (KBr, cm$^{-1}$): 3648, 3524, 3437, 3360, 1685, 1672, 1605, 1273, 770.

1H-NMR (CDCl$_3$, ppm): 1.11 (3H, s), 1.16 (3H, s), 1.86 (3H, t, J=2 Hz), 2.30 (1H, d, J=5 Hz), 2.43 (1H, d, J=12 Hz), 2.66 (1H, d, J=12 Hz), 3.52 (1H, dd, J=9, 5 Hz), 4.14 (2H, brs), 5.79 (1H, dm, J=9 Hz), 6.42 (1H, m), 6.66 (2H, d, J=9 Hz), 7.90 (2H, d, J=9 Hz).

The successive eluted portion was crystallized from a mixed solvent of ethyl acetate and hexane to obtain (per acyl transfer reaction) 225 mg (37%) of 5-(4-aminobenzoyloxy)-4-hydroxy-2,6,6-trimethyl-2-cyclohepten-1-one (AU216) as colorless needles.

Melting point: 169.5° to 171° C.

IR (KBr, cm$^{-1}$): 3460, 3366, 3234, 1676, 1633, 1600, 1279, 1170.

1H-NMR (CDCl$^{-1}$, ppm): 1.07 (3H, s), 1.19 (3H, s), 1.88 (3H, t, J=2 Hz), 2.45 (1H, d, J=13 Hz), 2.51 (1H, brd, J=7 Hz), 2.63 (1H, d, J=13 Hz), 4.14 (2H, brs), 4.61 (1H, brs), 4.87 (1H, d, J=9 Hz), 6.55 (1H, m), 6.66 (2H, d, J=9 Hz), 7.88 (2H, d, J=9 Hz).

EXAMPLE 46

4-Hydroxy-5-(4-nitrobenzoyloxy)-2,6,6-trimethyl-2-cyclohepten-1-one (AU211) obtained in Example 44 was treated as described in Example 45 to obtain 4-(4-aminobenzoyloxy)-5-hydroxy-2,6,6-trimethyl-2-cyclohepten-1-one (AU215) and (per acyl transfer reaction) 5-(4-aminobenzoyloxy)-4-hydroxy-2,6,6-trimethyl-2-cyclohepten-1-one (AU216) as in Example 45.

EXAMPLE 47

A solution of 5-hydroxy-4-(4-nitrobenzoyloxy)-2,6,6-trimethyl-2-cyclohepten-1-one (AU212) (3.33 g, 10 mM) obtained in Example 44 in ethyl acetate (30 ml) was treated with platinum oxide (0.1 g) and catalytically reduced. After the catalyst was filtered off, the filtrate was treated as described in Example 45 to obtain 2.53 g (76%) of 4-(4-aminobenzoyloxy)-5-hydroxy-2,6,6-trimethyl-2-cyclohepten-1-one (AU215) as in Example 45.

EXAMPLE 48

5-Hydroxy-4-(4-nitrobenzoyloxy)-2,6,6-trimethyl-2-cyclohepten-1-one (AU212) (638 mg, 2 mM) obtained in Example 44 was acetylated by a conventional method and crystallized from a mixed solvent of ethyl acetate and hexane to obtain 683 mg (91%) of 51acetoxy-4-(4-nitrobenzoyloxy)-2,6,6-trimethyl-2-cyclohepten-1-one (AU196) as colorless needles. Melting point: 147° to 147.5° C.

IR (KBr, cm$^{-1}$): 1735, 1722, 1685, 1523, 1282, 123.4, 718.

1H-NMR (CDCl$_3$, ppm): 1.06 (3H, s), 1.15 (3H, s), 1.84 (3H, s), 1.91 (3H, t, J=2 Hz), 2.55 (1H, d, J=13 Hz), 2.72 (1H, d, J=13 Hz), 5.05 (1H, d, J=9 Hz), 6.03 (1H, dm, J=9 Hz), 6.36 (1H, m), 8.21 (2H, d, J=9 Hz), 8.33 (2H, d, J=9 Hz).

EXAMPLE 49

The product (AU196) of Example 48 (210 mg, 0.56 mM) was reduced at the nitro group as described in Example 38 and crystallized from a mixed solution of benzene and hexane to obtain 175 mg (94%) of 5-acetoxy-4-(4-aminobenzoyloxy)-2,6,6-trimethyl-2-cyclohepten-1-one (AU197). Melting point: 158.5° to 160° C.

IR (KBr, cm$^{-1}$): 3463, 3380, 3246, 1747, 1701, 1673, 1628, 1601, 1267.

1H-NMR (CDCl$_3$, ppm): 1.05 (3H, s), 1.14 (3H, s), 1.83 (3H, s), 1.89 (3H, t, J=2 Hz), 2.50 (1H, d, J=13 Hz), 2.73 (1H, d, J=13 Hz), 4.13 (2H, brs: disappeared by the addition of heavy water), 4.98 (1H, d, J=9 Hz), 6.00 (1H, dm, J=9 Hz), 6.42 (1H, m), 6.66 (2H, d, J=9 Hz), 7.84 (2H, d, J=9 Hz).

EXAMPLE 50

To a solution of 5-hydroxy-4-nitrobenzoyloxy)-2,6,6-trimethyl-2-cyclohepten-1-one (AU212) (1.67 g, 5 mM) obtained in Example 44 in tetrahydrofuran (5 ml), dihydropyran (4.5 ml) and p-toluenesulfonic acid (0.1 g) were added and it was stirred at room temperature overnight. The reaction mixture was concentrated, then diluted with ethyl acetate, washed with an aqueous dilute potassium carbonate solution and with brine, dried over magnesium sulfate, filtered, concentrated, and crystallized from hexane to obtain 1.97 g (94%) of the intermediate 5-tetrahydropyranyloxy-4-(4-nitrobenzoyloxy)-2,6,6-trimethyl-2-cyclohepten-1-one as colorless needles. Melting point: 133.5° to 135° C.

IR (KBr, cm$^{-1}$): 1721, 1678, 1524, 1280, 720.

The intermediate product so obtained (1.79 g, 4.7 mM) was reduced at the nitro group as described in Example 19 and purified by silica gel column chromatography using hexane-ethyl acetate (5:1) as an eluent to obtain 1.28 g (62%) of the further intermediate 4-(4-aminobenzoyloxy)-5-tetrahydropyranyloxy-2,6,6-trimethyl-2-cyclohepten-1-one as a colorless oily product.

The further intermediate product so obtained (2.88 g, 66 mM) was dissolved in acetic anhydride (15 ml) and treated with concentrated sulfuric acid (two drops) under ice-cooling, then warmed to room temperature and stirred for two hours. The mixture was treated with ice-water and stirred, extracted with ethyl acetate, washed with a saturated sodium bicarbonate solution and dried over magnesium sulfate. After filtration, the mixture was concentrated and the residue was crystallized from a mixed solvent of ethyl acetate and hexane to obtain 1.47 g (62%) of 4-(4-acetamidobenzoyloxy)-5-hydroxy-2,6,6-trimethyl-2-cyclohepten-1-one (AU237) as light yellow needles. Melting point: 133.5° to 135.0° C.

IR (KBr, cm$^{-1}$): 3355, 1711, 1678, 1600, 1538, 1273, 1110.

1H-NMR (CDCl$_3$, ppm): 1.10 (3H, s.), 1.15 (3H, s), 1.86 (3H, t, J=2 Hz), 2.21 (3H, s), 2.32 (1H, d, J=6 Hz), 2.44 (1H, d, J=13 Hz), 2.66 (1H, d, J=13 Hz), 3.53 (1H, dd, J=9, 6 Hz), 5.81 (1H, dm, J=9 Hz), 6.41 (1H, m), 7.46 (1H, brs), 7.62 (2H, d, J=9 Hz), 8.04 (2H, d, J=9 Hz).

EXAMPLE 51

Saishin N (1.84 g, 10 mM) was treated with 2-methoxybenzoyl chloride (2.05 g, 25 mM) according to the procedures described in Example 17 and fractionated by silica gel column chromatography using hexane-ethyl acetate (5:1) as an eluent. From the first eluted portion 1.57 g (49%) of 5-hydroxy-4-(2-methoxybenzoyloxy)-2,6,6-trimethyl-2-cyclohepten-1-one (AU214) was obtained as a colorless oily product.

IR (KBr, cm$^{-1}$): 3510, 1719, 1675, 1602, 1299, 1250, 1099, 757.

1H-NMR (CDCl$_3$+D$_2$O, ppm): 1.10 (3H, s), 1.19 (3H, 3), 1.85 (3H, t, J=2 Hz), 2.42 (1H, d, J=12 Hz), 2.64 (1H, d, J=12 Hz), 3.54 (1H, d, J=9 Hz), 3.94 (3H, s), 5.75 (1H, dm, J=9 Hz), 6.38 (1H, m), 7.02 (1H, brd, J=8 Hz), 7.08 (1H, brd, J=7 Hz), 7.53 (1H, m), 7.86 (1H, dd, J=7,2 Hz).

1.53 g (47%) of 4-hydroxy-5-(2-methoxybenzoyloxy)-2,6,6-trimethyl-2-cyclohepten-1-one (AU213) were obtained (per acyl transfer reaction) as a colorless oily product from the successive eluted portion.

IR (KBr, cm$^{-1}$): 3501, 1718, 1670, 1602, 1302, 1253, 758.

1H-NMR (CDCl$_3$+D$_2$O, ppm): 1.06 (3H, s), 1.13 (3H, s), 1.88 (3H, t, J=2 Hz), 2.44(1H, d, J=13 Hz), 2.65 (1H, d, J=13 Hz), 3.93 (3H, s), 4.66 (1H, dm, J=9 Hz), 4.93 (1H, d, J=9 Hz), 6.55 (1H, m): 7.011H, brd, J=8 Hz), 7.05 (1H, brd, J=7 Hz), 7.51 (1H, m), 7.75 (1H, dd, J=7, 2 Hz).

EXAMPLE 52

Saishin N (2.40 g, 13 mM) was treated with 2-chloro-4-nitrobenzoyl chloride (374 g, 17 mM) according to the procedures described in Example 17, fractionated by silica gel column chromatography using hexane-ethyl acetate (5:1) as an eluent. The first eluted portion was crystallized from a mixed solvent of ethyl acetate and hexane to obtain 1.45 g (30%) of 4-(2-chloro-4-nitrobenzoyloxy)-5-hydroxy-2,6,6-trimethyl-2-cyclohepten-1-one (AU219) as a colorless powder.

Melting point: 108° to 109.5° C.

IR (KBr, cm$^{-1}$): 3502, 1738, 1676, 1528, 1351, 1242, 734.

1H-NMR (CDCl$_3$+D$_2$O, ppm): 1.13 (3H, s), 1.17 (3H, s), 1.89 (3H, t, J=2 Hz), 2.47 (1H, d, J=13 Hz), 2.65 (1H, d, J=13 Hz), 3.55 (1H, d, J=9 Hz), 5.90 (1H, dm, J=9 Hz), 6.40 (1H, m), 8.07 (1H, d, J=8 Hz), 8.20 (1H, dd, J=8, 2 Hz),8.36 (1H, d, J=2 Hz).

The successive eluted portion was crystallized from a mixed solvent of ethyl acetate and hexane to obtain (per acyl transfer reaction) 1.069 (22%) of 5-(2-chloro-4-nitrobenzoyloxy)-4-hydroxy-2,6,6-trimethyl-2-cyclohepten-1-one (AU220) as a colorless powder. Melting point: 221° to 222° C.

IR (KBr, cm$^{-1}$): 3568, 1718, 1675, 1523, 1354, 1273, 735.

1H-NMR (CDCl$_3$+D$_2$O, ppm): 1.14 (3H, s), 1.15 (3H, s), 1.90 (3H, t, J=2 Hz), 2.50 (1H, d, J=13 Hz), 2.64 (1H, d, J=13 Hz), 4.64 (1H, dm, J=9 Hz), 5.02 (1H, d, J=9 Hz), 6.51 (1H, m), 8.00 (1H, d, J=8 Hz), 8.19 (1H, dd, J=8, 2 Hz), 8.36 (1H, d, J=2 Hz).

EXAMPLE 53

Saishin N (3.68 g, 20 mM) was treated with the hydrochloride of 4-dimethylaminobenzoyl chloride according to the procedures described in Example 17, purified by silica gel column chromatography using hexane-ethyl acetate (5:1) as an eluent and crystallized from a mixed solvent of ethyl acetate and hexane to obtain 0.67 g (10%) of 4-(4-dimethylaminobenzoyloxy)-5-hydroxy-2,6,6-trimethyl-2-cyclohepten-1-one (AU236) as colorless needles. Melting point: 162° to 163° C.

IR (KBr, cm$^{-1}$): 3517, 1673, 1616, 1286, 1190, 1116, 828, 770.

1H-NMR (CDCl$_3$, ppm): 1.12 (3H, s), 1.16 (3H, s), 1.87 (3H, t, J=2 Hz), 2.39 (1H, brd), 2.44 (1H, d, J=13 Hz), 2.67

(1H, d, J=13 Hz), 3.07 (6H, s), 3.51 (1H, dd, J=9, 5 Hz), 5.79 (1H, dm, J=9 Hz), 6.44 (1H, m), 6.67 (2H, d, J=9 Hz), 7.95 (2H, d, J=9 Hz).

EXAMPLE 54

Saishin N (5 g, 27 mM) was treated with 4-nitrocinnamoyl chloride according to the procedures described in Example 17 and crystallized from a mixed solvent of ethyl acetate and hexane to obtain 7.50 g (77%) of 5-hydroxy-4-(4-nitrocinnamoyloxy)-2,6,6-trimethyl-2-cyclohepten-1-one (AU150) as colorless needles.

Melting point: 172° to 173° C.

IR (KBr, cm$^{-1}$): 3529, 1709, 1669, 1516, 1345, 1178, 848.

1H-NMR (CDCl$_3$, ppm): 1.11 (3H, s), 1.16 (3H, s), 1.88 (3H, t, J=2 Hz), 2.16 (1H, brd, J=5 Hz; disappeared by the addition of heavy water), 2.45 (1H, d, J=13 Hz, 2.65 (1H, d, J=13 Hz), 3.48 (1H, dd, J=9, 5 Hz; d by the addition of heavy water, J=9 Hz), 5.75 (1H, dm, J=9 Hz), 6.36 (1H, m), 6.64 (1H, d, J=16 Hz), 7.71 (2H, d, J=9 Hz), 7.82 (1H, d, J=16 Hz), 8.28 (2H, d, J=9 Hz).

EXAMPLE 55

The product of Example 54 (6.5 g, 18.1 mM) was reduced at the nitro group as described in Example 19 and fractionated by silica gel column chromatography using hexane-ethyl acetate (2:1) as an eluent. From the first eluted portion 2.55 g (43%) of 4-(4-aminocinnamoyloxy)-5-hydroxy-2,6,6-trimethyl-2-cyclohepten-1-one (AU401) was obtained as a yellow glassy product. Melting point: 72° to 74° C.

IR (KBr, cm$^{-1}$): 3452, 3365, 3234, 1699, 1675, 1596, 1518, 1156.

1H-NMR (CDCl$_3$, ppm): 1.09 (3H, s), 1.15 (3H, s), 1.85 (3H, t, J=2 Hz), 2.34 (1H, brd, J=-4 Hz: disappeared by the addition of heavy water), 2.42 (1H, d, J=12 Hz), 2.64 (1H, d, J=12 Hz), 3.46 (1H, dd, J=9, 4 Hz; d by the addition of heavy water, J=9 Hz), 5.69 (1H, dm, J=9 Hz), 6.29 (1H, d, J=16 Hz), 6.37 (1H, m), 6.66 (1H, d, J=9 Hz), 7.37 (1H, d, J=9 Hz) 7.69 (1H, d, J=16 Hz).

From the successive eluted portion 2.55 g (43%) of 5-(4-aminocinnamoyloxy)-4-hydroxy-2,6,6-trimethyl-2-cyclohepten-1-one (AU402) were obtained (per acyl transfer reaction) as a yellow glassy product. Melting point: 49° to 50° C.

IR (KBr, cm$^{-1}$): 3459, 3365, 3233, 1699, 1669, 1623, 1597, 1518, 1159.

1H-NMR (CDCl$_3$, ppm): 1.06 (3H, s), 1.13 (3H, s), 1.87 (3H, t, J=2 Hz), 2.43 (1H, d, J=13 Hz), 2.61 (1H, d, J=13 Hz), 4.04 (1H, brd, J=4 Hz; disappeared by the addition of heavy water), 4.56 (1H, dm, J=9 Hz), 4.79 (1H, d, J=9 Hz), 6.29 (1H, d, J=16 Hz), 6.54 (1H, m), 6.66 (1H, d, J=8 Hz), 7.37 (1H, d, J=8 Hz), 7.66 (1H, d, J=16 Hz).

EXAMPLE 56

Saishin N (5.0 g, 27 mM) was treated with 2-furoyl chloride according to the procedures described in Example 17 and fractionated by silica gel column chromatography using benzene-ethyl acetate (25:1) as an eluent. From the first eluted portion 1.36 g (18%) of 4-(2-furoyloxy)-5-hydroxy-2,6,6-trimethyl-2-cyclohepten-1-one (AU403) was obtained as a colorless oily product.

IR (KBr, cm$^{-1}$): 3500, 1732, 1715, 1682, 1668, 1471.

1H-NMR (CDCl$_3$, ppm): 1.10 (3H, s), 1.16 (3H, s), 1.86 (3H, t, J=2 Hz), 2.29 (1H, d, J=5 Hz; disappeared by the addition of heavy water), 2.44 (1H, d, J=13 Hz), 2.65 (1H, d, J=13 Hz), 3.53 (1H, dd, J=9, 5 Hz; d by the addition of heavy water, J=9 Hz), 5.80 (1H, dm, J=9 Hz), 6.41 (1H, m), 6.57 (1H, dd, J=3, 2 Hz), 7.30 (1H, dd, J=3, 1 Hz), 7.62 (1H, dd, J=2, 1 Hz).

The successive eluted portion was crystallized from a mixed solvent of ethyl acetate and hexane to obtain (per acyl transfer reaction) 1.36 g (18%) of 5-(2-furoyloxy)-4-hydroxy-2,6,6-trimethyl-2-cyclohepten-1-one (AU404) as colorless needles. Melting point: 102.5° to 103.5° C.

IR (KBr, cm$^{-1}$): 3508, 3118, 1712, 1674, 1474, 1306, 1186, 1129.

1H-NMR (CDCl$^{-3}$, ppm): 1.09 (3H, s), 1.16 (3H, s), 1.89 (3H, t, J=2 Hz), 2.31 (1H, d, J=7 Hz; disappeared by the addition of heavy water), 2.46 (1H, d, J=13 Hz), 2.64 (1H, d, J=13 Hz), 4.63 (1H, m; dm by the addition of heavy water), 4.88 (1H, d, J=9 Hz), 6.52 (1H, m), 6.55 (1H, m), 7.25 (1H, m), 7.63 (1H, m).

EXAMPLE 57

DCC (6.81 g, 33 mM) and 4-dimethylaminopyridine (50 mg) were added to a solution of Saishin N (5.53 g, 30 mM) in methylene chloride (50 ml). The mixture was then treated with 4-nitrobenzoic acid (5.51 g, 33 mM) with stirring at 0° C., stirred for four hours and filtered to provide a filtrate. The residue was extracted with hot ethyl acetate (200 ml) at 40° C. and was combined with the above filtrate which were concentrated and crystallized from ethyl acetate to obtain 6.67 g (66%) of 5-hydroxy-4-(4-nitrobenzoyloxy)-2,6,6-trimethyl-2-cyclohepten-1-one (AU212) as obtained in Example 44.

EXAMPLE 58

To a solution of Saishin N (5.53 g, 30 mM) in methylene chloride (30 ml), 4-aminobenzoic acid (5.35 g, 39 mM), DCC (8.05 g, 39 mM) and 4-dimethylaminopyridine (0.15 g) were added and it was stirred for 10 hours at 0° C. The mixture was then filtered and washed with ethyl acetate. The filtrate and wash liquid were combined and concentrated. The residue was purified by silica gel column chromatography using hexane-ethyl acetate (2:1) as an eluent and crystallized from ethyl acetate to obtain 5.52 g (61%) of 4-(4-aminobenzoyloxy)-5-hydroxy-2,6,6-trimethyl-2-cycloheptan-1-one (AU215) as obtained in Example 45.

EXAMPLE 59

Saishin N (9.21 g, 50 mM) was treated with 3,4-diaminobenzoic acid (12.93 g, 85 mM) according to the procedures described in Example 20, purified by silica gel column chromatography using hexane-ethyl acetate (1:1) as an eluent and crystallized from a mixed solution of ethyl acetate and hexane to obtain 6.21 g (41%) of 4-(3,4-diaminobenzoyloxy)-5-hydroxy-2,6,6-trimethyl-2-cyclohepten-1-one (AU240) as light orange crystals. Melting point: 136° to 137° C.

IR (KBr, cm–1): 3475, 3354, 3272, 1690, 1668, 1314, 1280, 1218.

1H-NMR (CDCl$_3$, ppm): 1.10 (3H, s), 1.14 (3H, s), 1.85 (3H, t, J=2 Hz), 2.42 (1H, d, J=13 Hz), 2.65 (1H, d, J=13 Hz), 3.50 (1H, d, J=9 Hz), 5.78 (1H, dm, J=9 Hz), 6.40 (1H, m), 6.69 (1H, d, J=8 Hz), 7.43 (1H, d, J=2 Hz), 7.51 (1H, dd, J=8, 2 Hz).

EXAMPLE 60

Saishin N (3.68 g, 20 mM) was treated with 2,4-dinitrobenzoic acid (6.79 g, 32 mM) according to the procedures described in Example 20, forming a mixture of 4-(2,4-dinitrobenzoyloxy)-5-hydroxy-2,6,6-trimethyl-2-cyclohepten-1-one and (per acyl transfer reaction) 5-(2,4-dinitrobenzoyloxy)-4-hydroxy-2,6,6-trimethyl-2-cyclohepten-1-one, and then the mixture was reduced at the nitro groups according to the procedures described in Example 19 and fractionated by silica gel column chromatography using hexane-ethyl acetate (3:2) as an eluent. The first eluted portion was crystallized from a mixed solution of ethyl acetate and hexane to obtain 1.65 g (26%) of 4-(2,4-diaminobenzoyloxy)-5-hydroxy-2,6,6-trimethyl-2-cyclohepten-1-one (AU242) as a brown powder. Melting point: 154° to 156° C.

IR (KBr, cm$^{-1}$): 3467, 3378, 1668, 1619, 1257.

1H-NMR (CDCl$_3$, ppm): 1.10 (3H, s), 1.15 (3H, s), 1.86 (3H, t, J=2 Hz), 2.40 (1H, brs; disappeared by the addition of heavy water), 2.43 (1H, d, J=12 Hz), 2.65 (1H, d, J=12 Hz), 3.52 (1H, dd, J=9, 2 Hz; d by the addition of heavy water, J=9 Hz), 3.99 (2H, br; disappeared by the addition of heavy water), 5.72 (2H, br; disappeared by the addition of heavy water), 5.75 (1H, dm, J=9 Hz), 5.87 (1H, d, J=2 Hz), 6.00 (1H, dd, J=9, 2 Hz), 6.40 (1H, m), 7.71 (1H, d, J=9 Hz).

The successive eluted portion was crystallized from ethyl acetate to obtain 1.63 g (26%) of 5-(2,4-diaminobenzoyloxy)-4-hydroxy-2,6,6-trimethyl-2-cyclohepten-1-one (AU241) as yellow needles. Melting point: 185° to 186.5° C.

IR (KBr, cm$^{-1}$): 3481, 3363, 3300, 1672, 1661, 1625, 1251.

1H-NMR (CDCl$_3$, ppm): 1.07 (3H, s), 1.18 (3H, s), 1.88 (3H, t, J=2 Hz), 2.44 (1H, d, J=13 Hz), 2.55 (1H, d, J=6 Hz), 2.63 (1H, d, J=13 Hz), 3.97 (2H, br), 4.62 (1H, m), 4.84 (1H, d, J=9 Hz), 5.71 (2H, br), 5.87 (1H, d, J=2 Hz), 6.00 (1H, dd, J=9, 2 Hz), 6.57 (1H, m), 7.71 (1H, d, J=9 Hz).

EXAMPLE 61

Saishin N (5.0 g, 27.1 mM) was treated with 3-methoxy-4-tetrahydropyranyloxy cinnamic acid (9.82 g, 35.3 mM) according to the procedures described in Example 20, fractionated by reversed phase chromatography (chromatorex ODS: Fuji Division) using 50 to 70% methanol as an eluent and further by silica gel column chromatography using hexane-ethyl acetate (4:1) as an eluent. From the first eluted portion 4.10 g (34%) of the 5-hydroxy intermediate 5-hydroxy-4-(3-methoxy-4-tetrahydropyranyloxy-cinnamoyloxy)-2,6,6-trimethyl-2-cyclohepten-1-one were obtained as a colorless glassy product. 4.10 g (34%) of the 4-hydroxy intermediate 4-hydroxy-5-(3-methoxy-4-tetrahydropyranyloxy-cinnamoyloxy)-2,6,6-trimethyl-2-cyclohepten-1-one as a colorless glassy product were obtained (per acyl transfer reaction) from the successive eluted portion.

The first eluted portion 5-hydroxy intermediate (2.0 g, 4.5 mM) was dissolved in tetrahydrofuran (20 ml) and treated with 1N hydrochloric acid (10 ml) under ice-cooling and stirring, and stirred for three hours. Then the mixture was diluted with ethyl acetate, washed with water, dried, filtered, and concentrated. The residue was purified by silica gel column chromatography using hexane-ethyl acetate (4:1) as an eluent and crystallized from a mixed solvent of ethyl acetate and hexane to obtain 1.21 g (74%) of 5-hydroxy-4-(4-hydroxy-3-methoxycinnamoyloxy)-2,6,6-trimethyl-2-cyclohepten-1-one (AU416) as colorless needles. Melting point: 141.5° to 142.5° C.

IR (KBr, cm$^{-1}$): 3482, 3283, 1730, 1719, 1650, 1631, 1595, 1521, 1155.

1H-NMR (CDCl$_3$, ppm): 1.10 (3H, s), 1.15 (3H, s), 1.86 (3H, t, J=2 Hz), 2.26 (1H, d, J=5 Hz; disappeared by the addition of heavy water), 2.43 (1H, d, J=12 Hz), 2.65 (1H, d, J=12 Hz), 3.47 (1H, dd, J=9, 5 Hz; d by the addition of heavy water, J=9 Hz), 3.94 (3H, s), 5.71 (1H, dm, J=9 Hz), 5.91 (1H, s; disappeared by the addition of heavy water), 6.36 (1H, d, J=16 Hz), 6.37 (1H, t, J=2 Hz), 6.94 (1H, d, J=8 Hz), 7.05 (1H, d, J=2 Hz), 7.10 (1H, dd, J=8, 2 Hz), 7.47 (1H, t, J=16 Hz).

The second eluted component 4-hydroxy intermediate (3.4 g, 7.6 mM) was treated in the same manner as above to obtain 2.19 g (79%) of 4-hydroxy-5-(4-hydroxy-3-methoxycinnamoyloxy)-2,6,6-trimethyl-2-cyclohepten-1-one (AU414) as colorless needles.

Melting point: 125° to 127° C.

IR (KBr, cm$^{-1}$): 3500–3200, 1737, 1710, 1668, 1631, 1602, 1514, 1281, 1159.

1H-NMR (CDCl$_3$, ppm): 1.07 (3H, s), 1.14 (3H, s), 1.88 (3H, t, J=2 Hz), 2.35 (1H, d, J=7 Hz; disappeared by the addition of heavy water), 2.44 (1H, d, J=13 Hz), 2.62 (1H, d, J=13 Hz), 3.95 (3H, s), 4.57 (1H, m), 4.81 (1H, d, J=9 Hz), 5.90 (1H, s; disappeared by the addition of heavy water), 6.35 (1H, d, J=16 Hz), 6.54 (1H, m, J=2 Hz), 6.93 (1H, d, J=8 Hz), 7.05 (1H, d, J=2 Hz), 7.11 (1H, dd, J=8, 2 Hz), 7.68 (1H, d, J=16 Hz).

EXAMPLE 62

To a mixed solution of Saishin N (1.84 g, 10 mM), methylene chloride (10 ml) and pyridine (1.12 ml), 1-methyl-3-pyrrolecarboxylic acid (1.25 g, 12 mM) and 2-chloro-1,3-dimethylimidazolinium chloride (2.03 g, 1.2 mM) were added, and it was stirred at room temperature overnight. The reaction mixture was filtered and the residue obtained by the concentration of the filtrate was purified by silica gel column chromatography using a mixed liquid of benzene-ethyl acetate as an eluent and crystallized from a mixed solvent of ethyl acetate and hexane to obtain 1.97 g (67.7%) of 4-(1-methyl-2-pyrrolylcarbonyloxy)-5-hydroxy-2,6,6-trimethyl-2-cyclohepten-1-one (AU501) as glassy crystals. Melting point: 141.0° to 141.5° C.

IR (KBr, cm$^{-1}$): 3406, 1684, 1656, 1115, 740.

1H-NMR (CDCl$_3$, ppm): 1.10 (3H, s), 1.15 (3H, s), 1.86 (3H, t, J=2 Hz), 2.34 (1H, d, J=4 Hz), 2.43 (1H, d, J=12 Hz), 2.64 (1H, d, J=12 Hz), 3.51 (1H, dd, J=9, 5 Hz), 3.96 (3H, s), 5.74 (1H, dm, J=9 Hz), 6.15 (1H, dd, J=4, 2 Hz), 6.38 (1H, m), 6.86 (1H, t, J=2 Hz), 7.02 (1H, dd, J=4, 2 Hz).

EXAMPLE 63

The crude product obtained by the condensation of Saishin N (1.84 g, 10 mM) and 5-methyl-4-imidazolylcarboxylic acid (1.51 g, 12 mM) according to the procedures described in Example 20 was extracted with ethyl acetate, washed with a saturated sodium bicarbonate solution and with brine, dried over magnesium sulfate, filtered and concentrated. The residue was fractionated by silica gel column chromatography using hexane-ethyl acetate (3:1) as an eluent. The first eluted portion was crystallized from a mixed solvent of ethyl acetate and hexane to obtain 0.81 g (28%) of 5-hydroxy-4-(5-methyl-4-imidazolylcarbonyloxy)-2,6,6-trimethyl-2-cyclohepten-1-one (AU503) as a colorless powder. Melting point: 99° to 101° C.

IR (KBr, cm$^{-1}$): 3600–2500, 1709, 1673, 1100.

1H-NMR (CDCl$_3$, ppm) 1.13 (3H, s),1.16 (3H, s), 1.83 (3H, t, J=2 Hz), 2.43 (1H, d, J=12 Hz), 2.64 (1H, d, J=12 Hz), 3.52 (1H, d, J=9 Hz), 5.72 (1H, brd), 6.34 (1H, m), 7.50 (1H, s).

The successive eluted portion was crystallized from a mixed solvent of ethyl acetate and hexane to obtain (per acyl transfer reaction) 0.32 g (11%) of 4-hydroxy-5-(5-methyl-4-imidazolylcarbonyloxy)-2,6,6-trimethyl-2-cyclohepten-1-one (AU504) as a colorless powder. Melting point: 201° to 202° C.

IR (KBr, cm$^{-1}$): 3448, 3100–2400, 1708, 1668.

1H-NMR (CDCl$_3$, ppm): 1.10 (3H, s), 1.15 (3H, s), 1.88 (3H, t, J=2 Hz), 2.54 (1H, d, J=13 Hz), 2.56 (3H, s), 2.62 (1H, d, J=13 Hz), 4.10 (1H, dm, J=9 Hz), 5.12 (1H, d, J=9 Hz), 6.47 (1H, m), 7.65 (1H, s).

EXAMPLE 64

Saishin N (3.68 g, 20 mM) and 4-tetrahydropyranyloxy benzoic acid (7.0 g, 30 mM) were condensed according to the procedures described in Example 20 to obtain 4.93 g (63.5%) of the intermediate 5-hydroxy-4-(4-tetrahydropyranyloxy-benzoyloxy)-2,6,6-trimethyl-2-cyclohepten-1-one. The product so obtained (2.0 g, 5 mM) was hydrolyzed according to the procedures described in Example 61 and crystallized from a mixed solvent of ethyl acetate and hexane to obtain 0.3 g (20%) of 5-hydroxy-4-(4-hydroxybenzoyloxy)-2,6,6-trimethyl-2-cyclohepten-1-one (AU505) as a colorless powder.

Melting point: 123° to 125° C.

IR (KBr, cm$^{-1}$): 3405, 1712, 1656, 1611, 1267, 1099.

1H-NMR (DMSO-d$_6$, ppm): 0.96 (3H, s), 1.00 (3H, s), 1.77 (3H, brs), 2.32 (1H, d, J=13 Hz), 2.68 (1H, d, J=13 Hz), 3.31 (1H, dd, J=9, 3 Hz), 5.46 (1H, d, J=6 Hz), 5.72 (1H, dm, J=9 Hz), 6.48 (1H, m), 6.86 (2H, d, J=9 Hz), 7.92 (2H, d, J=9 Hz), 10.3 (1H, brs).

EXAMPLE 65

Saishin N (1.84 g, 10 mM) and 4-tetrahydropyranyloxy cinnamic acid (2.98 g, 12 mM) were treated as described in Example 61 to obtain 5-hydroxy-4-(4-tetrahydropyranyloxy-cinnamoyloxy)-2,6,6-trimethyl-2-cyclohepten-1-one as an intermediate, and this was then hydrolyzed, whereupon the hydrolyzed product was crystallized from a mixed solvent of ethyl acetate and hexane, to obtain 0.29 g (18%) of 5-hydroxy-4-(4-hydroxycinnamoyloxy)-2,6,6-trimethyl-2-cyclohepten-1-one (AU506) as colorless crystals. Melting point: 176° to 177° C.

IR (KBr, cm$^{-1}$): 3386, 3100–2400, 1713, 1654, 1608, 1516, 1279, 1158.

1H-NMR (CDCl$_3$, ppm): 1.10 (3H, s), 1.15 (3H, s), 1.87 (3H, t, J=2 Hz), 2.43 (1H, d, J=12 Hz), 2.65 (1H, d, J=12 Hz), 3.48 (1H, d, J=9 Hz), 5.72 (1H, dm, 9 Hz), 6.33 (1H, d, J=16 Hz), 6.39 (1H, m), 6.86 (2H, d, J=9 Hz), 7.42 (2H, d, J=9 Hz), 7.71 (1H, d, J=16 Hz).

EXAMPLE 66

4-Acetoxybenzoic acid (2.16 g, 12 mM), 2-chloro-1-methylpyridinium iodide (3.07 g, 12 mM) and triethylamine (3.37 ml, 24 mM) were added to a solution of Saishin N (1.84 g, 10 mM) in methylene chloride (20 ml). The mixture was stirred for seven days at room temperature and treated with water, extracted with ethyl acetate, washed successively with dilute hydrochloric acid, brine, a saturated sodium bicarbonate solution and brine, and dried over magnesium sulfate. After filtration, the filtrate was concentrated, purified by silica gel column chromatography using hexane-ethyl acetate (5:1) as an eluent and crystallized from a mixed solvent of hexane-ethyl acetate to obtain 0.85 g (25%) of 4-(4-acetoxybenzoyloxy)-5-hydroxy-2,6,6-trimethyl-2-cyclohepten-1-one (AU217) as colorless needles. Melting point: 132° to 133° C.

IR (KBr, cm$^{-1}$): 3514, 1744, 1731, 1675, 1262, 1228, 1102.

1H-NMR (CDCl$_3$+D$_2$O, ppm): 1.13 (3H, s), 1.17 (3H, s), 1.89 (3H, t, J=2 Hz), 2.34 (3H, s), 2.46 (1H, d, J=13 Hz), 2.67 (1H, d, J=13 Hz), 3.54 (1H, d, J=9 Hz), 5.86 (1H, dm, J=9 Hz), 6.42 (1H, m), 7.23 (2H, d, J=9 Hz), 8.13 (2H, d, J=9 Hz).

EXAMPLE 67

Manganese dioxide (5.5 g) was added to a solution of 5-benzoyloxy-4-hydroxy-2,6,6-trimethyl-2-cyclohepten-1-one (AU183) (0.9 g, 2.4 mM) obtained in Example 7 in methylene chloride (20 ml). The mixture was stirred for two days at room temperature, filtered, and concentrated. The residue was purified by silica gel column chromatography using hexane-ethyl acetate (10:1) as an eluent to obtain 0.47 g (69%) of 5-benzoyloxy-2,6,6-trimethyl-2-2-cyclohepten-1,4-dione (AU225) as colorless plates. Melting point: 68° to 68.5° C.

IR (KBr, cm$^{-1}$): 1720, 1687, 1274, 1110, 716.

1H-NMR (CDCl$_3$, ppm): 1.27 (6H, s), 2.01 (3H, t, J=2 Hz), 2.69 (1H, d, J=13 Hz), 2.71 (1H, d, J=13 Hz), 5.10 (1H, s), 6.46 (1H, m), 7.47 (2H, m), 7.60 (1H, m), 8.01 (2H, m).

EXAMPLE 68

Pyridinium chlorochromate (1.72 g, 8 mM) and cerite (1.5 g) were added to methylene chloride (40 ml). A solution of 4-benzoyloxy-5-hydroxy-2,6,6-trimethyl-2-cyclohepten-1-one (AU190) (0.577 g, 2 mM) obtained in Example 30 in methylene chloride (5 ml) was added dropwise to the mixture with stirring at room temperature and then it was stirred for eight hours. The reaction mixture was treated with ether (50 ml) and magnesium sulfate, left to stand for 30 minutes, filtered, and concentrated. The residue was extracted with ether, separated by thin-layer chromatography (Merck 5744) using hexane-ethyl acetate (3:1) as a developing solvent and crystallized from a mixed solution of ethyl acetate and hexane to brain 0.309 (69%) of 4-benzoyloxy-2,6,6-trimethyl-2-cyclohepten-1,5-dione (AU226) as colorless plates. Melting point: 91° to 92° C.

IR (KBr, cm$^{-1}$): 1736, 1721, 1670, 1274, 1122.

1H-NMR (CDCl$_3$, ppm): 1.17 (3H, s), 1.36 (3H, s), 1.94 (3H, d, J=2 Hz), 2.74 (1H, d, J=14 Hz), 2.27 (1H, d, J=14 Hz), 6.63 (2H, m), 7.47 (2H, m), 7.62 (1H, m), 8.13 (2H, m).

EXAMPLE 69

N,N-Dimethylhydrazine (15.9 ml, 210 mM) and acetic acid (3 ml) were added to a solution of 5-hydroxy-4-(4-methoxybenzyloxy)-2,6,6-trimethyl-2-cyclohepten-1-one (AUM09) (21.3 g, 70 mM) obtained in Example 1 in ethanol (60 ml). The mixture was heated under reflux for five hours, concentrated and purified by silica gel column chromatography using hexane-ethyl acetate (10:1) as an eluent to obtain 13.35 g (55%) of the intermediate 5-hydroxy-4-(4-methoxybenzyloxy)-2,6,6-trimethyl-2-cyclohepten-1-one dimethylhydrazone as an orange oily product.

55% sodium hydride (0.79 g, 18 mM) and methyl iodide (1.43 ml, 23 mM) were added to a solution of the above dimethylhydrazone (5.20 g, 15 mM) in tetrahydrofuran (30 ml) and stirred for six hours at room temperature. The reaction solution was then poured onto ice-water, extracted with ethyl acetate, washed with brine, dried over magnesium sulfate, filtered, and concentrated. The residue was fractionated by silica gel column chromatography using hexane-ethyl acetate (20:1 to 5:1) as an eluent to obtain two kinds of stereoisomers, 5-methoxy-4-(4-methoxybenzyloxy)-2,6,6-trimethyl-2-cyclohepten-1-one dimethylhydrazone, 3.14 g (58%) and 0.78 g (14.4%), respectively.

1H-NMR (CDCl$_3$, ppm): 0.99 (3H, s), 1.02 (3H, s), 1.92 (3H, t, J=2 Hz), 2.05 (1H, d, J=14 Hz), 2.41 (3H, s), 2.92 (1H, d, J=8 Hz), 3.00 (1H, d, J=14 Hz), 3.55 (3H, s), 3.80 (3H, s), 4.08 (1H, m), 4.59 (1H, d, J=11 Hz), 4.68 (1H, d, J=11 Hz), 6.01 (1H, ml, 6.87 (2H, d, J=9 Hz), 7.31 (2H, d, J=9 Hz).

1H-NMR (CDCl$_3$, ppm): 0.98 (3H, s), 1.10 (3H, s), 1.94 (3H, t, J=2 Hz), 2.11 (1H, d, J=13 Hz), 2.21 (1H, d, J=13 Hz), 2.47 (3H, s), 2.90 (1H, d, J=8 Hz), 3.56 (3H, s), 3.80 (3H, s), 3.96 (1H, m), 4.56 (1H, d, J=11 Hz), 4.67 (1H, d, J=11 Hz), 5.56 (1H, m), 6.87 (2H, d, J=9 Hz), 7.29 (2H, d, J=9 Hz).

The mixture of the above isomers (3.14 g, 8.7 mM) was dissolved in a mixed solution of ethanol (19 ml) and water (1 ml), and was treated with methyl iodide (0.8 ml, 13 mM), heated under reflux for eight hours and concentrated. The residue was purified by silica gel column chromatography using hexane-ethyl acetate (20:1) as an eluent to obtain 1.14 g (41%) of 5-methoxy-4-(4-methoxybenzyloxy)-2,6,6-trimethyl-2-cyclohepten-1-one (AU221) as a yellow oily product.

IR (KBr, cm$^{-1}$): 1673, 1514, 1249, 1113.

1H-NMR (CDCl$_3$, ppm): 0.99 (3H, s), 1.06 (3H, s), 1.82 (3H, t, J=2 Hz), 2.29 (1H, d, J=13 Hz), 2.41 (1H, d, J=13 Hz), 2.88 (1H, d, J=8 Hz), 3.57 (3H, s), 3.82 (3H, s), 4o17 (1H, dm, J=8 Hz), 4.64 (1H, d, J=11 Hz), 4.80 (1H, d, J=11 Hz), 6.56 (1H, m), 6.90 (2H, d, J=9 Hz), 7.33 (2H, d, J=9 Hz).

EXAMPLE 70

5-Hydroxy-4-(4-methoxybenzyloxy)-2,6,6-trimethyl-2-cyclohepten-1-one dimethylhydrazone (13.35 g, 38 mM) obtained in Example 69 as an intermediate was methylated as described in Example 69 to form 5-methoxy-4-(4-methoxybenzyloxy)-2,6,6-trimethyl-2-cyclohepten-1-one dimethylhydrazone, and this was then dissolved in a mixed solution of 6N hydrochloric acid (40 ml) and tetrahydrofuran (20 ml) and warmed to 50° C. for six hours to remove the 4-methoxybenzyloxy group and dimethylhydrazone, then extracted with ethyl acetate, washed with a saturated sodium bicarbonate solution and with brine, dried over magnesium sulfate, and filtered. The residue was purified by silica gel column chromatography using hexane-ethyl acetate (10:1) as an eluent and crystallized from a mixed solution of ethyl acetate and hexane to obtain (as acyl transfer product) 4. 269 (56%) of 4-hydroxy-5-methoxy-2,6,6-trimethyl-2-cyclohepten-1-one (AU222) as colorless plates. Melting point: 71° to 72° C.

IR (KBr, cm$^{-1}$): 3461, 1669, 1103, 1082.

1H-NMR (CDCl$_3$, ppm): 0.99 (3H, s), 1.12 (3H, s), 1.83 (3H, t, J=2 Hz), 2.27 (1H, d, J=12 Hz), 2.50 (1H, d, J=12 Hz), 2.78 (1H, d, J=9 Hz), 2.96 (1H, brs), 3.57 (3H, s), 4.41 (1H, dm, J=9 Hz), 6.57 (1H, m).

EXAMPLE 71

5-Methoxy-4-(4-methoxybenzyloxy)-2,6,6-trimethyl-2-cyclohepten-1-one (AU221) (2.5 g, 7.8 mM) obtained in Example 69 was treated with DDQ according to the procedures described in Example 7 to obtain 1.21 g (78%) of 4-hydroxy-5-methoxy-2,6,6-trimethyl-2-cyclohepten-1-one (AU222) as in Example 70.

EXAMPLE 72

The product (AU222) of Example 71 (1.39 g, 7.0 mM) was treated with 4-nitrobenzoyl chloride as described in Example 17, purified with silica gel column chromatography using benzene-ethyl acetate (20:1) as an eluent and crystallized from a mixed solvent of benzene and hexane to obtain 2.11 g (87%) of 5-methoxy-4-(4-nitrobenzoyloxy)-2,6,6-trimethyl-2-cyclohepten-1-one (AU238 ) as light yellow crystals. Melting point: 136.5° to 138.0° C.

IR (KBr, cm$^{-1}$): 1725, 1682, 1527, 1285, 1124, 1104, 717.

1H-NMR (CDCl$_3$, ppm): 1.11 (3H, s), 1.13 (3H, s), 1.90 (3H, t, J=2 Hz), 2.41 (1H, d, J=13 Hz), 2.65 (1H, d, J=13 Hz), 3.02 (1H, d, J=9 Hz), 3.42 (3H, s), 6.06 (1H, dm, J=9 Hz), 6.49 (1H, m), 8.30 (2H, d, J=9 Hz), 8.34 (2H, d, J=9 Hz).

EXAMPLE 73

The product (AU238) of Example 72 (1.68 g, 4.8 mM) was reduced at the nitro group as described in Example 19 and crystallized from a mixed solvent of ethyl acetate and hexane to obtain 0.79 g (51.1%) of 4-(4-aminobenzoyloxy)-5-methoxy-2,6,6-trimethyl-2-cyclohepten-1-one (AU239) as colorless plates. Melting point: 159° to 161° C.

IR (KBr, cm$^{-1}$): 3476, 3377, 1687, 1602, 1276, 1170, 1114.

1H-NMR (CDCl$_3$, ppm): 1.09 (3H, s), 1.11 (3H, s), 1.87 (3H, t, J=2 Hz), 2.38 (1H, d, J=13 Hz), 2.66 (1H, d, J=13 Hz), 2.98 (1H, d, J=9 Hz), 3.45 (3H, s), 4.11 (2H, br), 5.99 (1H, dm, J=9 Hz), 6.47 (1H, m), 6.67 (2H, d, J=9 Hz), 7.93 (2H, d, J=9 Hz).

EXAMPLE 74

4-Hydroxy-5-methoxy-2,6,6-trimethyl-2-cyclohepten-1-one (AU222) (397 mg, 2 mM) obtained in Example 71 was benzoylated according to the procedures described in Example 6 and crystallized from hexane to obtain 510 mg (84%) of 4-benzoyloxy-5-methoxy-2,6,6-trimethyl-2-cyclohepten-1-one (AU223) as colorless plates. Melting point: 97° to 98° C.

IR (KBr, cm$^{-1}$): 1724, 1676, 1272, 1117, 712.

1H-NMR (CDCl$_3$, ppm): 1.10 (3H, s), 1.12 (3H, s), 1.89 (3H, t, J=2 Hz), 2.40 (1H, d, J=13 Hz), 2.67 (1H, d, J=13 Hz), 3.01 (1H, d, J=9 Hz), 3.45 (3H, s), 6.04 (1H, dm, J=9 Hz), 6.49 (1H, m), 7.48 (2H, m), 7.60 (1H, m), 8.13 (2H, m).

EXAMPLE 75 p-Toluenesulfonic acid (0.3 g) was added to a solution of Saishin N (2.00 g, 11 mM) in acetone (10 ml), and it was stirred overnight at room temperature, diluted with ethyl acetate, washed with a saturated sodium bicarbonate solution and with brine, dried over magnesium sulfate, filtered, and concentrated. The residue was crystallized from hexane to obtain 2.30 g (95.7%) of the intermediate 4,5-O-isopropylidene Saishin N as colorless needles.

Melting point: 65° to 65.5° C.

IR (KBr, cm$^{-1}$): 1664, 1374, 1242, 1091, 877.

1H-NMR (CDCl$_3$, ppm): 1.06 (3H, s), 1.15 (3H, s), 1.41 (3H, s), 1.43
(3H, s), 1.85 (3H, t, J=2 Hz), 2.37 (1H, d, J=12 Hz), 2.47 (1H, d, J=12 Hz), 3.42 (1H, d, J=9 Hz), 4.53 (1H, dm, J=9 Hz), 6.57 (1H, t, J=1 Hz).

To a solution of the above intermediate product (2.24 g, 10 mM) in tetrahydrofuran (5 ml), lithium aluminum hydride (0.3 g, 8 mM) was added under ice-cooling and stirring, and then it was stirred for two hours. Ethyl acetate (5 ml) and water (4 ml) were added to the mixture, which was stirred for two hours and then filtered. The filtrate was concentrated to obtain 1.85 g (82%) of the further intermediate 4,5-O-isopropylidene-2,6,6-trimethyl-2-cyclohepten-1,4,5-triol as a colorless crystalline material.

IR (KBr, $cm^{-1}$): 3365, 1450, 1372, 1240, 1069, 1006.

1H-NMR (CDCl$_3$+D$_2$O, pm): 1.07 (3H, s), 1.12 (3H, s), 1.37 (3H, s), 1.40 (3H, s), 1.48 (1H, dd, J=13, 2 Hz), 1.71 (1H, dd, J=13, 11 Hz), 1.79 (3H, brs), 3.23 (1H, d, J=9 Hz), 4.39 (1H, dm, J=9 Hz), 4.49 (1H, brd, J=11 Hz), 5.56 (1H, m).

2N Hydrochloric acid (5 ml) was added to a mixed solution of the above further intermediate product (2.33 g, 10.3 mM) in methanol (5 ml) and tetrahydrofuran (5 ml) and it was warmed at 40° C. for six hours, diluted with ethyl acetate, washed with a saturated sodium bicarbonate solution and with brine, dried over magnesium sulfate, filtered, concentrated, purified by silica gel column chromatography using benzene-ethyl acetate (3:1) as an eluent, and crystallized from ethyl acetate to obtain 0.99 g (54%) of 2,6,6-trimethyl-2-cycloheptenl,4,5-triol (AU103) as colorless needles. Melting point: 138° to 139° C.

IR (KBr, $cm^{-1}$): 3600–3100, 1447, 1435, 1280, 994.

1H-NMR (DMSO-d$_6$, ppm): 0.95 (3H, s), 0.97 (3H, s), 1.36 (1H, dd, J=13, 3 Hz), 1.47 (1H, dd, J=13, 10 Hz), 1.66 (3H, brs), 2.78 (1H, dd, J=10, 3 Hz; d by the addition of heavy water, J=10 Hz), 3.99 (1H, m; brd by the addition of heavy water, J=10 Hz), 4.26 (1H, m; brd disappeared by the addition of heavy water, J=10 Hz), 4.36 (1H, d, J=3 Hz; disappeared by the addition of heavy water), 4.62 (1H, d, J=3 Hz; disappeared by the addition of heavy water), 4.68 (1H, d, J=4 Hz; disappeared by the addition of heavy water), 5.17 (1H, m).

EXAMPLE 76

4-Methoxybenzaldehyde (3.5 ml, 28 mM) and p-toluenesulfonic acid (0.25 g) were added to a solution of Saishin N (5.0 g, 27 mM) in benzene (60 ml) and it was heated under reflux for an hour, diluted with benzene, washed with a saturated sodium bicarbonate solution, dried over magnesium sulfate, filtered, and concentrated to obtain the intermediate 4,5-O-(4-methoxybenzylidene) Saishin N in a quantitative yield as a partly crystalline product.

IR (KBr, $cm^{-1}$): 1676, 1243, 1093, 1029.

The above intermediate product was reduced by lithium aluminum hydride (1 g, 26 mM) according to the procedures described in Example 75 and purified by silica gel column chromatography using toluene-ethyl acetate (20:1) as an eluent to obtain the further intermediate 4,5-O-(4-methoxybenzylidene)-2,6,6-trimethyl-2-cyclohepten-1,4,5-triol as a partly crystalline product.

IR (KBr, $cm^{-1}$): 3482, 1613, 1516,1248, 1089.

The above further intermediate product was methylated according to the procedures described in Example 69 to form the still further intermediate 4,5-O-(4-methoxybenzylidene)-1-methoxy-2,6,6-trimethyl-2-cyclohepten-4,5-diol, then treated with 80% acetic acid (80 ml) and stirred overnight to hydrolyze and thus remove the 4-methoxy benzylidene group. The reaction solution was concentrated, neutralized with a sodium bicarbonate solution, extracted with ethyl acetate, washed with brine, dried over magnesium sulfate, filtered and concentrated. The residue was purified by silica gel column chromatography using hexane-ethyl acetate (20:1) as an eluent to obtain 2.98 g (55%) of 1-methoxy-2,6,6-trimethyl-2-cyclohepten-4,5-diol (AU110) as a colorless oily material.

IR (KBr, $cm^{-1}$): 3418, 1103, 1002.

1H-NMR (CDCl$_3$+CD$_3$OD, ppm): 1.07 (3H, s), 1.09 (3H, s), 1.51 (1H, dd, J=14, 3 Hz), 1.58 (1H, dd, J=14, 9 Hz), 1.75 (3H, m), 3.07 (1H, d, J=10 Hz), 3.32 (3H, s), 3.84 (1H, brd, J=9 Hz), 4.20 (1H, brd, J=10 Hz), 5.33 (1H, m).

EXAMPLE 77

1-Methoxy-2,6,6-trimethyl-2-cyclohepten-4,5-diol (AU110) (0.3 g, 1.3 mM) obtained in Example 76 was acetylated by a conventional method to obtain 0.41 g (94%) of 4,5-diacetoxy-1-methoxy-2,6,6-trimethyl-2-cycloheptene (AU112) as a colorless oily product.

IR (KBr, $cm^{-1}$): 1746, 1372, 1244, 1102, 1028.

1H-NMR (CDCl$_3$, ppm): 0.95 (3H, s), 1.19 (3H, s), 1.59 (1H, d, J=13 Hz), 1.63 (1H, d, J=13 Hz), 1.76 (3H, brt, J=1 Hz), 2.03 (3H, s), 2.04 (3H, s), 3.33 (3H, s), 3.94 (1H, brd, J=8 Hz), 4.75 (1H, d, J=10 Hz), 5.22 (1H, m), 5.58 (1H, dm, J=10 Hz).

EXAMPLE 78

1-Methoxy-2,6,6-trimethyl-2-cyclohepten-4,5-diol (AU110) (0.35 g, 1.7 mM) obtained in Example 76 was methylated according to the procedures described in Example 69 to obtain 0.325 g (81.4%) of 1,4,5-trimethoxy-2,6,6-trimethyl-2-cycloheptene (AU113) as a colorless oily product.

IR (KBr, $cm^{-1}$): 1446, 1385, 1104.

1H-NMR (CDCl$_3$, ppm): 1.05 (3H, s), 1.07 (3H, s), 1.50 (2H, m), 1.75 (3H, brs), 2.69 (1H, d, J=10 Hz), 3.31 (3H, s), 3.43 (3H, s), 3.49 (3H, s), 3.84 (1H, brd, J=10 Hz), 3.87 (1H, dm, J=10 Hz), 5.30 (1H, m).

EXAMPLE 79

To a solution of 1-methoxy-2,6,6-trimethyl-2-cyclohepten-4,5-diol (AU110) (0.3 g, 1.5 mM) obtained in Example 76 in tetrahydrofuran (3 ml), 55% sodium hydride (0.2 g, 4.6 mM) was added under ice-cooling and stirring. After stirring for an hour, the mixture was treated with benzoyl chloride (0.53 ml, 4.55 mM) and stirred overnight at room temperature. The reaction mixture was poured onto ice-water, diluted with ethyl acetate, washed with brine, dried over magnesium sulfate, filtered, and concentrated. The residue was fractionated by silica gel column chromatography using hexane-ethyl acetate (10:1). From the first eluted portion 0.11 g (17.2%) of 4,5-dibenzoyloxy-1-methoxy-2,6,6-trimethyl-2-cycloheptene (AU114) was obtained as colorless crystals. Melting point: 78° to 80° C.

IR (KBr, $cm^{-1}$): 1724, 1602, 1451, 1279, 1095, 711.

1H-NMR (CDCl$_3$, ppm): 1.06 (3H, s), 1.39 (3H, s), 1.70 (1H, dd, J=14, 2 Hz), 1.80 (1H, dd, J=14, 10 Hz), 1.83 (3H, brs), 3.39 (3H, s), 4.10 (1H, d, J=7 Hz), 5.16 (1H, d, J=10 Hz), 5.43 (1H, m), 6.00 (1H, m), 7.23 (4H, m), 7.38 (2H, m), 7.84 (4H, m). 86 mg (19%) of 5-benzoyloxy-1-methoxy-2,6,6-trimethyl-2-cyclohepten-4-ol (AU115) were obtained as colorless crystals from the successive eluted portion.

1H-NMR (CDCl$_3$, ppm): 1.02 (3H, s), 1.30 (3H, s), 1.61 (1H, dd, J=13, 2 Hz), 1.72 (1H, dd, J=13, 10 Hz), 1.80 (3H, brs), 3.35 (3H, s), 3.91 (1H, d, J=10 Hz), 4.49 (1H, brd, J=10 Hz), 4.84 (1H, d, J=10 Hz), 5.41 (1H, m), 7.46 (2H, m), 7.58 (1H, m), 8.06 (2H, brd, J=9 Hz).

EXAMPLE 80

1-Methoxy-2,6,6-trimethyl-2-cyclohepten-4,5-diol (AU110) (2.73 g, 13.6 mM) obtained in Example 76 was benzoylated as described in Example 6 and crystallized from a mixed solution of hexane and ethyl acetate to obtain 1.01 g (33%) of 4-benzoyloxy-1-methoxy-2,6,6-trimethyl-2-cyclohepten-5-ol (AU145) as colorless needles.

Melting point: 98° to 99° C.

IR (KBr, cm$^{-1}$): 3517, 1694, 1280, 1095, 720.

1H-NMR (CDCl$_3$+D$_2$O, ppm): 1.16 (3H, s), 1.18 (3H, s), 1.61 (1H, dd, J=14, 2 Hz), 1.65 (1H, dd, J=14, 8 Hz), 1.78 (3H, brs), 3.36 (3H, s), 3.46 (1H, d, J=10 Hz), 3.98 (1H, brd, J=8 Hz), 5.32 (1H, m), 5.67 (1H, dm, J=10 Hz), 7.46 (2H, t, J=7 Hz), 7.59 (1H, t, J=7 Hz), 8.06 (1H, d, J=7 Hz).

EXAMPLE 81

4,5-O-(4-Methoxybenzylidene)-2,6,6-trimethyl-2-cyclohepten-1,4,5-triol (918 mg, 3.0 mM) obtained as an intermediate in Example 76 was acetylated by a conventional method to obtain 1.05 g (94.7%) of the acetate intermediate. The acetate intermediate (961 mg, 2.77 mM) was hydrolyzed with 80% acetic acid (5 ml), and purified by silica gel column chromatography to obtain 0.615 g (97.2%) of 1-acetoxy-2,6,6-trimethyl-2-cyclohepten-4,5-diol (AU111) as a colorless oily product.

IR (KBr, cm$^{-1}$): 3444, 1738, 1374, 1240.

1H-NMR (CDCl$_3$, ppm): 1.09 (3H, s), 1.11 (3H, s), 1.49 (1H, dd, J=14, 2 Hz), 1.69 (3H, brs), 1.74 (1H, dd, J=14, 10 Hz), 2.07 (3H, s), 2.48 (1H, d, J=3 Hz; disappeared by the addition of heavy water), 2.29 (1H, d, J=4 Hz; disappeared by the addition of heavy water), 3.14 (1H, dd, J=10, 4 Hz; d by the addition of heavy water, J=10 Hz), 4.30 (1H, brd, J=10 Hz), 5.40 (1H, q, J=1 Hz), 5.50 (1H, brd, J=10 Hz).

EXAMPLE 82

To a solution of 4,5-O-(4-methoxybenzylidene)-2,6,6-trimethyl-2-cyclohepten-1,4,5-triol (1.0 g, 3.29 mM) obtained as an intermediate in Example 76 in tetrahydrofuran (10 ml), 55% sodium hydride (0.2 g) was added under ice-cooling and stirring. After stirring for 90 minutes, benzyl chloride (0.53 ml, 4.6 mM) was added, and the mixture was heated under reflux for 19 hours, diluted with water, extracted with ethyl acetate, washed with brine, dried over magnesium sulfate, filtered, and concentrated. The residue was purified by silica gel column chromatography using hexane-ethyl acetate (40:1) as an eluent to obtain 816 mg (63%) of the 1-benzyl ether intermediate as a colorless oily product. The intermediate product so obtained was hydrolyzed with 80% acetic acid to obtain 266 mg (43.2%) of 1-benzyloxy-2,6,6-trimethyl-2-cyclohepten-4,5-diol (AU116) as a colorless oily product.

IR (KBr, cm$^{-1}$): 3600–3200, 1456, 1094, 745, 697.

1H-NMR (CDCl$_3$+D$_2$O, ppm): 1.01 (3H, s), 1.09 (3H, s), 1.59 (1H, dd, J=14, 2 Hz), 1.68 (1H, dd, J=14, 10 Hz), 1.82 (3H, t, J=2 Hz), 3.10 (1H, d, J=10 Hz), 4.08 (1H, dm, J=9 Hz), 4.21 (1H, brd, J=10 Hz), 4.50 (2H, s), 5.34 (1H, m), 7.33 (5H, m).

EXAMPLE 83

4,5-O-(4-Methoxybenzylidene)-2,6,6-trimethyl-2-cyclohepten-1,4,5-triol (4.98 g, 16.4 mM) obtained in Example 76 was treated with 55% sodium hydride (0.93 g, 21.3 mM) and 1-bromo-3-methyl-2-butene (2.5 ml, 21.3 mM) according to the procedures described in Example 69 to form 4,5-O-(4-methoxybenzylidene)-1-(3-methyl-2-buten-1-yloxy)-2,6,6-trimethyl-2-cycloheptan-4,5-diol as an intermediate, and this was fractionated by silica gel column chromatography using hexane-ethyl acetate (2:1) as an eluent to obtain, upon easy decomposition of the intermediate during such column chromatography procedure, 1.56 g (38%) of 1-(3-methyl-2-buten-1-yloxy)-2,6,6-trimethyl-2-cyclohepten-4,5,-diol (AU143) as a colorless oily product.

IR (KBr, cm$^{-1}$): 3434, 1714, 1450, 1379, 1069.

1H-NMR (CDCl$_3$+D$_2$O, ppm): 1.07 (3H, s), 1.09 (3H, s), 1.52 (1H, dd, J=13, 2 Hz), 1.63 (1H, dd, J=13, 10 Hz), 1.67 (3H, brs), 1.75 (3H, brs), 1.77 (3H, brs), 3.10 (1H, d, J=10 Hz), 3.94 (2H, m), 3.99 (1H, brd, J=10 Hz), 4.25 (1H, dm, J=9 Hz), 5.32 (2H, m).

EXAMPLE 84

The product (AU143) of Example 83 (1.25 g, 4.9 mM) was benzoylated as described in Example 6 and purified by silica gel column chromatography using benzene-ethyl acetate (10:1) as an eluent to obtain 0.52 g (30%) of 4-benzoyloxy-1-(3-methyl-2-buten-1-yloxy)-2,6,6-trimethyl-2-cyclohepten-5-ol (AU144) as a colorless oily product.

IR (KBr, cm$^{-1}$): 3479, 1732, 1715, 1698, 1451, 1272, 712.

1H-NMR (CDCl$_3$+D$_2$O, ppm): 1.15 (3H, s), 1.17 (3H, s), 1.61 (1H, dd, J=13, 2 Hz), 1.70 (3H, s), 1.76 (3H, s), 1.79 (3H, t, J=2 Hz), 3.46 (1H, d, J=10 Hz), 3.98 (2H, m), 4.13 (1H, brd, J=11 Hz), 5.33 (2H, m), 5.67 (1H, dm, J=9 Hz), 7.43 (2H, m), 7.56 (1H, m), 8.06 (2H, m).

EXAMPLE 85

4,5-O-(4-Methoxybenzylidene)-2,6,6-trimethyl-2-cyclohepten-1,4,5-triol (10.0 g, 32.9 mM) obtained as an intermediate in Example 76 was treated with bromoethyl acetate (bromoacetic acid ethyl ester) (5.6ml, 42.6 mM) according to the procedures described in Example 83 to form the acetate intermediate, and then the latter was hydrolyzed with 80.% acetic acid to obtain 1.84 g (21%) of 1-ethoxycarbonylmethoxy-2,6,6-trimethyl-2-cyclohepten-4,5-diol (AU146) as a colorless oily product.

1H-NMR (CDCl$_3$+D$_2$O, ppm): 1.10 (3H, s), 1.12 (3H, s), 1.29 (3H, t, J=7 Hz), 1.63 (2H, m), 1.80 (3H, t, J=2 Hz), 3.10 (1H, d, J=10 Hz), 4.04 (1H, d, J=16 Hz), 4.08 (1H, dm, J=10 Hz), 4.22 (2H, q, J=7 Hz), 5.36 (1H, m).

EXAMPLE 86

The product (AU146) of Example 85 (1.34 g, 3.55 mM) was benzoylated as described in Example 6 and purified by silica gel column chromatography using benzene-ethyl acetate (10:1) as an eluent to obtain 0.66 g (36%) of 5-benzoyloxy-1-ethoxycarbonylmethoxy-2,6,6-trimethyl-2-cyclohepten-4-ol (AU147) as a colorless oily product.

IR (KBr, cm$^{-1}$): 3524, 1751, 1718, 1275, 1118, 712.

1H-NMR (CDCl$_3$, ppm): 1.03 (3H, s), 1.30 (3H, s), 1.30 (3H, t, J=7 Hz), 1.73 (1H, dd, J=14, 2 Hz), 1.79 (1H, d, J=−14 Hz), 182 (1H, dd, J=14, 10 Hz), 1.85 (3H, t, J=2 Hz), 4.00–4.20 (3H, m), 4.23 (2H, q, J=7 Hz), 4.46 (1H, brd, J=10 Hz), 4.86 (1H, d, J=10 Hz), 5.45 (1H, m), 7.46 (2H, t, J=7 Hz), 7.58 (1H, t, J=7 Hz), 8.07 (2H, d, J=7 Hz).

EXAMPLE 87

4,5-O-(4-Methoxybenzylidene)-2,6,6-trimethyl-2-cyclohepten-1,4,5-triol (5.0 g, 16.4 mM) obtained as an intermediate in Example 76 was treated with 4-nitrocinnamoyl chloride according to the procedures described in Example 17, and the resulting acylate intermediate was then hydrolyzed with 80% acetic acid and crystallized from ethyl acetate to obtain 2.54 g (83%) of 1-(4-nitrocinnamoxyloxy)-2,6,6-trimethyl-2-cyclohepten-4,5-diol (AU149) as yellow needles. Melting point: 152.5° to 154° C.

IR (KBr, cm$^{-1}$): 3379, 1711, 1518, 1342, 844.

1H-NMR (CDCl$_3$, ppm): 1.12 (3H, s), 1.16 (3H, s), 1.59 (1H, dd, J=14, 2 Hz), 1.75 (3H, brs), 1.84 (1H, dd, J=14, 10 Hz), 3.18 (1H, d, J=10 Hz), 4.35 (1H, brd, J=10 Hz), 5.46 (1H, m), 5.66 (1H, brd, J=10 Hz), 6.57 (1H, d, J=16 Hz), 7.69 (2H, d, J=9 Hz), 7.73 (1H, d, J=16 Hz), 8.26 (2H, d, J=9 Hz).

EXAMPLE 88

The product (AU149) of Example 87 (2.44 g, 6.75 mM) was benzoylated as described in Example 6 and fractionated by silica gel column chromatography using hexane-ethyl acetate (10:1) as an eluent. The first eluted portion was crystallized from a mixed solvent of ethyl acetate and hexane to obtain 1.36 g (43%) of 4-benzoyloxy-1-(4-nitrocinnamoyloxy)-2,6,6-trimethyl-2-cyclohepten-5-ol (AU405) as light yellow needles. Melting point: 156.5° to 157.5° C.

IR (KBr, cm$^{-1}$): 3500, 1732, 1715, 1682, 1668, 1580, 1471, 1296, 763.

1H-NMR (CDCl$_3$, ppm): 1.17 (3H, s), 1.26 (3H, s), 1.69 (1H, dd, J=14, 2 Hz), 1.79 (3H, brs), 1.92 (1H, dd, J=14, 10 Hz), 2.19 (1H, d, J=5 Hz; disappeared by the addition of heavy water), 3.55 (1H, dd, J=10, 5 Hz; d by the addition of heavy water, J=10 Hz), 5.46 (1H, m), 5.78 (2H, m), 6.59 (1H, d, J=16 Hz), 7.58 (5H, m), 7.75 (1H, d, J=16 Hz), 8.09 (2H, m), 8.28 (2H, m).

The successive eluted portion was crystallized from a mixed solvent of ethyl acetate and hexane to obtain (per acyl transfer reaction) 0.35 g (11%) of 5-benzoyloxy-1-(4-nitrocinnamoyloxy)-2,6,6-trimethyl-2-cyclohepten-4-ol (AU406) as light yellow needles.

Melting point: 179° to 181° C.

IR (KBr, cm$^{-1}$): 3517, 1707, 1639, 1518, 1340, 1280, 716.

1H-NMR (CDCl$_3$, ppm): 1.04 (3H, s), 1.36 (3H, s), 1.69 (1H, dd, J=13, 2 Hz), 1.81 (3H, brs), 1.99 (1H, d, J=13, 10 Hz), 2.02 (1H, d, J=6 Hz; disappeared by the addition of heavy water), 4.61 (1H, m; brd by the addition of heavy water, J=9 Hz), 4.99 (1H, d, J=10 Hz), 5.56 (1H, m), 5.72 (H, brd, J=10 Hz), 6.60 (1H, d, J=16 Hz), 7.61 (5H, m) 7.77 (1H, d, J=16 Hz), 8.10 (2H, d, J=8 Hz), 8.27 (2H, d, J=8 Hz).

EXAMPLE 89

4,5-O-(4-Methoxybenzylidene)-2,6,6-trimethyl-2-cyclohepten-1,4,5-triol (2.42 g, 8.0 mM) obtained as an intermediate in Example 76 was benzoylated as described in Example 6 to obtain a crude benzoate intermediate.

1H-NMR (CDCl$_3$, ppm): 1.17 (3H, s), 1.28 (3H, s), 1.68 (1H, dd, J=14, 1 Hz), 1.82 (3H, brs), 1.92 (1H, dd, J=14, 10 Hz), 3.56 (1H, d, J=9 Hz), 3.82 (3H, s), 4.65 (1H, dm, J=9 Hz), 5.82 (2H, m), 5.99 (1H, s), 6.92 (2H, d, J=9 Hz), 7.42 (2H, d, J=9 Hz), 7.46 (2H, m), 7.59 (1H, m), 8.07 (2H, m).

The above crude benzoate intermediate was hydrolyzed with 80% acetic acid (13 ml), purified by silica gel column chromatography using hexane-ethyl acetate (2:1) as an eluent and crystallized from a mixed solvent of ethyl acetate and hexane to obtain 1.46 g (63%) of 1-benzoyloxy-2,6,6-trimethyl-2-cyclohepten-4,5-diol (AU229) as colorless plates. Melting point: 94° to 96° C.

IR (KBr, cm$^{-1}$): 3600–3200, 1716, 1281, 1115, 1071, 713.

1H-NMR (CDCl$_3$, ppm): 1.11 (3H, s), 1.18 (3H, s), 1.64 (1H, dd, J=14, 2 Hz), 1.80 (3H, t, J=2 Hz), 1.87 (1H, dd, J=14, 10 Hz), 2.61 (1H, brs; disappeared by the addition of heavy water), 2.83 (1H, brs; disappeared by the addition of heavy water), 3.21 (1H, dd, J=9, 4 Hz; d by the addition of heavy water, J=9 Hz), 3.87 (1H, brd, J=9 Hz), 5.46 (1H, m),5.76 (1H, brd, J=10 Hz), 7.46 (2H, m), 7.58 (1H, m), 8.05 (2H, m).

EXAMPLE 90

To a solution of 5-hydroxy-4-(4-methoxybenzyloxy)-2,6,6-trimethyl-2-cyclohepten-1-one (AUM09) (30.4 g, 0.1M) obtained in Example 1 in tetrahydrofuran (200 ml), dihydropyran (43 ml, 0.5M) and p-toluenesulfonic acid (0.5 g) were added and it was stirred for four hours at 0° C., concentrated, diluted with ethyl acetate, washed with a saturated sodium bicarbonate solution, dried over magnesium sulfate, filtered, and concentrated to obtain 54.7 g of crude methoxybenzyloxy)-5-tetrahydropyranyloxy-2,6,6-trimethyl-2-cyclohepten-1-one as an intermediate.

IR (KBr, cm$^{-1}$): 1671, 1514, 1249, 1034, 819.

Sodium borohydride (7 g, 0.19M) was added to a solution of the above intermediate product in methanol (200 ml) at 0° C., and it was stirred for four hours, then concentrated, diluted with ethyl acetate, washed with brine, dried over magnesium sulfate, filtered, and concentrated. The residue was purified by silica gel column chromatography using hexane-ethyl acetate (10:1) to obtain 28.3 g of 4-(4-methoxybenzyloxy)-5-tetrahydropyranyloxy-2,6,6-trimethyl-2-cyclohepten-1-ol as a colorless oily further intermediate product.

IR (KBr, cm$^{-1}$) 3444, 1613, 1514, 1248, 1032, 820.

The above further intermediate product (4.69 g, 12 mM) was benzoylated according to the procedures described in Example 6, purified by silica gel column chromatography using hexane-ethyl acetate (10:1) as an eluent to obtain 5.0 g of a colorless oily product, i.e. 1-benzoyloxy-4-(4-methoxybenzyloxy-5-tetrahydropyranyloxy-2,6,6-trimethyl-2-cycloheptene, as a still further intermediate product, which was dissolved in methanol (30 ml), treated with p-toluenesulfonic acid (0.1 g), stirred for 30 minutes, and concentrated. The residue was diluted with ethyl acetate, washed with a saturated sodium bicarbonate solution, dried over magnesium sulfate, filtered, and concentrated. The residue was crystallized from a mixed solution of ethyl acetate and hexane to obtain 2.30 g (46.7%) of another intermediate product, 1-benzoyloxy-4-(4-methoxybenzyloxy)-2,6,6-trimethyl-2-cyclohepten-5-ol, as colorless prisms. Melting point: 106.5° to 107° C.

1H-NMR (CDCl$_3$, ppm): 1.11 (3H, s), 1.17 (3H, s), 1.60 (1H, dd, J=13, 1 Hz), 1.84 (4H, m), 3.21 (1H, brs; disappeared by the addition of heavy water), 3.23 (1H, d, J=10 Hz), 3.82 (3H, s), 4.14 (1H, dm, J=10 Hz), 4.43 (1H, d, J=11 Hz), 4.70 (1H, d, J=11 Hz), 5.50 (1H, m), 5.77 (1H, brd, J=11 Hz), 6.90 (2H, d, J=9 Hz), 7.29 (2H, d, J=9 Hz), 7.46 (2H, m), 7.59 (1H, m), 8.06 (2H, m).

The above product (820 mg, 2 mM) was benzoylated again and purified by silica gel column chromatography using hexane-benzene (1:1) and benzene as an eluent to obtain 740 mg (72%) of a colorless oily product, i.e. 1,5-dibenzoyloxy-4-(4-methoxybenzyloxy)-2,6,6-trimethyl-2-cycloheptene, as still another intermediate product. The product so obtained was treated with DDQ according to the procedures described in Example 7, purified by silica gel column chromatography using hexane-ethyl acetate (10:1) as an eluent and crystallized from a mixed solvent of hexane-ethyl acetate to obtain 2.30 g (46.7%) of 1,5-dibenzoyloxy-2,6,6-trimethyl-2-cyclohepten-4-ol (AU228) as colorless prisms. Melting point: 142° to 143.5° C.

IR (KBr, cm$^{-1}$): 3503, 1719, 1707,1285, 709.

1H-NMR (CDCl$_3$, ppm): 1.03 (3H, s), 1.40 (3H, s), 1.75 (1H, dd, J=14, 2 Hz), 1.86 (3H, t, J=2 Hz), 1.90 (1H, brs; disappeared by the addition of heavy water), 2.01 (1H, dd, J=14, 10 Hz), 4.63 (1H, brd, J=9 Hz), 4.97 (1H, d, J=9 Hz), 5.55 (1H, m), 5.84 (1H, brd, J=10 Hz), 7.47 (4H, m), 7.58 (2H, m), 8.09 (4H, m).

EXAMPLE 91

4-(4-Methoxybenzyloxy)-5-tetrahydropyranyloxy-2,6,6-trimethyl-2-cyclohepten-1-ol (28.3 g) obtained as an intermediate in Example 90 was acetylated by a conventional method to form 1-acetoxy-4-(4-methoxybenzyloxy)-5-tetrahydropyranyloxy-2,6,6-trimethyl-2-cycloheptene as an intermediate, and this was dissolved in methanol (80 ml) which was treated with p-toluene sulfonic acid (0.2 g) and stirred for an hour at room temperature, concentrated, diluted with ethyl acetate, washed with a saturated sodium bicarbonate solution, dried over magnesium sulfate, filtered, and concentrated. The residue was purified by silica gel column chromatography using hexane-ethyl acetate (20:1) as an eluent to obtain 17.4 g of the further intermediate 1-acetoxy-4-(4-methoxybenzyloxy)-2,6,6-trimethyl-2-cyclohepten-5-ol as a colorless oily product.

1H-NMR (CDCl$_3$+D$_2$O, pm): 1.08 (3H, s), 1.10 (3H, s), 1.43 (1H, dd, J=14, 2 Hz), 1.62 (1H, m), 1.70 (3H, brs), 2.08 (3H, s), 3.16 dd, J=10, 2 Hz), 3.81 (3H, s), 4.18 (1H, dm, J=10 Hz), 4.39 (1H, d, J=11 Hz), 4.47 (1H, d, J=11 Hz), 5.43 (1H, m), 5.50 (1H, brd, J=11 Hz), 6.89 (2H, d, J=8 Hz), 7.26 (2H, d, J=8 Hz).

A solution of the above product in tetrahydrofuran (80 ml) was methylated according to the procedures described in Example 69 and purified by silica gel column chromatography using hexane-ethyl acetate (30:1) as an eluent to obtain the still further intermediate 1-acetoxy-5-methoxy-4-(4-methoxybenzyloxy)-2,6,6-trimethyl-2-cycloheptene as a colorless oily product.

1H-NMR (CDCl$_3$, ppm): 1.06 (3H, s), 1.09 (3H, s), 1.45 (1H, dd, J=14, 2 Hz), 1.68 (3H, brs), 1.73 (1H, dd, J=14, 10 Hz), 2.07 (3H, s), 2.82 (1H, dd, J=10 Hz), 3.54 (3H, s), 3.81 (3H, s), 4.13 (1H, dm, J=10 Hz), 4.57 (1H, d, J=11 Hz), 4.65 (1H, d, J=11 Hz), 5.45 (2H, m), 6.88 (2H, d, J=8 Hz), 7.30 (2H, d, J=8 Hz).

The above product was dissolved in methanol (30 ml), treated with a solution (1 ml) of 28% sodium methoxide in methanol, left to stand overnight at room temperature, treated with dilute hydrochloric acid, extracted with ethyl acetate, washed with brine, dried over magnesium sulfate, filtered, and concentrated to obtain another intermediate, 5-methoxy-4-(4-methoxybenzyloxy)-2,6,6-trimethyl-2-cyclohepten-1-ol. The product was dissolved in methylene chloride (50 ml), treated with activated manganese dioxide (30 g), stirred at room temperature overnight, and filtered. The filtrate was concentrated and the residue was purified by silica gel column chromatography using hexane-ethyl acetate (10:1) as an eluent to obtain 7.64 g (24%) of 5-methoxy-4-(4-methoxybenzyloxy)-2,6,6-trimethyl-2-cyclohepten-1-one (AU221) as obtained in Example 69.

EXAMPLE 92

To a solution of 5-benzoyloxy-4-(4-methoxybenzyloxy)-2,6,6-trimethyl-2-cyclohepten-1-one (AU182) (2.31 g, 5.6 mM) obtained in Example 6 in ethanol (10 ml), sodium borohydride (0.11 g, 2.8 mM) was added with stirring at room temperature and it was stirred for a further hour. The mixture was treated with ice-water, stirred for ten minutes, then extracted with ethyl acetate, washed with brine, dried over magnesium sulfate, filtered, concentrated, and purified by silica gel column chromatography using benzene-ethyl acetate (20:1) as an eluent to obtain 1.52 g (66%) of 5-benzoyloxy-4-(4-methoxybenzyloxy)-2,6,6-trimethyl-2-cyclohepten-1-ol (AU184) as a colorless oily product.

IR (KBr, cm$^{-1}$): 3474, 1719, 1514, 1274, 1250, 1118.

1H-NMR (CDCl$_3$, ppm): 1.02 (3H, s), 1.38 (3H, s), 1.74 (1H, dd, J=14, 1 Hz), 1.86 (3H, brs), 2.01 (1H, dd, J=14, 11 Hz), 2.09 (1H, d, J=7 Hz), 3.88 (3H, s), 4.63 (1H, br), 4.93 (1H, d, J=10 Hz), 5.55 (1H, m), 5.83 (1H, brd, J=11 Hz), 6.95 (2H, d, J=9 Hz), 7.47 (2H, m), 7.59 (1H, m), 8.06 (3H, m).

EXAMPLE 93

The product (AU184) of Example 92 (2.0 g, 4.87 mM) was acetylated by a conventional method to obtain 1.63 g (74%) of 1-acetoxy-5-benzoyloxy-4-(4-methoxybenzyloxy)-2,6,6-trimethyl-2-cycloheptene (AU135) as a colorless oily product.

1H-NMR (CDCl$_3$, ppm): 1.02 (3H, s), 1.27 (3H, s), 1.55 (1H, dd, J=14, 2 Hz), 1.74 (3H, t, J=2 Hz), 1.88 (1H, dd, J=14, 11 Hz), 2.09 (3H, s), 3.74 (3H, s), 4.24 (1H, dm, J=10 Hz), 4.34 (1H, d, J=12 Hz), 4.52 (1H, d, J=12 Hz), 5.01 (1H, d, J=10 Hz), 5.56 (2H, m), 6.65 (2H, d, J=9 Hz), 6.96 (2H, d, J=9 Hz), 7.46 (2H, m), 7.58 (1H, m), 8.05 (1H, m).

The product (AU135) (1.62 g, 3.58 mM) was treated with DDQ according to the procedures described in Example 7, purified by silica gel column chromatography using benzene-hexane (5:1), and crystallized from hexane to obtain 0.69 g (58%) of 1-acetoxy-5-benzoyloxy-2,6,6-trimethyl-2-cyclohepten-4-ol (AU137) as colorless needles. Melting point: 113° to 114.5° C.

IR (KBr, cm$^{-1}$): 3541, 3458, 1734, 1717, 1273, 1249, 1116, 712.

1H-NMR (CDCl$_3$, ppm): 1.02 (3H, s), 1.32 (3H, s), 1.58 (1H, dd, J=14, 2 Hz), 1.75 (3H, brs), 1.88 (1H, dd, J=14, 11 Hz), 2.10 (3H, s), 4.55 (1H, brd, J=10 Hz), 4.90 (1H, d, J=10 Hz), 5.49 (1H, m), 5.57 (1H, brd, J=11 Hz), 7.47 (2H, m), 7.59 (1H, m), 8.08 (2H, m).

EXAMPLE 94

5-Benzoyloxy-4-=(4-methoxybenzyloxy)-2,6,6-trimethyl-2-cyclohepten-1-ol (AU184) (3.0 g, 7.3 mM) obtained in Example 92 was methylated according to the procedures described in Example 69 and purified by silica gel column chromatography using hexane-ethyl acetate (20:1) as an eluent to obtain 1.01 g (33%) of 5-benzoyloxy-1-methoxy-4-(4-methoxybenzyloxy)-2,6,6-trimethyl-2-cycloheptene (AU136) as a colorless oily product.

IR (KBr, cm$^{-1}$): 1723, 1613, 1514, 1271, 711.

1H-NMR (CDCl$_3$, ppm): 1.01 (3H, s), 1.24 (3H, s), 1.59 (1H, dd, J=13, 2 Hz), 1.70 (1H, dd, J=13, 10 Hz), 1.80 (3H, brs), 3.33 (3H, s), 3.74 (3H, s), 3.90 (1H, brd, J=10 Hz), 4.19 (1H, dm, J=10 Hz), 4.33 (1H, d, J=12 Hz), 4.52 (1H, d, J=12 Hz), 4.96 (1H, d, J=10 Hz), 5.48 (1H, m), 6.66 (2H, d, J=9 Hz), 6.97 (2H, d, J=9 Hz), 7.45 (2H, m), 7.56 (1H, m), 8.08 (2H, m).

EXAMPLE 95

5-methoxy-4-(4-methoxybenzyloxy)-2,6,6-trimethyl-2-cyclohepten-1-ol (980 mg, 3 mM) obtained as an intermediate in Example 91 was treated with benzoyl chloride (0.38 ml, 3.3 mM) according to the procedures described in Example 17 and purified by silica gel column chromatography using hexane-ethyl acetate (50:1) as an eluent to obtain 715 mg of the intermediate 1-benzoyloxy-5-methoxy-4-(4-methoxybenzyloxy)-2,6,6-trimethyl-2-cycloheptene as a colorless oily product.

1H-NMR (CDCl$_3$, ppm): 1.08 (3H, s), 1.15 (3H, s), 1.58 (1H, dd, J=14, 2 Hz), 1.79 (3H, brs), 1.86 (1H, dd, J=14, 11 Hz), 2.87 (1H, d, J=10 Hz), 3.57 (3H, s), 3.81 (3H, s), 4.21 (1H, brd, J=10 Hz), 4.61 (1H, d, J=1 Hz), 4.68 (1H, d, J=11 Hz), 4.68 (1H, d, J=11 Hz), 5.53 (1H, m), 5.72 (1H, brd, J=11 Hz), 6.88 (2H, d, J=9 Hz), 7.32 (2H, d, J=9 Hz), 7.47 (2H, m), 7.55 (1H, m), 8.05 (2H, m).

The above intermediate product (687 mg, 1.6 mM) was treated with DDQ according to the procedures described in Example 7, purified by silica gel column chromatography using benzene-ethyl acetate (20:1), and crystallized from a mixed solvent of ethyl acetate and hexane to obtain 197 mg (40%) of 1-benzoyloxy-5-methoxy-2,6,6-trimethyl-2-cyclohepten-4-ol (AU227) as colorless plates. Melting point: 82.5° to 83.5° C.

IR (KBr, cm$^{-1}$): 3488, 1716, 1282, 1099, 713.

1H-NMR (CDCl$_3$, ppm): 1.09 (3H, s), 1.14 (3H, s), 1.60 (1H, dd, J=14, 2 Hz), 1.80 (3H, t, J=2 Hz), 1.88 (1H, dd, J=14, 10 Hz), 2.73 (1H, brs; disappeared by the addition of heavy water), 2.75 (1H, d, J=10 Hz), 3.57 (3H, s), 4.40 (1H, dm, J=10 Hz), 5.52 (1H, m), 5.75 (1H, brd, J=10 Hz), 7.45 (2H, m), 7.58 (1H, m), 8.05 (2H, m).

EXAMPLE 96

To a solution of Saishin N (9.2 g, 50 mM) in methanol (700 ml), p-toluenesulfonic acid (0.4 g) was added and it was heated under reflux for five hours, diluted with ethyl acetate, washed with a saturated sodium bicarbonate solution and with brine, dried over magnesium sulfate, filtered, and concentrated. The residue was fractionated by silica gel column chromatography using benzene-acetone (30:1 to 10:1) as an eluent. The first eluted portion was crystallized from hexane to obtain 3.27 g (33%) of 1-methoxy-2,6,6-trimethyl-8-oxabicyclo[3.2.1]oct-2-en-4-ol (AU152) as colorless needles. Melting point: 52° to 54° C.

IR (KBr, cm$^{-1}$): 3455, 1452, 1277, 1178.

1H-NMR (CDCl$_3$+D$_2$O, ppm): 1.26 (3H, s), 1.29 (3H, s), 1.67 (3H, t, J=2 Hz), 1.81 (2H, s), 3.36 (3H, s), 3.92 (1H, dd, J=5, 2 Hz), 4.82 (1H, m), 5.44 (1H, m).

13C-NMR (CDCl$_3$, ppm): 16.35 (q), 26.37 (q), 33.69 (q), 40.69 (s), 50.45 (t), 51.43 (q), 70.00 (d), 85.29 (d), 108.19 (s), 126.27 (d), 139.35 (s).

The successive eluted portion was crystallized from hexane to obtain (per acyl transfer reaction) 1.41 g (14%) of 1-methoxy-3,3,7-trimethyl-8-oxabicyclo[3.2.1]oct-6-en-4-ol (AU153) as colorless needles. Melting point: 82.5° to 83.5° C.

IR (KBr, cm$^{-1}$): 3471, 1335, 1158, 1005.

1H-NMR (CDCl$_3$+D$_2$O, ppm): 0.95 (3H, s), 1.06 (3H, s), 1.62 (2H, s), 1.76 (3H, brs), 3.30 (3H, s), 3.71 (1H, d, J=4 Hz), 4.56 (1H, m), 6.00 (1H, m).

13C-NMR (CDCl$_3$, ppm): 12.52 (q), 24.53 (q), 33.58 (q), 34.32 (s), 41.67 (t), 50.10 (q), 73.80 (d), 78.90 (d), 110.69 (s), 127.86 (d), 142.51 (s).

EXAMPLE 97

1-Methoxy-3,3,7-trimethyl-8-oxabicyclo[3.2.1]oct-6-en-4-ol (AU153) (396 mg, 2 mM) obtained in Example 96 was acetylated by a conventional method and crystallized from a mixed solution of methanol and water to obtain 299 mg (62%) of 4-acetoxy-1-methoxy-3,3,7-trimethyl-8-oxabicyclo[3.2.1]oct-6-ene (AU159) as colorless needles. Melting point: 54° to 55° C.

IR (KBr, cm$^{-1}$): 1735, 1244, 1163, 1020.

1H-NMR (CDCl$_3$, ppm): 0.97 (3H, s), 1.02 (3H, s), 1.63 (1H, d, J=14 Hz), 1.72 (1H, d, J=14 Hz), 1.77 (3H, brs), 2.07 (3H, s), 3.30 (3H, s), 4.61 (1H, m), 4.90 (1H, d, J=4 Hz), 5.89 (1H, m).

EXAMPLE 98

To a solution of 4-benzyloxy-5-hydroxy-2,6,6-trimethyl-2-cyclohepten-1-one (AU156) (412 mg, 1.5 mM) obtained in Example 2 in methanol (20 ml), concentrated sulfuric acid (0.1 ml) was added and it was heated under reflux for three hours. The reaction mixture was diluted with ethyl acetate, washed with a saturated sodium bicarbonate solution and with brine, dried over magnesium sulfate, and purified by silica gel column chromatography using hexane-ethyl acetate (20:1) as an eluent to obtain 144 mg (33%) of 1-methoxy-4-benzyloxy-2,6,6-trimethyl-8-oxabicyclo[3.2.1]oct-2-ene (AU157) as a colorless oily product.

IR (KBr, cm$^{-1}$): 1720, 1453, 1272, 1214, 1060.

1H-NMR (CDCl$_3$, ppm): 1.24 (3H, s), 1.30 (3H, s), 1.66 (3H, brs), 1.81 (2H, s), 3.35 (3H, s), 4.02 (1H, dd, J=5, 2 Hz), 4.55 (3H, m), 5.52 (1H, m), 7.33 (5H, m).

EXAMPLE 99

To a solution of 5-hydroxy-4-(4-nitrobenzoyloxy)-2,6,6-trimethyl-2-cyclohepten-1-one (AU212) (2.00 g, 6.0 mM) obtained in Example 44 in methanol (30 ml), p-toluenesulfonic acid (0.1 g) was added. The mixture was heated under reflux for three hours and concentrated to a half amount. The separated crystal product was collected by filtration and re-crystallized from methanol to obtain 1.16 g (74%) of 1-methoxy-4-(4-nitrobenzoyloxy)-2,6,6-trimethyl-8-oxabicyclo[3.2.1]oct-2-ene (AU244) as colorless needles. Melting point: 140° to 141° C.

IR (KBr, cm$^{-1}$): 1713, 1528, 1348, 1288, 1277, 714.

1H-NMR (CDCl$_3$, ppm): 1.28 (3H, s), 1.33 (3H, s), 1.74 (3H, t, J=2 Hz), 1.89 (2H, s), 3.41 (3H, s), 4.25 (1H, dd, J=5, 2 Hz), 5.49 (1H, m), 6.05 (1H, m), 8.19 (2H, d, J=9 Hz), 8.31 (2H, d, J=9 Hz).

EXAMPLE 100

The product (AU244) of Example 99 (690 mg, 2 mM) was reduced at the nitro group as described in Example 19 and crystallized from a mixed solvent of ethyl acetate and hexane to obtain 390 mg (61%) of 4-(4-aminobenzoyloxy)-1-methoxy-2,6,6-trimethyl-8-oxabicyclo [3.2.1]oct-2-ene (AU245) as light yellow prisms. Melting point: 117.5° to 119° C.

IR (KBr, cm$^{-1}$): 3452, 3418, 3362, 3247, 1702, 1641, 1599, 1270, 1170.

1H-NMR (CDCl$_3$, ppm): 1.25 (3H, s), 1.33 (3H, s), 1.71 (3H, t, J=2 Hz), 1.87 (2H, s), 3.40 (3H, s), 4.08 (2H, brs), 4.21 (1H, dd, J=5, 2 Hz), 5.48 (1H, m), 5.96 (1H, m), 6.64 (2H, d, J=9 Hz), 7.83 (2H, d, J=9 Hz).

EXAMPLE 101

5-Hydroxy-4-(4-nitrobenzoyloxy)-2,6,6-trimethyl-2-cyclohepten-1-one (1.00 g, 3.0 mM) obtained in Example 44 was treated with ethanol (20 ml) according to the procedures described in Example 99 and crystallized from a mixed solution of ethyl acetate and hexane to obtain 0.7 g (64%) of 1-ethoxy-4-(4-nitrobenzoyloxy)-2,6,6-trimethyl-8-oxabicyclo[3.2.1]oct-2-ene (AU246) as light yellow flakes. Melting point: 144° to 146° C.

IR (KBr, cm$^{-1}$): 1713, 1527, 1346, 1287, 1277, 714.

1H-NMR (CDCl$_3$, ppm): 1.25 (3H, t, J=7 Hz), 1.27 (3H, s), 1.33 (3H, s), 1.74 (3H, t, J=2 Hz), 1.89 (1H, d, J=12 Hz), 1.92 (1H, d, J=12 Hz), 3.54 (1H, m), 3.74 (1H, m), 4.23 (1H, dd, J=5, 2 Hz), 5.49 (1H, m), 6.04 (1H, m), 8.19 (2H, d, J=9 Hz), 8.31 (2H, d, J=9 Hz).

EXAMPLE 102

The product (AU246) of Example 101 (578 mg, 1.6 mM) was reduced at the nitro group according to the procedures described in Example 19 and crystallized from a mixed solvent of ethyl acetate and hexane to obtain 293 mg (55%) of 4-(4-aminobenzoyloxy)-1-ethoxy-2,6,6-trimethyl-8-oxabicyclo[3.2.1]oct-2-ene (AU247) as orange plates. Melting point: 130.5° to 131.5° C.

IR (KBr, cm$^{-1}$): 3444, 3359, 3244, 1698, 1606, 1310, 1267, 1171, 1100.

1H-NMR (CDCl$_3$, ppm): 1.24 (3H, t, J=7 Hz), 1.24 (3H, s), 1.32 (3H, s), 1.70 (3H, t, J=2 Hz), 1.86 (1H, d, J=12 Hz), 1.91 (1H, d, J=12 Hz), 3.54 (1H, m), 3.74 (1H, m), 4.08 (2H, brs), 4.19 (1H, dd, J=5, 2 Hz), 5.47 (1H, m), 5.96 (1H, m), 6.64 (2H, d, J=9 Hz), 7.82 (2H, d, J=9 Hz).

EXAMPLE 103

5-Hydroxy-4-(4-nitrobenzoyloxy)-2,6,6-trimethyl-2-cyclohepten-1-one (AU212) (1.00 g, 3.0 mM) obtained in Example 44 was treated with a mixed solution of ethylene glycol (5 ml) and tetrahydrofuran (5 ml) according to the procedures described in Example 99 and crystallized from a mixed solvent of ethyl acetate and hexane to obtain 0.355 g (31%) of 1-(2-hydroxyethoxy)-4-(4-nitrobenzoyloxy)-2,6,6-trimethyl-8-oxabicyclo[3.2.1]oct-2-ene (AU248) as colorless fine crystals. Melting point: 166° to 167.5° C.

IR (KBr, cm$^{-1}$): 3446, 1713, 1527, 1346, 1277, 715.

1H-NMR (CDCl$_3$, ppm): 1.28 (3H, s), 1.33 (3H, s), 1.77 (3H, t, J=2 Hz), 1.91 (1H, d, J=12 Hz), 1.96 (1H, d, J=12 Hz), 2.58 (1H, brs), 3.76 (4H, m), 4.27 (1H, dd, J=5, 2 Hz), 5.51 (1H, m), 6.04 (1H, m), 8.19 (2H, d, J=9 Hz), 8.31 (2H, d, J=9 Hz).

EXAMPLE 104

The product (AU248) of Example 103 (367 mg, 0.97 mM) was reduced at the nitro group according to the procedures described in Example 19 and purified by silica gel column chromatography using hexane-ethyl acetate (3:1) to obtain 4-(4-aminobenzoyloxy)-1-(2-hydroxyethoxy)-2,6,6-trimethyl-8-oxabicyclo[3.2.1.]oct-2-ene (Au249) as a colorless oily product.

1H-NMR (CDCl$_3$, ppm): 1.26 (3H, s), 1.33 (3H, s), 1.73 (3H, t, J=2 Hz), 1.86 (1H, d, J=12 Hz), 1.95 (1H, d, J=12 Hz), 2.73 (1H, brs), 3.76 (4H, m), 4.11 (2H, brs), 4.23 (1H, dd, J=5, 2 Hz), 5.50 (1H, m), 5.96 (1H, m), 6.64 (2H, d, J=9 Hz), 7.82 (2H, d, J=9 Hz).

The product (AU249) was dissolved in ethyl acetate (10 ml) and treated with 4N hydrogen chloride in ethyl acetate and a small amount of methanol and was solidified in a refrigerator to obtain 160 mg (44%) of a hydrochloride thereof (AU249 hydrochloride) as a colorless powder. Melting point 157° to 159° C.

IR (KBr, cm$^{-1}$): 3600–3300, 3000–2500, 1716, 1311, 1276, 1177, 1120.

EXAMPLE 105

To a solution of 5-hydroxy-4-(4-tetrahydropyranyloxy cinnamolyoxy)-2,6,6-trimethyl-2-cyclohepten-1-one (1.0 g, 2.4 mM) obtained as an intermediate in Example 65 in methanol (60 ml), p-toluene sulfonic acid (25 mg) was added. The mixture was stirred at room temperature for a day, concentrated, diluted with ethyl acetate, washed with a saturated sodium bicarbonate solution and with brine, dried over magnesium sulfate, filtered, and concentrated. The residue was crystallized from a mixed solvent of ethyl acetate and hexane to obtain 0.35 g (42%) of 4-(4-hydroxy cinnamoyloxy)-1-methoxy-2-6,6-trimethyl-8-oxabicyclo[3.2.1]oct-2-ene (AU508) as colorless crystals. Melting point: 143° to 145° C.

IR (KBr, cm$^{-1}$): 3378, 1677, 1629, 1599, 1278, 1205, 1170.

1H-NMR (CDCl$_3$, ppm): 1.24 (3H, s), 1.31 (3H, s), 1.72 (3H, t, J=2 Hz), 1.88 (2H, s), 3.40 (3H, s), 4.20 (1H, dd, J=6, 2 Hz), 5.46 (1H, t, J=2 Hz), 5.89 (1H, m), 6.26 (1H, d, J=16 Hz), 6.87 (2H, d, J=9 Hz), 7.18 (1H, brs), 7.42 (2H, d, J=9 Hz), 7.63 (1H, d, J=16 Hz).

EXAMPLE 106

5-Hydroxy-4-(3-methoxy-4-tetrahydropyranyloxy cinnamoyloxy)-2,6,6-trimethyl-2-cyclohepten-1-one (1.94 g, 4.36 mM) obtained as an intermediate in Example 61 was treated according to the procedures described in Example 105 and crystallized from hexane-ethyl acetate to obtain 0.74 g (45%) of 4-(4-hydroxy-3-methoxycinnamoyloxy)-1-methoxy-2,6,6-trimethyl-8-oxabicyclo[3.2.1]oct-2-ene (AU417) as colorless crystals.

IR (KBr, cm$^{-1}$): 3531, 3434, 1702, 1629, 1603, 1513, 1264, 1172.

1H-NMR (CDCl$_3$, ppm): 1.26 (3H, s), 1.29 (3H, s), 1.71 (3H, t, J=2 Hz), 1.86 (2H, s), 3.39 (3H, s), 3.94 (3H, s), 4.19 (1H, dd, J=5, 2 Hz), 5.45 (1H, q, J=2 Hz), 5.86 (1H, s; disappeared by the addition of heavy water), 5.86 (1H, m), 6.25 (2H, d, J=16 Hz), 6.92 (1H, d, J=8 Hz), 7.02 (1H, d, J=2 Hz), 7.08 (1H, dd, J=8, 2 Hz), 7.60 (2H, d, J=16 Hz).

EXAMPLE 107

5-Hydroxy-4-(4-methoxybenzyloxy)-2,6,6-trimethyl-2-cyclohepten-1-one (AUM09) (3.04 g, 10 mM) obtained in Example 1 was methylated according to the procedures described in Example 69 and purified by silica gel column chromatography using hexane-ethyl acetate (20:1) as an eluent to obtain 1.85 g (58%) of 1-methoxy-4-(4-methoxybenzyloxy)-2,6,6-trimethyl-8-oxabicyclo[3.2.1] oct-2-ene as a colorless oily intermediate product.

1H-NMR (CDCl$_3$, ppm): 1.23 (3H, s), 1.28 (3H, s), 1.66 (3H, dd, J=2, 1 Hz), 1.81 (2H, s), 3.35 (3H, s), 3.81 (3H, s), 4.00 (1H, dd, J=5, 2 Hz), 4.40–4.60 (3H, m), 5.50 (1H, m), 6.88 (2H, d, J=7 Hz), 7.26 (2H, d, J=7 Hz).

The above intermediate product (3.18 g, 10 mM) was treated with 2.6M equivalent of DDQ according to the procedures described in Example 7 and purified by silica gel column chromatography using benzene-ethyl acetate (30:1) as an eluent to obtain 1.63 g (83%) of 1-methoxy-2,6,6-trimethyl-8-oxabicyclo[3.2.1]oct-2-en-4-one (AU253) as a colorless oily product.

IR (KBr, cm$^{-1}$): 1686, 1625, 1438, 1265, 1055.

1H-NMR (CDCl$_3$, ppm): 0.99 (3H, s), 1.36 (3H, s), 1.65 (1H, d, J=13 Hz), 1.94 (1H, d, J=13 Hz), 2.00 (3H, s), 3.43 (3H, s), 4.03 (1H, s), 5.84 (1H, brs).

To a solution of the above product (AU253) in methanol (10 ml) was added sodium borohydride (0.20 g, 5.3 mM) at 0° C. and it was stirred for an hour. The mixture was then diluted with water, extracted with ethyl acetate, washed with brine, dried over magnesium sulfate, filtered, and concentrated. The residue was purified by silica gel column chromatography using hexane-ethyl acetate (5:1) as an eluent and crystallized from hexane to obtain 1.30 g (79%) of 1-methoxy-2,6,6-trimethyl-8-oxabicyclo[3.2.1]oct-2-en-4-ol (AU152) as obtained in Example 96.

EXAMPLE 108

1-Methoxy-2,6,6-trimethyl-8-oxabicyclo[3.2.1]oct-2-en-4-ol (AU152) (297 mg, 1.5 mM) which was obtained in Example 107 was acetylated by a conventional method and purified by silica gel column chromatography using hexane-ethyl acetate (20:1) as an eluent to obtain 312 mg (86%) of 4-acetoxy-1-methoxy-2,6,6-trimethyl-8-oxabicyclo[3.2.1]oct-2-ene (AU158) as a colorless oily product.

IR (KBr, cm$^{-1}$): 1742, 1237, 1042.

1H-NMR (CDCl$_3$, ppm): 1.22 (3H, s), 1.24 (3H, s), 1.69 (3H, t, J=2 Hz), 1.83 (2H, s), 2.06 (3H, s), 3.37 (3H, s), 4.09 (1H, dd, J=5, 2 Hz), 5.38 (1H, m), 5.72 (1H, m).

EXAMPLE 109

To a solution of 5-hydroxy-4-(4-methoxybenzyloxy)-2,6,6-trimethyl-2-cyclohepten-1-one (AUM09) (3.04 g, 10 mM), which was obtained in Example 1, in tetrahydrofuran (30 ml), 55% sodium hydride (0.52 g, 12 mM) was added under ice-cooling with stirring. After ten minutes, the mixture was heated to 60° C. for ten minutes, ice-cooled, treated with benzoyl chloride (1.39 ml, 12 mM), then cooled down to room temperature and stirred for an hour. The reaction mixture was concentrated, diluted with ethyl acetate, washed with water and with brine, dried over magnesium sulfate, filtered, and concentrated. The residue was crystallized from a mixed solvent of ethyl acetate and hexane to obtain 2.75 g (67%) of the intermediate 1-benzoyloxy-4-(4-methoxybenzyloxy)-2,6,6-trimethyl-8-oxabicyclo[3.2.1]oct-2-ene as colorless prisms.

Melting point: 106.5° to 107° C.

IR (KBr, cm$^{-1}$): 1736, 1613, 1514, 1267, 1148, 710.

1H-NMR (CDCl$_3$, ppm): 1.31 (3H, s), 1.37 (3H, s), 1.68 (3H, t, J=2 Hz), 2.19 (2H, s), 3.82 (3H, s), 4.15 (1H, dd, J=5, 2 Hz), 4.52 (1H, d, J=12 Hz), 4.57 (1H, d, J=12 Hz), 4.75 (1H, m), 5.51 (1H, m), 6.89 (2H, d, J=9 Hz), 7.28 (2H, d, J=9 Hz), 7.45 (2H, m), 7.59 (1H, m), 8.06 (2H, m).

The above intermediate product (0.4 g, 1 mM) was treated with DDQ according to the procedures described in Example 7 and fractionated by silica gel column chromatography using benzene-ethyl acetate (50:1 to 5:1) to obtain 130 mg (45%) of 1-benzoyloxy-2,6,6-trimethyl-8-oxabicyclo[3.2.1]oct-2-en-4-one (AU168) as a colorless oily product.

IR (KBr, cm$^{-1}$): 1737, 1684, 1674, 1454, 1276, 1144, 710.

1H-NMR (CDCl$_3$, ppm): 1.06 (3H, s), 1.44 (3H, s), 2.01 (3H, d, J=2 Hz), 2.09 (1H, d, J=12 Hz), 2.33 (1H, d, J=12 Hz), 4.21 (1H, d, J=2 Hz), 5.91 (1H, m), 7.48 (2H, m), 7.62 (1H, m), 8.03 (2H, m).

109 mg (38%) of 1-benzoyloxy-2,6,6-trimethyl-8-oxabicyclo[3.2.1]oct-2-en-4-ol (AU169) as a colorless oily product were obtained from an eluted portion of 10:1 to 5:1.

IR (KBr, cm$^{-1}$): 3445, 1732, 1689, 1452, 1262, 1144, 711.

1H-NMR (CDCl$_3$, ppm): 1.34 (3H, s), 1.37 (3H, s), 1.68 (3H, t, J=2 Hz), 2.20 (2H, s), 4.90 (1H, dd, J=5, 2 Hz), 5.03 (1H, m), 5.44 (1H, m), 7.44 (2H, m), 7.57 (1H, m), 8.05 (2H, m).

EXAMPLE 110

A solution of 5-benzoyloxy-4-methoxy-2,6,6-trimethyl-2-cyclohepten-1-one (AU121) (1.51 g, 5.0 mM) obtained in Example 16 in methanol (20 ml) was catalytically hydrogenated by the addition of 10% palladium/carbon (0.02 g), and then the catalyst was filtered off. The filtrate was concentrated and the residue was fractionated by silica gel column chromatography using benzene-ethyl acetate (25:1) to obtain 0.26 g (17%) of 2,4-trans-5-benzoyloxy-4-methoxy-2,6,6-trimethylcycloheptan-1-one (AU123A) as colorless plates from the first eluted portion. Melting point: 101° to 102° C.

IR (KBr, cm$^{-1}$): 1718, 1698, 1272, 1112, 713.

1H-NMR (CDCl$_3$, ppm): 1.02 (3H, s), 1.15 (3H, s), 1.18 (3H, d, J=7 Hz), 2.06 (2H, m), 2.33 (1H, d, J=13 Hz), 2.65 (1H, m), 2.95 (1H, d, J=13 Hz), 3.38 (3H, s), 3.56 (3H, m), 5.22 (1H, d, J=5 Hz), 7.48 (2H, m), 7.58 (1H, m), 8.07 (2H, m).

The successive eluted portion was crystallized from hexane to obtain 0.47 g (31%) of 2,4-cis-5-benzoyloxy-4-methoxy-2,6,6-trimethylcycloheptan-1-one (AU123B) as colorless needles. Melting point: 133° to 134.5° C.

IR (KBr, cm$^{-1}$): 1725, 1694, 1270, 1094, 714.

1H-NMR (CDCl$_3$, ppm): 1.06 (3H, s), 1.08 (3H, s), 1.19 (3H, d, J=7 Hz), 1.84 (1H, m), 2.09 (1H, m), 2.24 (1H, d, J=13 Hz), 2.38 (1H, m), 2.87 (1H, d, J=13 Hz), 3.29 (3H, s), 3.29 (1H, m), 5.13 (1H, d, J=9 Hz), 7.47 (2H, m), 7.58 (1H, m), 8.08 (2H, m).

EXAMPLE 111

5-(3-Chlorobenzoyloxy)-4-(4-methoxybenzyloxy)-2,6,6-trimethyl-2-cyclohepten-1-one (AU125) (3.00 g, 6.78 mM) obtained in Example 11 was catalytically hydrogenated according to the procedures described in Example 110, purified by silica gel column chromatography using hexane-ethyl acetate (10:1) as an eluent and crystallized from a mixed solvent of ethyl acetate and hexane to obtain 0.81 g (27%) of 2,4-cis-5-(3-chlorobenzoyloxy)-4-(4-methoxybenzyloxy)-2,6,6-trimethyl cycloheptan-1-one (AU131) as colorless needles. Melting point: 104° to 105° C.

IR (KBr, cm$^{-1}$): 1713, 1615, 1514, 1257, 1069, 820, 745.

1H-NMR (CDCl$_3$, ppm): 1.01 (3H, s), 1.06 (3H, s), 1.18 (3H, d, J=7 Hz), 1.89 (1H, m), 2.10 (1H, m), 2.22 (1H, d, J=13 Hz), 2.32 (1H, m), 2.87 (1H, d, J=13 Hz), 3.50 (1H, brd, J=9 Hz), 3.75 (3H, s), 4.30 (1H, d, J=11 Hz), 4.50 (1H, d, J=11 Hz), 5.17 (1H, d, J=9 Hz), 6.66 (2H, d, J=9 Hz), 6.97 (2H, d, J=9 Hz), 7.40 (1H, t, J=8 Hz), 7.55 (1H, dm, J=8 Hz), 7.89 (1H, dt, J=8, 2 Hz), 7.94 (1H, t, J=2 Hz).

EXAMPLE 112

The product (AU)131 of Example 111 (795 mg, 1.76 mM) was treated with DDQ according to the procedures described in Example 7 and crystallized from a mixed solvent of ethyl acetate and hexane to obtain 405 mg (70%) of 2,4-cis-5-(3-chlorobenzoyloxy)-4-hydroxy-2,6,6-trimethylcycloheptan-1-one (AU132) as colorless plates.

Melting point: 136° to 137° C.

IR (KBr, cm$^{-1}$): 3457, 1722, 1675, 1261, 982, 746.

1H-NMR (CDCl$_3$, ppm): 1.05 (3H, s), 1.07 (3H, s), 1.18 (3H, d, J=7 Hz), 1.94 (1H, d, J=6 Hz; disappeared by the addition of heavy water), 1.94 (1H, m), 2.10 (1H, m), 2.21 (1H, d, J=13 Hz), 2.44 (1H, m), 2.89 (1H, d, J=13 Hz), 3.82 (1H, m; brt by the addition of heavy water, J=12, 9 Hz), 5.03

(1H, d, J=9 Hz), 7.42 (1H, t, J=8 Hz), 7.57 (1H, dm, J=8 Hz), 7.96 (1H, dt, J=8, 2 Hz), 8.04 (1H, t, J=2 Hz).

EXAMPLE 113

A solution of Saishin N (11.05 g, 60 mM) in methanol (50 ml) was catalytically hydrogenated by the addition of 10% palladium/carbon (0.29) at room temperature and filtered. The filtrate was treated with a solution (2 ml) of 28% sodium methoxide in methanol and stirred for a day at room temperature. The reaction mixture was concentrated, diluted with ethyl acetate, washed with brine, dried over sodium sulfate, filtered, and concentrated. The residue was purified by silica gel column chromatography using hexane-ethyl acetate (10:1) as an eluent to obtain 8.40 g (76%) of 2,4-cis-2,6,6-trimethyl-8-oxabicyclo[3.2.1]octan-1,4-diol (AUM11) as a colorless oily product.

IR (KBr, $cm^{-1}$): 3404, 1694, 1458, 1052, 1034.

It will be noted that the catalytic hydrogenation formed nearly the same amount of the cis- and trans-compounds (i.e. 2,6,6-trimethyl-cycloheptan-1-on-4,5-diol). When the mixture thereof was treated with sodium methoxide in methanol, the thermodynamically favorable cis form became the major product (nearly 95%).

EXAMPLE 114

5-Hydroxy-4-methoxy-2,6,6-trimethyl-2-cyclohepten-1-one (AU154) (24 g, 0.12 mM) obtained in Example 4 was catalytically hydrogenated and treated with base according to the procedures described in Example 113 and crystallized from hexane to obtain 15.2 (63%) of 2,4-cis-4-methoxy-2,6,6-trimethyl-8-oxabicyclo[3.2.1]octan-1-ol (AUM13) as a colorless crystalline product.

IR (KBr, $cm^{-1}$): 3356, 1270, 1114, 1064, 1008, 985, 974.

As in Example 113, the catalytic hydrogenation formed nearly the same amount of the cis- and trans-compounds (i.e. 5-hydroxy-4-methoxy-2,6,6-trimethyl-cycloheptan-1-one). When the mixture thereof was treated with sodium methoxide in methanol, the thermodynamically favorable cis form became the major product (nearly 95%).

EXAMPLE 115

5-Hydroxy-4-(4-methoxybenzyloxy)-2-6,6-trimethyl-2-cyclohepten-1-one (AUM09) (16.6 g, 54.5 mM) obtained in Example 1 was catalytically hydrogenated and treated with base according to the procedures described in Example 113 to obtain 12.2 g (73%) of 2,4-cis-4-(4-methoxybenzyloxy)-2,6,6-trimethyl-8-oxabicyclo[3.2.1]octan-1-ol (AUMI5) as a colorless oily product.

IR (KBr, $cm^{-1}$): 3384, 1514, 1247, 1062, 1036, 752.

As in Example 113, the catalytic hydrogenation formed nearly the same amount of the cis- and trans-compounds (i.e. 5-hydroxy-4-(4-methoxybenzyloxy)-2,6,6-trimethyl-cycloheptan-1-one). When the mixture thereof was treated with sodium methoxide in methanol, the thermodynamically favorable cis form became the major product (nearly 95%).

EXAMPLE 116

A solution of Saishin N (25.8 g, 0.1M) in methanol was catalytically hydrogenated (to produce a cis- and trans-mixture of 2,6,6-trimethyl-cycloheptan-1-on-4,5-diol as in Example 113) and then treated with base according to the procedures described in Example 113 to produce a mixture of 2,4-cis-2,6,6-trimethyl-8-oxabicyclo[3.2.1]octan-1,4-diol and 2,4-trans-2,6,6-trimethyl-8-oxabicyclo[3.2.1]octan-1,4-diol, and this mixture was then treated with p-toluene sulfonic acid in methanol and left to stand for two days to produce a mixture of the below cis and trans compounds (AU105B and AU105A). Potassium carbonate was added to the reaction mixture, which was stirred, concentrated at a reduced pressure, diluted with ethyl acetate, washed with brine, dried over magnesium sulfate, filtered, and concentrated. The residue was crystallized from hexane to obtain 18.1 g (64%) of 2,4-cis-1-methoxy-2,6,6-trimethyl-8-oxabicyclo[3.2.1]octan-4-ol (AU105B) as colorless cottony crystals. Melting point: 74° to 75° C.

IR (KBr, $cm^{-1}$): 3242, 1464, 1349, 1056, 1011.

1H-NMR (CDCl$_3$, ppm): 0.85 (3H, d, J=6 Hz), 1.25 (3H, s), 1.26 (3H, s), 1.43 (1H, t, J=14 Hz), 1.57 (1H, d, J=14 Hz) 1.68 (1H, d, J=14 Hz), 2.02 (2H, m), 3.36 (3H, s), 3.60 (1H, brd, J=4 Hz), 4.00 (1H, m).

The mother liquor of the crystal product was purified by silica gel column chromatography using hexane-ethyl acetate (10:1) as an eluent and crystallized from hexane to obtain 4.65 g (16%) of 2,4-trans-1-methoxy-2,6,6-trimethyl-8-oxabicyclo[3.2.1]octan-4-ol (AU105A) as colorless cottony crystals. Melting point: 93° to 93.5° C.

IR (KBr, $cm^{-1}$): 3217, 1464, 1354, 1280, 1048.

1H-NMR (CDCl$_3$, ppm): 1.09 (3H, d, J=7 Hz), 1.24 (3H, s), 1.29 (3H, s), 1.41 (1H, d, J=5 Hz; disappeared by the addition of heavy water), 1.62 (1H, d, J=14 Hz), 1.77 (1H, m), 1.88–2.06 (3H, m) 3.35 (3H, s), 3.60 (1H, brd, J=4 Hz), 4.15 (1H, m).

EXAMPLE 117

2,4-Cis-1-methoxy-2,6,6-trimethyl-8-oxabicyclo[3.2.1] octan-4-ol (AU105B) (0.3 g, 1.5 mM) obtained in Example 116 was acetylated by a conventional method to obtain 349 mg (96.1%) of 2,4cis-4-acetoxy-1-methoxy-2,6,6-trimethyl-8-oxabicyclo[3.2.1]octane (AU108B) as a crystalline product. Melting point: 52° to 53° C.

IR (KBr, $cm^{-1}$): 1734, 1472, 1248.

1H-NMR (CDCl$_3$, ppm): 0.84 (1H, d, J=6 Hz), 1.20 (3H, s), 1.23 (3H, s), 1.42 (1H, q, J=12 Hz), 1.58 (1H, d, J=13 Hz), 1.70 (1H, d, J=13 Hz), 2.03 (3H, s), 2.08 (2H, m), 3.37 (3H, s), 3.71 (1H, d, J=4 Hz), 4.95 (1H, m).

EXAMPLE 118

2,4-Trans-1-methoxy-2,6,6-trimethyl-8-oxabicyclo [3.2.1]octan-4-ol (AU105A) (0.3 g, 1.5 mM) obtained in Example 116 was acetylated by a conventional method to obtain 317 mg (87.3%) of 2,4-trans-1-methoxy-4-acetoxy-2,6,6-trimethyl-8-oxabicyclo[3.2.1]octane (AU108A) as a colorless oily product.

IR (KBr, $cm^{-1}$): 1738, 1241, 1041.

1H-NMR (CDCl$_3$, ppm): 1.13 (3H, d, J=7 Hz), 1.22 (3H, s), 1.23 (3H, s), 1.63 (1H, d, J=13 Hz), 1.79 (1H, m), 2.03 (3H, s), 1.90–2.10 (3H, m), 3.35 (3H, s), 3.70 (1H, d, J=4 Hz), 5.11 (1H, m).

EXAMPLE 119

2,4-Cis-1-methoxy-2,6,6-trimethyl-8-oxabicyclo[3.2.1] octan-4-ol (AU105B) (0.30 g, 1.5 mM) obtained in Example 116 was methylated according to the procedures described in Example 69 to obtain 0.235 g (73.2%) of 2,4-cis1,4-dimethoxy-2,6,6-trimethyl-8-oxabicyclo[3.2.1]octane (AU109B) as a colorless oily product.

1H-NMR (CDCl$_3$, ppm): 0.84 (3H, d, J=6 Hz), 1.20 (3H, s), 1.23 (3H, s), 1.31 (1H, d, J=12 Hz), 1.55 (1H, d, J=13

Hz), 1.66 (1H, d, J=13 Hz), 1.94–2.11 (2H, m), 3.34 (3H, s), 3.37 (3H, s), 3.47–3.55 (1H, m), 3.75 (1H, d, J=4 Hz).

EXAMPLE 120

2,4-Trans-1-methoxy-2,6,6-trimethyl-8-oxabicyclo[3.2.1]octan-4-ol (AU105A) (0.30 g, 1.5 mM) obtained in Example 116 was treated as described in Example 119 to obtain 0.256 g (80.7%) of 2,4-trans-1,4-dimethoxy-2,6,6-trimethyl-8-oxabicyclo[3.2.1]octane (AU109A) as a colorless oily product.

IR (KBr, cm$^{-1}$): 1468, 1219, 1109.

1H-NMR (CDCl$_3$, ppm): 1.09 (3H, d, J=7 Hz), 1.22 (3H, s), 1.23 (3H, s), 1.60 (1H, d, J=14 Hz), 1.50–2.00 (4H, m), 3.34 (3H, s), 3.35 (3H, s), 3.64 (1H, m), 3.74 (1H, m).

EXAMPLE 121

To a solution of 2,4-cis-1-methoxy-2,6,6-trimethyl-8-oxabicyclo[3.2.1]octan-4-ol (AU105B) (1.0 g, 5.0 mM) obtained in Example 116 in tetrahydrofuran (50 ml), a solution (1.59M/1; 4.7 ml) of n-butyl lithium in hexane was added under an argon atmosphere at –60° C. After stirring at –60° C. for 30 minutes, benzoyl chloride (0.84 g, 7.2 mM) was added to the mixture, and then it was stirred for 30 minutes, and warmed up to room temperature. The reaction mixture was poured onto ice-water and saturated with salt, extracted with ethyl acetate, dried, purified by silica gel column chromatography using hexane-ethyl acetate (50:1) as an eluent, and crystallized from hexane to obtain 753 mg (49.5%) of 2,4-cis-4-benzoyloxy-1-methoxy-2,6,6-trimethyl-8-oxabicyclo[3.2.1]octane (AU119) as colorless needles. Melting point: 89° to 90° C.

IR (KBr, cm$^{-1}$): 1709, 1599, 1469, 1278, 1110, 1013, 711.

1H-NMR (CDCl$_3$, ppm): 0.88 (3H, d, J=7 Hz), 1.27 (3H, s), 1.35 (3H, s), 1.50–1.70 (2H, m), 1.78 (1H, d, J=14 Hz), 2.20 (2H, m), 3.40 (3H, s), 3.83 (1H, d, J=4 Hz), 5.24 (1H, m), 7.44 (2H, m), 7.57 (1H, m), 8.00 (2H, m).

EXAMPLE 122

To a solution of 2,4-cis-1-methoxy-2,6,6-trimethyl-8-oxabicyclo[3.2.1]octan-4-ol (AU105B) (4.52 g, 22 mM) obtained in Example 116 in tetrahydrofuran, 55% sodium hydride (1.05 g, 24 mM) and benzyl bromide (2.85 ml, 24 mM) were added under ice-cooling, and the mixture was stirred for two hours at room temperature and heated under reflux for 30 minutes. The reaction mixture was treated with ice-water, extracted with ethyl acetate, washed with brine, then dried over magnesium sulfate, filtered, and concentrated. The residue was fractionated by silica gel column chromatography using hexane-ethyl acetate (100:1 to 30:1) as an eluent. From the first eluted portion, 1.00 g (15.7%) of 2,4-trans-4-benzyloxy-1-methoxy-2,6,6-trimethyl-8-oxabicyclo[3.2.1]octane (AU162A) was obtained as a colorless oily product.

IR (KBr, cm$^{-1}$): 1466, 1217, 1110.

1H-NMR (CDCl$_3$, ppm): 1.07 (3H, d, J=7 Hz), 1.22 (3H, s), 1.30 (3H, s), 1.63 (1H, d, J=14 Hz), 1.91 (1H, d, J=14 Hz), 1.82–2.10 (3H, m 3.34 (3H, s), 3.73 (1H, brd, J=4 Hz), 3.84 (1H, m), 4.53 (2H, s), 7.31 (5H, m).

2.36 g (37.0%) of 2,4-cis-4-benzyloxy-1-methoxy-2,6,6-trimethyl-8-oxabicyclo[3.2.1]octane (AU162B) were obtained as a colorless oily product from the successive eluted portion.

IR (KBr, cm$^{-1}$): 1466, 1220, 1114, 1071.

1H-NMR (CDCl$_3$, ppm): 0.84 (3H, d, J=7 Hz), 1.24 (3H, s), 1.28 (3H, s), 1.42 (1H, m), 1.57 (1H, d, J=14 Hz), 1.68 (1H,d, J=14 Hz), 1.98–2.09 (2H, m), 3.36 (3H, s), 3.70 (1H, m), 3.75 (1H, m), 4.53 (2H, s), 7.30 (5H, m).

EXAMPLE 123

2,4-Cis-2,6,6-trimethyl-8-oxabicyclo[3.2.1]octan-1,4-diol (AUM11) (0.93 g, 5 mM) obtained in Example 113 was benzoylated as described in Example 6 and crystallized from hexane to obtain 1.04 g (71%) of 2,4-cis-4-benzoyloxy-2,6,6-trimethyl-8-oxabicyclo[3.2.1]octan-1-ol (AU502) as colorless needles. Melting point: 157° to 158° C.

IR (KBr, cm$^{-1}$): 3467, 1695, 1317, 1307, 1291, 1128, 720.

EXAMPLE 124

The product (AU502) of Example 123 (0.5 g, 1.72 mM) was acetylated by a conventional method and crystallized from water to obtain 0.43 g (75%) of 2,4-cis-5-acetoxy-4-benzoyloxy-2,6,6-trimethylcycloheptan-1-one (AU194) as colorless crystals. Melting point: 166° to 200° C.

IR (KBr, cm$^{-1}$): 1737, 1710, 1451, 1374, 1273, 1241, 1112, 715.

1H-NMR (CDCl$_3$, ppm): 1.01 (3H, s), 1.05 (3H, s), 1.16 (3H, d, J=7 Hz), 1.90 (3H, s), 2.06 (2H, m), 2.26 (1H, d, J=13 Hz), 2.54 (1H, m), 2.88 (1H, d, J=13 Hz), 5.17 (2H, m), 7.45 (2H, m), 7.58 (1H, m), 7.98 (2H, m).

EXAMPLE 125

2,4-Cis-2,6,6-trimethyl-8-oxabicyclo[3.2.1]octane-1,4-diol (AUM11) (0.93 g, 5 mM) obtained in Example 113 was treated with 3-chlorobenzoyl chloride (0.96 g, 5.5 mM) according to the procedures described in Example 17 to form 2,4-cis-4-(3-chlorobenzoyloxy)-2,6,6-trimethyl-8-oxabicyclo[3.2.1]octan-1-ol as an intermediate, and this was then acetylated by a conventional method and crystallized from a mixed solvent of ethyl acetate and hexane to obtain 0.59 g (32%) of 2,4-cis-5-acetoxy-4-(3-chlorobenzoyloxy)-2,6,6-trimethylcycloheptan-1-one (AU199) as colorless needles. Melting point: 191° to 192° C.

IR (KBr, cm$^{-1}$): 1743, 1718, 1703, 1263, 1237, 1124, 754, 740.

1H-NMR (CDCl$_3$, ppm): 1.01 (3H, s), 1.05 (3H, s), 1.17 (3H, d, J=7 Hz), 1.92 (3H, s), 2.04 (2H, m), 2.27 (1H, d, J=13 Hz), 2.54 (1H, m), 2.88 (1H, d, J=13 Hz), 5.15 (2H, m), 7.40 (1H, t, J=8 Hz), 7.55 (1H, brd, J=8 Hz), 7.86 (1H, brd, J=8 Hz), 7.98 (1H, m).

EXAMPLE 126

2,4-Cis-2,6,6-trimethyl-8-oxabicyclo[3.2.1]octan-1,4-diol (AUM11) (5.59 g, 30 mM) obtained in Example 113 was acetylated by a conventional method and crystallized from ethyl acetate and hexane to obtain 6.739 (83%) of 2,4-cis-4,5-diacetoxy-2,6,6-trimethyl-cycloheptan-1-one (AU117) as colorless needles. Melting point: 77° to 78° C.

IR (KBr, cm$^{-1}$): 1744, 1700, 1246, 1229.

1H-NMR (CDCl$_3$, ppm): 0.96 (3H, s), 1.00 (3H, s), 1.13 (3H, d, J=7 Hz), 1.91 (2H, m), 2.02 (3H, s), 2.07 (3H, s), 2.22 (1H, d, J=13 Hz), 2.47 (1H, m), 2.81 (1H, d, J=13 Hz), 4.95 (2H, m).

EXAMPLE 127

2,4-Cis-4-methoxy-2,6,6-trimethyl-8-oxabicyclo[3.2.1]octan-1-ol (AUM13) (1.0 g, 5 mM) obtained in Example 114 was acetylated by a conventional method and crystallized from hexane to obtain 0.9 g (75%) of 2,4-cis-5-acetoxy-4- methoxy-2,6,6-trimethylcycloheptan-1-one (AU120) as colorless crystals. Melting point: 80° to 82° C.

IR (KBr, cm$^{-1}$): 1742, 1699, 1239, 1092, 1026.

1H-NMR (CDCl$_3$, ppm): 0.92 (3H, s), 1.00 (3H, s), 1.16 (3H, d, J=7 Hz), 1.74 (1H, m), 2.03 (1H, m), 2.11 (3H, s), 2.18 (1H, d, J=13 Hz), 2.33 (1H, m), 2.78 (1H, d, J=13 Hz), 3.13 (1H, m), 3.34 (3H, s), 4.85 (1H, d, J=9 Hz).

EXAMPLE 128

2,4-Cis-4-methoxy-2,6,6-trimethyl-8-oxabicyclo[3.2.1]octan-1-ol (AUM13) (1 g, 5 mM) obtained in Example 114 was benzoylated according to the procedures described in Example 6 and purified by silica gel column chromatography using benzene-ethyl acetate (50:1) as an eluent to obtain 272 mg (17.9%) of 2,4-cis-1-benzoyloxy-4-methoxy-2,6,6-trimethyl-8-oxabicyclo[3.2.1]octane (AU122) as a colorless oily product.

1H-NMR (CDCl$_3$, ppm): 0.94 (3H, d, J=7 Hz), 1.25 (3H, s), 1.38 (3H, s), 1.41 (1H, q, J=12 Hz), 2.10 (3H, m), 2.72 (1H, m), 3.37 (3H, s), 3.65 (1H, m), 3.95 (1H, d, J=4 Hz), 7.43 (2H, m), 7.55 (1H, m), 8.03 (2H, m).

EXAMPLE 129

2,4-Cis-4-(4-methoxybenzyloxy)-2,6,6-trimethyl-8-oxabicyclo[3.2.1]octan-1-ol (AUM15) (1.83 g, 6 mM) obtained in Example 115 was acetylated by a conventional method and fractionated by silica gel column chromatography using hexane-ethyl acetate (10:1 to 5:1) as an eluent. From the first eluted portion 0.28 g (13%) of 2,4-cis-1-acetoxy-4-(4-methoxybenzyloxy)-2,6,6-trimethyl-8-oxabicyclo[3.2.1]octane (AU186) was obtained as a colorless oily product.

IR (KBr, cm$^{-1}$): 1753, 1612, 1514, 1249.

1H-NMR (CDCl$_3$, ppm): 0.83 (3H, d, J=6 Hz), 1.25 (3H, s), 1.29 (3H, s), 1.41 (1H, q, J=12 Hz), 1.91 (1H, d, J=13 Hz), 1.94 (1H, d, J=13 Hz), 2.02 (1H, m), 2.05 (3H, s), 2.55 (1H, m), 3.75 (1H, m), 3.80 (3H, s), 3.84 (1H, m), 4.46 (2H, s), 6.86 (2H, d, J=9 Hz), 7.22 (2H, d, J=9 Hz).

1.41 g (67%) of 2,4-cis-5-acetoxy-4-(4-methoxybenzyloxy)-2,6,6-trimethylcycloheptan-1-one (AU185) were obtained from the successive eluted portion.

IR (KBr, cm$^{-1}$): 1740, 1700, 1613, 1514, 1244, 1031.

1H-NMR (CDCl$_3$, ppm): 0.91 (3H, s), 1.01 (3H, s), 1.13 (3H, d, J=7 Hz), 1.82 (1H, m), 2.04 (3H, s), 2.05 (1H, m), 2.17 (1H, d, J=13 Hz), 2.28 (1H, m), 2.77 (1H, d, J=13 Hz), 3.38 (1H, m), 3.80 (3H, s), 4.42 (1H, d, J=13 Hz), 4.53 (1H, d, J=13 Hz), 4.93 (1H, d, J=9 Hz), 6.86 (2H, d, J=9 Hz), 7.19 (2H, d, J=9 Hz).

EXAMPLE 130

2,4-Cis-4-(4-methoxybenzyloxy)-2,6,6-trimethyl-8-oxabicyclo[3.2.1]octan-1-ol (AUM15) (2.13 g, 6.9 mM) obtained in Example 115 was benzoylated according to the procedures described in Example 6 and fractionated by silica gel column chromatography using benzene and benzene-ethyl acetate (20:1) as an eluent. The first eluted part was crystallized from a mixed solvent of ethyl acetate and hexane to obtain 0.40 g (14%) of 2,4-cis-1-benzoyloxy-4-(4-methoxy-benzyloxy)-2,6,6-trimethyl-8-oxabicyclo[3.2.1]octane (AU188) as colorless plates. Melting point: 89.5° to 90.5° C.

IR (KBr, cm$^{-1}$): 1742, 1614, 1512, 1248.

1H-NMR (CDCl$_3$, ppm): 0.92 (3H, d, J=7 Hz), 1.30 (3H, s), 1.37 (3H, s), 1.48 (1H, q, J=12 Hz), 2.09 (3H, m), 2.71 (1H, m), 3.80 (3H, s), 3.84 (1H, m), 3.91 (1H, m), 4.47 (1H, d, J=12 Hz), 4.51 (1H, d, J=12 Hz), 6.87 (2H, d, J=9 Hz), 7.24 (2H, d, J=9 Hz), 7.42 (1H, m), 8.01 (2H, m).

The successive eluted portion was crystallized from a mixed solvent of ethyl acetate and benzene to obtain 0.65 g (23%) of 2,4-cis-5-benzoyloxy-4-(4-methoxybenzyloxy)-2,6,6-trimethylcycloheptan-1-one (AU187) as colorless needles. Melting point: 70.5° to 71.5° C.

IR (KBr, cm$^{-1}$): 1717, 1701, 1612, 1515, 1272, 713.

1H-NMR (CDCl$_3$, ppm): 1.02 (3H, s), 1.07 (3H, s), 1.16 (3H, d, J=7 Hz), 1.89 (1H, m), 2.08 (1H, m), 2.23 (1H, d, J=13 Hz), 2.34 (1H, m), 2.86 (1H, d, J=13 Hz), 3.51 (1H, m), 3.73 (3H, s), 4.34 (1H, d, J=13 Hz), 4.48 (1H, d, J=13 Hz), 5.18 (1H, d, J=9 Hz), 6.64 (2H, d, J=9 Hz), 6.98 (2H, d, J=9 Hz), 7.46 (2H, m), 7.58 (1H, m), 8.02 (2H, m).

EXAMPLE 131

2,4-Cis-5-benzoyloxy-4-(4-methoxybenzyloxy)-2,6,6-trimethylcycloheptan-1-one (AU187) (574 mg, 1.4 mM) obtained in Example 130 was treated with DDQ according to the procedures described in Example 7 and crystallized from a mixed solvent of ethyl acetate and hexane to obtain 330 mg (81%) of 2,4-cis-5-benzoyloxy-4-hydroxy-2,6,6-trimethylcycloheptan-1-one (AU191) as colorless plates.

Melting point: 166° to 167.5° C.

IR (KBr, cm$^{-1}$): 3436, 1717, 1682, 1270, 706.

1H-NMR (CDCl$_3$, +D$_2$O, ppm): 1.06 (3H, s), 1.07 (3H, s), 1.18 (3H, d, J=7 Hz), 1.96 (1H, m), 2.10 (1H, m), 2.20 (1H, d, J=13 Hz), 2.44 (1H, m), 2.89 (1H, d, J=13 Hz), 3.82 (1H, m), 5.03 (1H, d, J=9 Hz), 7.48 (2H, m), 7.60 (1H, m), 8.09 (2H, m).

EXAMPLE 132

The product (AU191) (206 mg, 0.7 mM) of Example 131 was acetylated by a conventional method and crystallized from water to obtain 190 mg (81%) of 2,4-cis-4-acetoxy-5-benzoyloxy-2,6,6-trimethylcycloheptan-1-one (AU192) as colorless crystals. Melting point: 119.5° to 121° C.

IR (KBr, cm$^{-1}$): 1732, 1694, 1270, 1106, 712.

1H-NMR (CDCl$_3$+D$_2$O, ppm): 1.07 (3H, s), 1.08 (3H, s), 1.17 (3H, d, J=7 Hz), 1.98 (2H, m), 2.27 (1H, d, J=13 Hz), 2.51 (1H, m), 2.90 (1H, d, J=13 Hz), 5.13 (1H, m), 5.23 (1H, d, J=9 Hz), 7.45 (2H, m), 7.58 (1H, m), 7.99 (2H, m).

EXAMPLE 133

2,4-Cis-4-(4-methoxybenzyloxy)-2,6,6-trimethyl-8-oxabicyclo[3.2.1]octan-1-ol (AUM15) (1.2 g, 3.9 mM) obtained in Example 115 was treated with benzoyl chloride according to the procedures described in Example 17 to obtain 0.97 g (60%) of 2,4-cis-1-benzoyloxy-4-(4-methoxybenzyloxy)-2,6,6-trimethyl-8-oxabicyclo[3.2.1]octane (AU188) as obtained in Example 130.

The product (AU188) so obtained (821 mg, 2.0 mM) was treated with DDQ according to the procedures described in Example 7 and crystallized from a mixed solvent of ethyl acetate and hexane to obtain 410 mg (71%) of 2,4-cis-1-benzoyloxy-2,6,6-trimethyl-8-oxabicyclo[3.2.1]octan-4-ol (AU252) as colorless needles.

Melting point: 87° to 88° C.

IR (KBr, cm$^{-1}$): 3516, 1726, 1276, 997.

1H-NMR (CDCl$_3$, ppm): 0.95 (3H, d, J=7 Hz), 1.31 (3H, s), 1.40 (3H, s), 1.51 (1H, q, J=12 Hz), 1.58 (1H, brs; disappeared by the addition of heavy water), 2.07 (1H, d, J=13 Hz), 2.08 (1H, m), 2.16 (1H, d, J=13 Hz), 2.74 (1H, m), 3.80 (1H, d, J=4 Hz), 4.13 (1H, m), 7.43 (2H, m), 7.56 (1H, m), 8.02 (2H, m).

EXAMPLE 134

To a solution of 2,4-cis-4-(4-methoxybenzyloxy)-2,6,6-trimethyl-8-oxabicyclo[3.2.1]octan-1-ol (AUM15) (1.2 g, 3.9 mM) obtained in Example 115 in tetrahydrofuran (10 ml), 55% sodium hydride (0.18 g, 4.1 mM) was added at 0° C. After 10 minutes, 4-nitrobenzoyl chloride (0.76 g, 4.1 mM) was added to the mixture, and it was stirred for an hour and then stirred at room temperature overnight. The reaction mixture was diluted with ethyl acetate, washed with an aqueous diluted potassium carbonate solution and with brine, dried over magnesium sulfate, filtered, and concentrated. The residue was crystallized from a mixed solvent of ethyl acetate and hexane to obtain 1.1 g (62%) of the intermediate 2,4-cis-4-(4-methoxybenzyloxy)-1-(4-nitrobenzoyloxy)-2,6,6-trimethyl-8-oxabicyclo[3.2.1] octane as light yellow prisms. Melting point: 116.5° to 117.5° C.

IR (KBr, cm$^{-1}$): 1740, 1530, 1350, 1276.

1H-NMR (CDCl$_3$, ppm): 0.93 (3H, d, J=7 Hz), 1.32 (3H, s), 1.38 (3H, s), 1.50 (1H, q, J=12 Hz), 2.11 (3H, m), 2.69 (1H, m), 3.81 (3H, s), 3.85 (1H, m), 3.92 (1H, m), 4.48 (1H, d, J=12 Hz), 4.51 (1H, d, J=12 Hz), 6.87 (2H, d, J=8 Hz), 7.24 (2H, d, J=8 Hz), 8.18 (2H, d, J=9 Hz), 8.28 (2H, d, J=9 Hz).

The intermediate product so obtained (1.00 g, 2.2 mM) was treated with DDQ according to the procedures described in Example 7 and crystallized from a mixed solvent of ethyl acetate and hexane to obtain 0.58 g (78%) of 2,4-cis-1-(4-nitrobenzoyloxy)-2,6,6-trimethyl-8-oxabicyclo[3.2.1]octan-4-ol (AU250) as colorless needles. Melting point: 103° to 104° C.

IR (KBr, cm$^{-1}$): 3600–3100, 1740, 1530, 1350, 1276.

1H-NMR (CDCl$_3$, ppm): 0.98 (3H, d, J=7 Hz), 1.33 (3H, s), 1.41 (3H, s), 1.53 (1H, q, J=12 Hz), 2.12 (3H, m), 2.72 (1H, m), 3.82 (1H, d, J=4 Hz), 4.16 (1H, m), 8.18 (2H, d, J=9 Hz), 8.28 (2H, d, J=9 Hz).

EXAMPLE 135

The product (AU250) of Example 134 (436 mg, 1.3 mM) was reduced at the nitro group according to the procedures described in Example 19 to obtain 360 mg (90%) of 2,4-cis-1-(4-aminobenzoyloxy)-2,6,6-trimethyl-8-oxabicyclo [3.2.1]octan-4-ol (AU251) as an orange caramel product.

IR (KBr, cm$^{-1}$): 3462, 3367, 1706, 1628, 1603, 1279, 1170.

1H-NMR (CDCl$_3$, ppm): 0.93 (3H, d, J=7 Hz), 1.30 (3H, s), 1.39 (3H, s), 1.49 (1H, q, J=12 Hz), 1.58 (1H, brs), 2.08 (3H, m), 2.72 (1H, m), 3.78 (1H, d, J=4 Hz), 4.11 (3H, m; 1H by the addition of heavy water, m), 6.63 (2H, d, J=9 Hz), 7.83 (2H, d, J=9 Hz).

EXAMPLE 136

A solution of trifluoroacetic anhydride (4.16 ml, 30 mM) in methylene chloride (10 ml) was added over 20 minutes to a solution of dimethyl sulfoxide (2.84 ml, 40 mM) in methylene chloride (20 ml) while it was maintained at −65° C. After ten minutes, a solution of 2,4-cis-1-methoxy-2,6,6-trimethyl-8-oxabicyclo[3.2.1]octan-4-ol (AU105B) (4.00 g, 20 mM) obtained in Example 116 was added dropwise to the mixture at the same temperature, and after 30 minutes, triethylamine was added at the same temperature. The mixture was then adjusted to room temperature and separated by the addition of water. The aqueous layer was extracted with methylene chloride, and the organic layer was dried over magnesium sulfate, filtered, and concentrated. The residue was purified by silica gel column chromatography using hexane-ethyl acetate (100:1 to 10:1) as an eluent and crystallized from hexane to obtain 3.25 g (82%) of 1-methoxy-2,6,6-trimethyl-8-oxabicyclo[3.2.1]octan-4-one (AU163) as colorless plates. Melting point: 38° to 39° C.

IR (KBr, cm$^{-1}$): 1729, 1458, 1246, 1018.

1H-NMR (CDCl$_3$, ppm): 0.93 (3H, d, J=7 Hz), 1.01 (3H, s), 1.30 (3H, s), 1.75 (1H, d, J=14 Hz), 1.82 (1H, d, J=14 Hz), 1.88 (1H, m), 2.48 (1H, m), 2.60 (1H, m), 3.42 (3H, s), 3.73 (1H, brs). 13C-NMR (CDCl$_3$, ppm): 15.40 (q), 22.29 (q), 29.95 (q), 38.27 (d), 38.35 (t), 39.74 (s), 42.33 (t), 49.59 (q), 90.76 (d), 110.14 (s), 206.27 (s).

It should be noted that as to the mechanism of the acylation of Saishin N, although it was initially thought that 4-substituted products and 5-substituted products were formed simultaneously because of a lack of selectivity as between the two hydroxy groups in Saishin N, it has in fact been found that the corresponding 4-substituted products are first formed in the acylation reaction of Saishin N. Thereafter, the acyl group at the 4-position is transferred to the 5-position by an acyl transfer reaction to form the corresponding 5-substituted products, e.g. in those cases where a strong base like ammonia or triethylamine is present in the reaction mixture or where the reaction mixture is heated or undergoes self-heating due to exothermic reaction.

This acyl transfer reaction reaches equilibrium when the 4-substituted product and 5-substituted product become nearly the same in amount. For this reason, it was considered that 4-substituted products and 5-substituted products were formed simultaneously in many cases, thus providing a mixture thereof.

Also, it has been found that if the reaction conditions are controlled carefully in certain cases, e.g. where the DCC condensation agent method is used, 4-substituted products are obtained predominantly, i.e. because of the absence of a strong base (cf. Examples 57 and 58).

In certain instances, 4-substituted products are formed from 5-substituted starting compounds (cf. Examples 38, 45 and 55) and conversely 5-substituted products are formed from 4-substituted starting compounds (cf. Example 46). In these instances, the reaction mixture is heated whereupon, as noted above, acyl transfer from the 4-position to the 5-position and from the 5-position to the 4-position easily occurs.

However, a mixture of corresponding products is not always obtained, since 4-substituted products are formed predominantly, as noted above, in the acylation reaction according to the DCC condensation agent method (cf. Examples 57 and 58 as aforesaid). Indeed, where 2-chloro-1,3-dimethyl imidazolinium chloride is used as condensation agent, the result is the same as with the DCC condensation agent method. This is because in these cases a weak base like N,N-dimethylbenzylamine or pyridine is used.

Moreover, even where the acylation reaction is performed with the use of an acid anhydride or acid halide, if the reaction conditions are controlled carefully, 4-substituted products are formed predominantly (cf. Example 54). The reaction conditions carefully controlled to achieve production of 4-substituted products predominantly include avoidance of use of a strong base and avoidance of heating of the reaction mixture.

In most other examples, it is seen that 4-substituted and 5-substituted products are both formed. Attempts to separate these isomers do not forthwith result in the obtaining of the pure compounds because the acyl transfer reaction often occurs during the separation or purification process.

Hence, according to the present invention, a 5-acyloxy-4-hydroxy Saishin N derivative may be prepared from a 5-hydroxy-4-acyloxy Saishin N derivative by treating the 5-hydroxy-4-acyloxy Saishin N derivative with a strong base or with heat (e.g. heating it or allowing it to be self-heated by heat generated in situ by an attendant exothermic reaction without applying cooling thereto) sufficiently for effecting acyl transfer of the acyl group from the 4-position to the 5-position to form the corresponding 5-acyloxy-4-hydroxy Saishin N derivative.

Preferably, the treating with a strong base or with heat is effected in a solvent medium such as one in which the 5-hydroxy-4-acyloxy and 5-acyloxy-4-hydroxy Saishin N derivatives are capable of reaching an equilibrium mixture, and particularly concerns the treating of a 5-hydroxy-4-acyloxy-2,6,6-trimethyl-2-cyclohepten-1-one to form the corresponding 5-acyloxy-4-hydroxy-2,6,6-trimethyl-2-cyclohepten-1-one.

Conversely, a 5-hydroxy-4-acyloxy Saishin N derivative may be prepared from a 5-acyloxy-4-hydroxy Saishin N derivative by treating the 5-acyloxy-4-hydroxy Saishin N derivative with heat (e.g. heating it or allowing it to be self-heated by heat generated in situ by an attendant exothermic reaction without applying cooling thereto) sufficiently for effecting acyl transfer of the acyl group from the 5-position to the 4-position to form the corresponding 5-hydroxy-4-acyloxy Saishin N derivative.

Preferably, the treating with heat is effected in a solvent medium such as one in which the 5-acyloxy-4-hydroxy and 5-hydroxy-4-acyloxy Saishin N derivatives are capable of reaching an equilibrium mixture, and particularly concerns the treating of a 5-acyloxy-4-hydroxy-2,6,6-trimethyl-2-cyclohepten-1-one to form the corresponding 5-hydroxy-4-acyloxy-2,6,6-trimethyl-2-cyclohepten-1-one.

Generally, in regard to the above formula for Compound A, each R (i.e. Rx and Ry) independently is a hydrogen atom or an alkyl, alkenyl, aralkenyl, aralkyl, heterocyclic-alkyl (i.e. heterocyclic substituted alkyl), or acyl group. Such groups may each independently be an unsubstituted or optionally substituted group.

Preferably, the alkyl group is a straight or branched chain lower alkyl group, e.g. having 1 to 4 carbon atoms.

Preferably, the alkenyl group is a straight or branched chain lower alkenyl group, e.g. having 2 to 5, especially 2 to 4, carbon atoms.

Preferably, the aralkenyl group has a straight or branched chain alkenyl moiety, and particularly a lower alkenyl moiety, e.g. having 2 to 5, especially 2 to 4, carbon atoms, and an aryl moiety, e.g. having 6 to 10 ring carbon atoms, and particularly a mononuclear or polynuclear aryl moiety, such as a styryl, cinnamyl or naphthylethenyl group.

Preferably, the aralkyl group has a straight or branched chain alkyl moiety, and particularly a lower alkyl moiety, e.g. having 1 to 4 carbon atoms, and an aryl moiety, e.g. having 6 to 10 ring carbon atoms, and particularly a mononuclear or polynuclear aryl moiety, such as a benzyl, phenethyl or naphthylmethyl group.

Preferably, the heterocyclic-alkyl group has a straight or branched chain alkyl moiety, and particularly a lower alkyl moiety, e.g. having 1 to 4 carbon atoms, and a heterocyclic moiety, e.g. having 5 to 10, especially 5 to 9, or 5 to 6, ring members including one or more (at least one) sulfur, nitrogen and oxygen heteroatoms, such as a thenyl, picolyl or furfuryl group.

Preferably, the acyl group is an aliphatic acyl, aromatic-aliphatic acyl, aromatic acyl or heterocyclic acyl group, and more particularly is an alkanoyl, alkenoyl, aralkenoyl, aroyl, heterocyclic-alkanoyl or heterocyclic carbonyl group.

Preferably, the aliphatic acyl group is a straight or branched chain, saturated or unsaturated, e.g. ethylenically unsaturated, aliphatic acyl group, more preferably a lower aliphatic acyl group, e.g. having 2 to 6 carbon atoms, and particularly an alkanoyl or alkenoyl group, especially a lower alkanoyl group, e.g. having 2 to 6 carbon atoms, or a lower alkenoyl group, e.g. having 3 to 6 carbon atoms.

Preferably, the aromatic-aliphatic acyl group has a straight or branched chain, saturated or unsaturated, e.g. ethylenically unsaturated, aliphatic acyl moiety, and particularly a lower aliphatic acyl moiety, e.g. having 2 to 6 carbon atoms, and more particularly an alkanoyl or alkenoyl moiety, especially a lower alkanoyl moiety, e.g. having 2 to 6 carbon atoms, or a lower alkenoyl moiety, e.g. having 3 to 6 carbon atoms, and an aromatic moiety, e.g. having 6 to 10 ring carbon atoms, and particularly a mononuclear or polynuclear aryl moiety. More preferably, the aromatic-aliphatic acyl group is an araliphatic acyl group, and in particular an aralkanoyl group such as a phenyl acetyl group, or an aralkenoyl group such as a cinnamoyl group, and more especially the aromatic-aliphatic acyl group is an aralkenoyl group.

Preferably, the aromatic acyl group has 6 to 10 ring carbon atoms in the aromatic moiety, and particularly a mononuclear or polynuclear aromatic moiety, and more preferably is an aromatic carbonyl group, and in particular an aroyl group such as a benzoyl or naphthoyl group.

Preferably, the heterocyclic acyl group has 5 to 10, especially 5 to 9, ring members including one or more (at least one) sulfur, nitrogen and oxygen heteroatoms, in the heterocyclic moiety, and in particular is a heterocyclic alkanoyl group, preferably having a straight or branched chain alkanoyl moiety, especially a lower alkanoyl moiety, e.g. having 2 to 5, especially 2 to 4, carbon atoms, such as a thiazolyl acetyl group, or is a heterocyclic carbonyl group, such as a furoyl, pyrrolyl carbonyl, thenoyl, imidazolyl carbonyl or benzimidazolyl carbonyl groups. The heterocyclic alkanoyl and heterocyclic carbonyl groups may be collectively defined as a heterocyclic alkanoyl (i.e. heterocyclic substituted alkanoyl) group having at least one carbon atom in the alkanoyl moiety.

Where R (i.e. Rx and Ry) is a hydrogen atom (i.e. where —OR is a hydroxy group), the hydrogen atom may be replaced by a hydroxy protective group such as a tetrahydropyranyl group, during particular production process procedures. Where a hydroxy group is present as a chain or ring substituent in the case of an optionally substituted alkyl, alkenyl, aralkenyl, aralkyl, heterocyclic-alkyl or acyl group, the hydrogen atom of the hydroxy group may likewise be replaced by a hydroxy protective group such as a tetrahydropyranyl group, during particular production process procedures.

Similarly, where an amino group is present as a ring substituent in the case of an optionally substituted acyl group, and particularly a heterocyclic acyl group, such as a heterocyclic alkanoyl group, e.g. an amino-thiazolyl acetyl group, a hydrogen atom on the amino group may also be replaced by an amino protective group such as a trityl group, during particular production process procedures.

The hydroxy protective group for R, where a hydrogen atom, or for any hydroxy group, includes a lower alkyl group, e.g. having 1 to 4 carbon atoms, an acetal group, and particularly a chain acetal group, such as a tetrahydropyranyl, tetrahydrothiopyranyl, 4-methoxytetrahydropyranyl, tetrahydrofuranyl, 1-ethoxyethyl, 1-methyl-1-methoxyethyl or 1-isopropyloxyethyl group, or a silyl ether group such as trimethylsilyl ether or tert-butyldimethylsilyl ether group.

In the case of Saishin N as reactant, the protective group for both hydroxy groups in the 4- and 5-positions is preferably a cyclic acetal such as an isopropylidene, benzylidene or anisylidene group, but it may also be a said chain acetal group.

The amino protective group for an amino group which is present as a ring substituent in the case of aromatic-aliphatic acyl, aromatic acyl and heterocyclic acyl groups, especially aralkenoyl, aroyl, heterocyclic alkanoyl and heterocyclic carbonyl groups, includes benzyl, trityl and benzoyloxycarbonyl groups.

Moreover, in the case of heterocyclic-alkyl, heterocyclic alkanoyl and heterocyclic carbonyl groups, an activated hydrogen atom on the heterocyclic ring moiety thereof may be protected by a hydrogen protective group such as a benzyl, trityl or benzoyloxycarbonyl group.

The carbonyl protective group for the 1-oxo group, during particular production process procedures, is preferably a conventional carbonyl protective group, such as a hydrazone, more particularly a dimethyl hydrazone, group.

Preferably, the chain substituents for the alkyl, alkenyl and aliphatic acyl, especially alkanoyl and alkenoyl, groups include one or more (at least one) hydroxy (which may be protected by a said hydroxy protective group), carboxyl, and/or lower alkoxy carbonyl groups, the latter group preferably having 1 to 4 carbon atoms.

Preferably, the ring substituents for the aralkenyl, aralkyl and heterocyclic-alkyl groups include one or more (at least one) lower alkyl; lower alkoxy carbonyl; acyl, especially lower alkanoyl, aroyl and aralkenoyl, such as acetyl, benzoyl and cinnamoyl; hydroxy (which may be protected by a said hydroxy protective group); lower alkoxy; halo (halogen), including fluoro, chloro, bromo and iodo; and/or nitro groups; the lower alkyl, lower alkoxy carbonyl, lower alkanoyl and lower alkoxy groups each preferably having 1 to 4 carbon atoms, and the acyl, especially lower alkanoyl, aroyl and aralkenoyl, groups such as the acetyl, benzoyl and cinnamoyl groups, optionally independently containing one or more (at least one) chain or ring substituents.

Preferably, the ring substituents for the aromatic-aliphatic acyl, aromatic acyl and heterocyclic acyl, especially aralkenoyl, aroyl, heterocyclic alkanoyl and heterocyclic carbonyl, groups include one or more (at least one) of said lower alkyl; lower alkoxy carbonyl; acyl, especially lower alkanoyl, aroyl and aralkenoyl, such as acetyl, benzoyl and cinnamoyl; hydroxy protected by as protected by a said hydroxy protective group); lower alkoxy; halo (halogen), including fluoro, chloro, bromo and iodo; and/or nitro groups; the lower alkyl, lower alkoxy carbonyl, lower alkanoyl and lower alkoxy groups each preferably having 1 to 4 carbon atoms, and the acyl, especially lower alkanoyl, aroyl and aralkenoyl, groups such as the acetyl, benzoyl and cinnamoyl groups, optionally independently containing one or more (at least one) chain or ring substituents; and/or one or more (at least one) carboxyl; lower acyloxy; especially lower alkanoyloxy, such as acetoxy, propionyloxy, butyryloxy, isobutyryloxy, valeryloxy and isovaleryloxy; amino (which may be protected by a said amino protective group); acyl amino, especially lower alkanoyl amino, aroyl amino and aralkenoyl amino, such as acetyl amino, benzoyl amino and cinnamoyl amino; and/or lower alkyl amino, including mono- and di- lower alkyl amino, groups; the lower acyloxy, lower alkanoyloxy, lower alkanoyl amino and lower alkyl amino groups each preferably having 1 to 4 carbon atoms.

As above noted, the activated hydrogen atom on the heterocyclic ring moiety of a heterocyclic-alkyl or heterocyclic acyl, especially heterocyclic alkanoyl and heterocyclic carbonyl, group may be protected by a said hydrogen protective group such as a benzyl, trityl or benzoyloxycarbonyl group.

According to a preferred embodiment, each R independently is a hydrogen atom or an alkyl, alkenyl, aralkenyl, aralkyl, heterocyclic-alkyl, aliphatic acyl, e.g. alkanoyl or alkenoyl, aromatic-aliphatic acyl, e.g. aralkenoyl, aromatic acyl, e.g. aroyl, or heterocyclic acyl, e.g. heterocyclic alkanoyl or heterocyclic carbonyl, group.

The alkyl, alkenyl and aliphatic acyl, e.g. alkanoyl and alkenoyl, groups are each independently optionally chain substituted with one br more of said hydroxy, carboxyl and/or lower alkoxy carbonyl groups.

The aralkenyl, aralkyl and heterocyclic-alkyl groups are each independently optionally ring substituted with one or more of said lower alkyl, lower alkoxy carbonyl, lower alkanoyl, aroyl, aralkenoyl, hydroxy, lower alkoxy, halo and/or nitro groups.

The aromatic-aliphatic acyl, e.g. aralkenoyl, aromatic acyl, e.g. aroyl, and heterocyclic acyl, e.g. heterocyclic alkanoyl and heterocyclic carbonyl, groups are each independently optionally ring substituted with one or more of said lower alkyl, lower alkoxy carbonyl, lower alkanoyl, aroyl, aralkenoyl, hydroxy, lower alkoxy, halo, nitro, carboxyl, lower alkanoyloxy, amino, lower alkanoyl amino, aroyl amino, aralkenoyl amino and/or lower alkyl amino groups.

According to a particular feature, each R independently is a hydrogen atom or an alkyl group optionally preferably substituted with a hydroxy or lower alkoxycarbonyl group; an alkenyl group; an aralkyl group optionally preferably substituted with a lower alkoxy group; an alkanoyl group; an aralkenoyl group optionally preferably substituted with a hydroxy, lower alkoxy, nitro or amino group; an aroyl group optionally preferably substituted with a lower alkoxy carbonyl, hydroxy, lower alkoxy, halo, nitro, carboxyl, amino, lower alkanoyl amino or di lower alkyl amino group; a heterocyclic alkanoyl group optionally preferably substituted with an amino group; or a heterocyclic carbonyl group optionally preferably substituted with a lower alkyl or amino group.

While specific embodiments of the invention have been shown and described in detail to illustrate the application of the principles of the invention, it will be understood that the invention may be embodied otherwise without departing from such principles.

What is claimed is:
1. A Saishin N compound of the formula

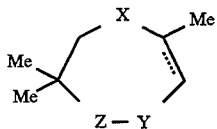

wherein X represents a carbonyl group or a >CH—ORx group, or X bonds to a carbon atom in Y or Z to represent a >C(ORx)—O— group, Y and Z may be the same or different and each represents a carbonyl group or a >CH—ORy group, or each bonds to an oxygen atom in X to represent a >CH— group, each Me represents a methyl group, the broken line represents an optional bond, and Rx and Ry may be the same or different and each represents a hydrogen atom or an alkyl, alkenyl, aralkenyl, aralkyl, heterocyclic-alkyl or acyl group, provided that when X is a carbonyl group and the broken line is a bond and Y is a >CH—ORy group and Z is also a >CH—ORy group, then only one Ry thereof may be a hydrogen atom, thereby excluding Saishin N.

2. A compound of claim 1 wherein the acyl group is an alkanoyl, alkenoyl, aralkenoyl, aroyl, heterocyclic-alkanoyl or heterocyclic carbonyl group.

3. A compound of claim 2 wherein the alkyl, alkenyl, alkanoyl and alkenoyl groups are each optionally substituted with one or more hydroxy, carboxyl or lower alkoxy carbonyl groups, the aralkenyl, aralkyl and heterocyclic-alkyl groups are each optionally substituted with one or more lower alkyl, lower alkoxy carbonyl, acyl, hydroxy, lower alkoxy, halo or nitro groups, and the aralkenoyl, aroyl, heterocyclic-alkanoyl and heterocyclic carbonyl groups are each optionally substituted with one or more lower alkyl, lower alkoxy carbonyl, acyl, hydroxy, lower alkoxy, halo, nitro, carboxyl, lower acyloxy, amino, acyl amino or lower alkyl amino groups.

4. A compound of claim 2 wherein the alkyl, alkenyl, alkanoyl and alkenoyl groups are each optionally substituted with one or more hydroxy, carboxyl or lower alkoxy carbonyl groups, the aralkenyl, aralkyl and heterocyclic-alkyl groups are each optionally substituted with one or more lower alkyl, lower alkoxy carbonyl, lower alkanoyl, aroyl, aralkenoyl, hydroxy, lower alkoxy, halo or nitro groups, and the aralkenoyl, aroyl, heterocyclic-alkanoyl and heterocyclic carbonyl groups are each optionally substituted with one or more lower alkyl, lower alkoxy carbonyl, lower alkanoyl, aroyl, aralkenoyl, hydroxy, lower alkoxy, halo, nitro, carboxyl, lower alkanoyloxy, amino, lower alkanoyl amino, aroyl amino, aralkenoyl amino or lower alkyl amino groups.

5. A compound of claim 1 which is selected from the group consisting of 5-hydroxy-4-(4-nitrobenzoyloxy)-2,6,6-trimethyl-2-cyclohepten-1-one, 5-hydroxy-4-(4-aminobenzoyloxy)-2,6,6-trimethyl-2-cyclohepten-1-one, 5-hydroxy-4-(1-methyl-2-pyrrolylcarbonyloxy)-2,6,6-trimethyl-2-cyclohepten-1-one, 5-(2,4-diaminobenzoyloxy)-4-methoxy-2,6,6-trimethyl-2-cyclohepten-1-one, 2,4-cis-1-methoxy-2,6,6-trimethyl-8-oxabicyclo[3.2.1] octan-4-ol, and 1-methoxy-4-(4-aminobenzoyloxy)-2,6,6-trimethyl-8-oxabicyclo[3.2.1]oct-2-ene.

6. 5-Hydroxy-4-(4-aminobenzoyloxy)-2,6,6-trimethyl-2-cyclohepten-1-one.

7. 2,4-Cis-1-methoxy-2,6,6-trimethyl-8-oxabicyclo [3.2.1]octan-4-ol.

8. A compound of claim 1 wherein X is a >C(ORx)—O— group, Y is a >CH— group, and Z is a carbonyl group or a >CH—ORy group.

9. A compound of claim 1 wherein X is a C(ORx)—O— group, Y is a carbonyl group or a >CH—ORy group, and Z is a >CH— group.

10. A compound of claim 1 wherein X is a carbonyl group, Y is a >CH—ORy group in which Ry is an alkyl, alkenyl, aralkenyl, aralkyl or heterocyclic-alkyl group, and Z is a >CH—ORy group in which Ry is a hydrogen atom, and the bond represented by the broken line is present.

11. A compound of claim 1 wherein X is a >C(ORx)—O— group in which Rx is an alkyl, alkenyl, aralkenyl, aralkyl or heterocyclic-alkyl group, Y is a >CH—ORy group in which Ry is an alkyl, alkenyl, aralkenyl, aralkyl or heterocyclic-alkyl group, and Z is a >CH— group, and the bond represented by the broken line is present.

12. A compound of claim 1 wherein X is a carbonyl group, Y is a >CH—ORy group in which Ry is an alkyl, alkenyl, aralkenyl, aralkyl or heterocyclic-alkyl group, and Z is a >CH—ORy group in which Ry is an acyl group, and the bond represented by the broken line is present.

13. A compound of claim 1 wherein X is a >C(ORx)—O— group in which Rx is an acyl group, Y is a >CH—ORy group in which Ry is an alkyl, alkenyl, aralkenyl, aralkyl or heterocyclic-alkyl group, and Z is a >CH— group, and the bond represented by the broken line is present.

14. A compound of claim 1 wherein X is a carbonyl group, Y is a >CH—ORy group in which Ry is a hydrogen atom, and Z is a >CH—ORy group in which Ry is an acyl group, and the bond represented by the broken line is present.

15. A compound of claim 1 wherein X is a carbonyl group, Y is a >CH—ORy group in which Ry is an acyl group, and Z is a >CH—ORy group in which Ry is a hydrogen atom, and the bond represented by the broken line is present.

16. A compound of claim 1 wherein X is a carbonyl group, and Y and Z are each a >CH—ORy group in which Ry is an acyl group, and the bond represented by the broken line is present.

17. A compound of claim 1 wherein X is a carbonyl group, Y is a >CH—ORy group in which Ry is a hydrogen atom, and Z is a >CH—ORy group in which Ry is an alkyl, alkenyl, aralkenyl, aralkyl or heterocyclic-alkyl group, and the bond represented by the broken line is present.

18. A compound of claim 1 wherein X is a carbonyl group, Y is a >CH—ORy group in which Ry is an alkyl, alkenyl, aralkenyl, aralkyl, heterocyclic-alkyl or acyl group or a protective group, Z is a >CH—ORy group in which Ry is an alkyl, alkenyl, aralkenyl, aralkyl, heterocyclic-alkyl or acyl group or a protective group, or both the Ry of Y and the Ry of Z are combined together to form a protective group, and the bond represented by the broken line is present.

19. A compound of claim 1 wherein X is a >CH—ORx group in which Rx is a hydrogen atom, Y is a >CH—ORy group in which Ry is an alkyl, alkenyl, aralkenyl, aralkyl, heterocyclic-alkyl or acyl group or a protective group, Z is a >CH—ORy group in which Ry is an alkyl, alkenyl, aralkenyl, aralkyl, heterocyclic-alkyl or acyl group or a protective group, or both the Ry of Y and the Ry of Z are combined together to form a protective group, and the bond represented by the broken line is present.

20. A compound of claim 1 wherein X is a >C(ORx)—O— group in which Rx is an alkyl, alkenyl, aralkenyl, aralkyl, heterocyclic-alkyl or acyl group, Y is a >CH— group, and Z is a >CH—ORy group in which Ry is an alkyl, alkenyl, aralkenyl, aralkyl, heterocyclic-alkyl or acyl group, and the bond represented by the broken line is present.

21. A compound of claim 1 wherein X is a >C(ORx)—O— group in which Rx is an alkyl, alkenyl, aralkenyl, aralkyl; heterocyclic-alkyl or acyl group, Y is a >CH—ORy group in which Ry is an alkyl, alkenyl, aralkenyl, aralkyl, heterocyclic-alkyl or acyl group, and Z is a >CH— group, and the bond represented by the broken line is present.

22. A compound of claim 1 wherein the bond represented by the broken line is present.

23. A compound of claim 1 wherein the bond represented by the broken line is absent.

24. A compound of claim 1 wherein X is a carbonyl group, Y is a >CH—ORy group in which Ry is a hydrogen atom or an alkyl, alkenyl, aralkenyl, aralkyl, heterocyclic-alkyl or acyl group, and Z is a >CH—ORy group in which Ry is a hydrogen atom, and the bond represented by the broken line is absent.

25. A compound of claim 1 wherein X is a >C(ORx)—O— group in which Rx is a hydrogen atom, Y is a >CH—ORy group in which Ry is a hydrogen atom or an alkyl, alkenyl, aralkenyl, aralkyl, heterocyclic-alkyl or acyl group, and Z is a >CH— group, and the bond represented by the broken line is absent.

26. A compound of claim 1 wherein x is a >C(ORx)—O— group in which Rx is an alkyl, alkenyl, aralkenyl, aralkyl, heterocyclic-alkyl or acyl group, Y is a >CH—ORy group in which Ry is a hydrogen atom or an alkyl, alkenyl, aralkenyl, aralkyl, heterocyclic-alkyl or acyl group, and Z is a >CH— group, and the bond represented by the broken line is absent.

27. An antiulcer pharmaceutical composition comprising an antiulcer effective amount of a Saishin N derivative of claim 1 together with a pharmaceutical carrier.

28. A method of inhibiting ulcers in a subject comprising administering to the subject an antiulcer effective amount of a Saishin N derivative of claim 1.

* * * * *